United States Patent
Mathias et al.

(10) Patent No.: US 11,986,512 B2
(45) Date of Patent: May 21, 2024

(54) COMPOSITIONS AND METHODS FOR CANCER THERAPY

(71) Applicants: Thetis Pharmaceuticals LLC, Ridgefield, CT (US); Beth Israel Deaconess Medical Center, Boston, MA (US)

(72) Inventors: Gary Mathias, Ridgefield, CT (US); Dipak Panigrahy, Boston, MA (US); John Parkinson, Ridgefield, CT (US); Aaron Mathias, Ridgefield, CT (US); Frank C. Sciavolino, Ridgefield, CT (US)

(73) Assignees: Thetis Phamaceuticals LLC; Beth Israel Deaconess Medical Center

( * ) Notice: Subject to any disclaimer, the term of this patent is extended or adjusted under 35 U.S.C. 154(b) by 0 days.

(21) Appl. No.: 18/049,736

(22) Filed: Oct. 26, 2022

(65) Prior Publication Data
US 2023/0133085 A1    May 4, 2023

Related U.S. Application Data

(60) Provisional application No. 63/263,028, filed on Oct. 26, 2021.

(51) Int. Cl.
| | | |
|---|---|---|
| A61K 38/17 | (2006.01) | |
| A61K 39/00 | (2006.01) | |
| A61K 45/06 | (2006.01) | |
| A61P 35/00 | (2006.01) | |
| C07K 16/28 | (2006.01) | |

(52) U.S. Cl.
CPC .......... *A61K 38/1793* (2013.01); *A61K 45/06* (2013.01); *A61P 35/00* (2018.01); *C07K 16/2803* (2013.01); *C07K 16/2818* (2013.01); *A61K 2039/505* (2013.01)

(58) Field of Classification Search
CPC .............. A61K 2039/505; A61K 45/06; A61K 38/1793; C07K 16/2803; A61P 35/00
See application file for complete search history.

(56) References Cited

U.S. PATENT DOCUMENTS

| | | |
|---|---|---|
| 2006/0293288 A1 | 12/2006 | Serhan |
| 2010/0105773 A1 | 4/2010 | Smith |
| 2018/0110751 A1* | 4/2018 | Sciavolino ............ A61K 45/06 |
| 2020/0330551 A1 | 10/2020 | Kantarci et al. |
| 2021/0147558 A1 | 5/2021 | Poirier |

OTHER PUBLICATIONS

Bai et al. ("Inhibition of lung cancer growth and metastasis by DHA and its metabolite, RvD1, through miR-138-5p/FOXC1 pathway", J Exp Clin Cancer Res 38, 479 (2019) (Year: 2019).*
Zhang et al. ("Resolution of Cancer-Promoting Inflammation: A New Approach for Anticancer Therapy." Front Immunol. Feb. 2, 2017; 8:71) (Year: 2017).*

(Continued)

*Primary Examiner* — Scarlett Y Goon
*Assistant Examiner* — Audrey L Buttice
(74) *Attorney, Agent, or Firm* — KDW Firm PLLC

(57) ABSTRACT

The present invention relates to compositions comprising resolvins and their use in methods of treating cancer.

44 Claims, 11 Drawing Sheets

(56) References Cited

OTHER PUBLICATIONS

Vannitamby et al. ("Aspirin-Triggered Resolvin D1 Reduces Proliferation and the Neutrophil to Lymphocyte Ratio in a Mutant KRAS-Driven Lung Adenocarcinoma Model". Cancers. 2021; 13(13):3224) (Year: 2021).*

Or, M., et al (2021) A systematic review and meta-analysis of treatment-related toxicities of curative and palliative radiation therapy in non-small cell lung cancer Scientific Reports 11; 5939, published online Mar. 15, 2021 (Year: 2021).*

Gartung, A. et al., "Synergy between resolvins and immune checkpoint blockade in a novel transplantable FANCC murine head and Neck tumor model", 2019, vol. 33, No. S1, p. 496.10 [abstract].

International Search Report and Written Opinion for the International Patent Application No. PCT/US2022/047806, dated Feb. 13, 2023, 12 pages.

Al Shoyaib, Abdullah et al. "Intraperitoneal Route of Drug Administration: Should it Be Used in Experimental Animal Studies ?. " Pharmaceutical research vol. 37,1 12. Dec. 23, 2019.

Alvarez et al., "RvE1 Impacts the Gingival Inflammatory Infiltrate by Inhibiting the T Cell Response in Experimental Periodontitis" Front. Immunol., May 3, 2021—Sec. Mucosal Immunity—vol. 12—2021.

Arita et al., "Metabolic Inactivation of Resolvin E1 and Stabilization of Its Anti-inflammatory Actions*" Mechanisms of Signal Transduction| vol. 281, Issue 32, p. 22847-22854, Aug. 2006.

Babic, A et al. "Plasma inflammatory cytokines and survival of pancreatic cancer patients." Clinical and translational gastroenterology vol. 9,4 145. Apr. 25, 2018.

Coussens, L., Werb, Z. Inflammation and cancer. Nature 420, 860-867 (2002).

Li, J.; Leong, M. M.; Stewart, A.; Rizzacasa, M. A. Beilstein J. Org. Chem. 2013, 9, 2762-2766.

Chiurchiu, Valerio et al. "Proresolving lipid mediators resolvin D1, resolvin D2, and maresin 1 are critical in modulating T cell responses." Science translational medicine vol. 8,353 (2016).

Ping Yu, Jason C. Steel, Meili Zhang, John C. Morris, Thomas A. Waldmann; Simultaneous Blockade of Multiple Immune System Inhibitory Checkpoints Enhances Antitumor Activity Mediated by Interleukin-15 in a Murine Metastatic Colon Carcinoma Model. Clin Cancer Res Dec. 15, 2010; 16 (24): 6019-6028.

Fishbein, Anna et al. "Carcinogenesis: Failure of resolution of inflammation." Pharmacology therapeutics vol. 218 (2021): 107670.

Grivennikov, Sergei I et al. "Immunity, inflammation, and cancer." Cell vol. 140,6 (2010): 883-99.

Keppel Hesselink, Jan M. "Fundamentals of and Critical Issues in Lipid Autacoid Medicine: A Review." Pain and therapy vol. 6,2 (2017): 153-164. doi:10.1007/s40122-017-0075-4.

Hohneker, John et al. "Perspectives on adherence and persistence with oral medications for cancer treatment." Journal of oncology practice vol. 7,1 (2011): 65-7.

Lavy et la., "Specialized Pro-Resolving Mediators Mitigate Cancer-Related Inflammation: Role of Tumor-Associated Macrophages and Therapeutic Opportunities" Front. Immunol., Jun. 30, 2021 Sec. Inflammation—vol. 12—2021.

Lechner, Melissa G et al. "Immunogenicity of murine solid tumor models as a defining feature of in vivo behavior and response to immunotherapy." Journal of immunotherapy (Hagerstown, Md. : 1997) vol. 36,9 (2013): 477-89.

Li, Tong et al. "The outstanding antitumor capacity of CD4+ T helper lymphocytes." Biochimica et biophysica acta. Reviews on cancer vol. 1874,2 (2020).

Mattoscio, Domenico et al. "Resolvin D1 reduces cancer growth stimulating a protective neutrophil-dependent recruitment of anti-tumor monocytes." Journal of experimental clinical cancer research : CR vol. 40,1 129. Apr. 12, 2021.

Mizraji et al., "Resolvin D2 Restrains Th1 Immunity and Prevents Alveolar Bone Loss in Murine Periodontitis" Front. Immunol., Apr. 25, 2018 Sec. Inflammation—vol. 9—2018.

Obrosov, Alexander et al. "Effect of Fish Oil vs. Resolvin D1, E1, Methyl Esters of Resolvins D1 or D2 on Diabetic Peripheral Neuropathy." Journal of neurology & neurophysiology vol. 8,6 (2017): 453. doi:10.4172/2155-9562.1000453.

Oner, Fatma et al. "Resolvin E1 Regulates Th17 Function and T Cell Activation." Frontiers in immunology vol. 12 637983. Mar. 17, 2021.

Ostroumov, Dmitrij et al. "CD4 and CD8 T lymphocyte interplay in controlling tumor growth." Cellular and molecular life sciences : CMLS vol. 75,4 (2018): 689-713.

Panigrahy, Dipak et al. "Preoperative stimulation of resolution and inflammation blockade eradicates micrometastases." The Journal of clinical investigation vol. 129,7 2964-2979. Jun. 17, 2019.

Perez-Ruiz, Elisabeth et al. "Prophylactic TNF blockade uncouples efficacy and toxicity in dual CTLA-4 and PD-1 Immunotherapy." Nature vol. 569,7756 (2019): 428-432.

Serhan, C. Pro-resolving lipid mediators are leads for resolution physiology. Nature 510, 92-101 (2014).

Serhan, Charles N et al. "Lipid mediators in the resolution of inflammation." Cold Spring Harbor perspectives in biology vol. 7,2 a016311. Oct. 30, 2014.

Sulciner, Megan L et al. "Resolvins suppress tumor growth and enhance cancer therapy." The Journal of experimental medicine vol. 215,1 (2018): 115-140.

Thomsen, Maria et al. "Interleukin-6 and C-reactive protein as prognostic biomarkers in metastatic colorectal cancer." Oncotarget vol. 7,46 (2016): 75013-75022.

Todoric, Jelena et al. "Targeting Inflammation in Cancer Prevention and Therapy." Cancer prevention research (Philadelphia, Pa.) vol. 9,12 (2016): 895-905.

Togashi, Yosuke et al. "Regulatory T cells in cancer immunosuppression—implications for anticancer therapy." Nature reviews. Clinical oncology vol. 16,6 (2019): 356-371.

Trilleaud, C et al. "Agonist anti-ChemR23 mAb reduces tissue neutrophil accumulation and triggers chronic inflammation resolution." Science advances vol. 7,14 eabd1453. Apr. 2, 2021.

Vik, Anders et al. "Recent advances in the chemistry and biology of anti-inflammatory and specialized pro-resolving mediators biosynthesized from n-3 docosapentaenoic acid." Bioorganic & medicinal chemistry letters vol. 27,11 (2017): 2259-2266.

Waldman, Alex D et al. "A guide to cancer immunotherapy: from T cell basic science to clinical practice." Nature reviews. Immunology vol. 20, 11 (2020): 651-668.

Weeda, Erin R et al. "Medication adherence to injectable glucagon-like peptide-1 (GLP-1) receptor agonists dosed once weekly vs once daily in patients with type 2 diabetes: A meta-analysis." International journal of clinical practice vol. 75,9 (2021).

Xu, ZZ., Zhang, L., Liu, T et al. Resolvins RvE1 and RvD1 attenuate inflammatory pain via central and peripheral actions. Nat Med 16, 592-597 (2010).

Yoo, Sungjae et al. "Resolvins: Endogenously-Generated Potent Painkilling Substances and their Therapeutic Perspectives." Current neuropharmacology vol. 11,6 (2013): 664-76.

* cited by examiner

COMPOSITIONS AND METHODS FOR CANCER THERAPY

CROSS-REFERENCE TO RELATED APPLICATIONS

This application claims the benefit of priority of U.S. Provisional Application Ser. No. 63/263,028 filed Oct. 26, 2021, the contents of which are hereby incorporated by reference in their entirety.

FIELD OF THE INVENTION

The present invention relates to compositions comprising resolvins and salts thereof, and their use in therapy, particularly in the treatment of cancer.

BACKGROUND

The inflammatory response in animals has two phases: initiation and resolution. At the cellular level, initiation is characterized by edema and the accumulation of immune cells such as neutrophils, monocytes, and macrophages. The initiation phase of the inflammatory response has long been recognized as an active process driven by metabolites of arachidonic acid such as the prostaglandins $PGE_2$ and $PGD_2$, which are chemo-attractants for eosinophils, neutrophils and monocytes, and the leukotrienes, especially $LTB_4$ which elicit adhesion, chemotaxis, and aggregation of leukocytes. In order for the inflamed tissue to return to a healthy state, the excess inflammatory cells, cellular debris, and other remnants of the host defense and any invading microorganisms must be cleared. This 'resolution' phase of the inflammatory response was for many years believed to be a passive process, the result of the dilution of the chemo-attractants of the initiation phase.

Today, resolution of inflammation is recognized as an active process, driven by various molecules that counteract the pro-inflammatory effects of prostaglandins and leukotrienes. For example, resolvins are autacoids produced locally at the site of inflammation that promote the resolution of inflammation by recruiting non-inflammatory monocytes, which differentiate into macrophages to remove excess neutrophils and cellular debris. Resolvins are part of a class of 'specialized pro-resolving mediators' ("SPMs") of inflammation that also include lipoxins, protectins, and maresins. Serhan et al., "Lipid Mediators of Inflammation", Cold Spring Harb Perspect Biol 2015; 7:a016311.

Unresolved inflammation is widely recognized as a unifying component in many chronic diseases and disorders, including cancer. Serhan, C. N., *Nature* 2014 510:92-101; Coussens et al. *Nature* 2002; 420, 860-867, Grivennikov et al. *Cell.* 2010; 140(6):883-99, Todoric et al. *Cancer Prev Res.* 2016; 9(12):895-905; Fishbein et al. *Pharmacol Ther.* 2021; 218:107670. With respect to cancer, experimental studies demonstrate that inflammation can stimulate tumor initiation, growth, and metastasis, and observational clinical studies suggest that systemic inflammation in cancer patients is associated with worse survival outcomes. Thomsen et al., *Oncotarget.* 2016 Nov. 15; 7(46):75013-75022k; Babic et al., *Clin Transl Gastroenterol.* 2018 Apr. 25; 9(4):145.

Using preclinical animal models, Sulciner describes the use of continuous intraperitoneal (IP) infusion of three well-characterized SPMs including resolvin E1 (RvE1), resolvin D1 (RvD1), and resolvin D2 (RvD2) to treat solid tumor cancers in preclinical models of lymphoma, lung cancer, breast cancer, and pancreatic cancer. The use of continuous infusion enabled much lower doses to be used compared with previous studies that relied on IP injection. Both dosing regimens were premised on the need to maintain systemic exposure of the resolvins due to their rapid metabolic inactivation and consequently short biological half-life. Arita et al. *J Biol. Chem.* 281, 32 (2006): 22847-54; Xu et al, *Nat. Med* 2010; Yoo et al. *Curr. Neuropharmacol.* (2013); Obsorov et al. *J. Neuro. Neurophy.* 2017; Valdes et al. *Sci. Reports* (2017); Hesselink. *Pain and therapy* vol. 6, 2 (2017); Lavy et al., *Front. Immunol.*, 12, 1 (2021).

Arita determined that oxidoreductase enzymes conserved in all mammalian species catalyze the conversion of RvE1 into 18-oxo-RvE1, which was found to be "devoid of activity" in zymosan-induced peritonitis, whereas an equimolar dose of "RvE1 potently reduced polymorphonuclear leukocyte (PMN) recruitment". Arita also notes that resolvins undergo metabolic inactivation that is similar to other "eicosanoids such as prostaglandins, leukotrienes, and lipoxins, which are generated from stored precursors, exert their bioactions at specific receptors, and are rapidly inactivated via local enzymatic catabolism in target tissues." Investigating the analgesic effects of intrathecal administration of natural RvE1 compared to a stable RvE1 analog, Xu demonstrated that of the effects of the analog "designed to resist rapid local metabolic inactivation of RvE1" lasted 6 hours or 3 times longer than natural RvE1.

Yoo reports that resolvins are "highly unstable lipids compared to their precursors such as DHA and EPA" and that "the natural forms are likely prone to degradation or metabolism". Valdes notes that "resolvins are rapidly degraded in vivo resulting in a short biological half-life". In a report on the therapeutic use of lipid autacoids including resolvins, Hesselink notes that such compounds have "great promise" but require significant formulation development because "most compounds have a short half-life". This obstacle to therapeutic use of natural resolvins and other SPMs for treatment of cancer is also highlighted by Lavy, noting that "native SPMs" have the disadvantage of a "short half-life."

Thus, despite their potential as anti-cancer agents reported in Sulciner and others, clinical development of resolvins has been hindered, in part by the insufficient bioavailability and rapid clearance of these molecules. One way to overcome the "restricted bioavailability and rapid clearance" of specialized proresolving mediators, such as resolvins, was provided by Trilleaud et al., *Sci. Adv.* 2021. Trilleaud describes the use of a monoclonal antibody developed to activate ChemR23, thereby eliminating the need to administer its natural ligand, RvE1. The rationale for using the extended plasma half-life ChemR23 agonist antibody was to overcome the "restricted bioavailability and rapid clearance" of SPMs, such as resolvins. Another approach to overcome the short half-life of resolvins that is used in many preclinical studies of cancer therapy was to administer the resolvin by daily intraperitoneal (IP) injection or using a continuous infusion regimen, such as an IP osmotic pump. Ye et al. (2018); Sun et al.; Sulciner et al. (2018); US 20200330551.

Others have reported the use of resolvins as a neoadjuvant therapy. Debulking and curative treatment for locoregional disease, such as surgery or radiation therapy, can induce tumor-dormancy escape and subsequent metastatic outgrowth by impairing tumor-specific immunity through inflammation-mediated growth signals and deficient resolution of inflammation. Therefore, in the treatment of cancer with surgical resection or radiation therapy, there is an opportunity in the perioperative period to lower the risk of metastatic growth and relapse via the use of neo-adjuvant therapy to reduce dormancy escape of cancer cells and counter the pro-tumor inflammatory effects of the debulking or curative treatment of the primary tumor. Addressing this opportunity, Panigrahy determined that perioperative use of D-series resolvins administered continuously via intraperitoneal pump beginning two hours before surgery markedly improves survival following tumor resection in the metastatic LLC resection model. Panigrahy D et al. J Clin Invest. 2019; 129(7):2964-2979.

Others have reported the use of resolvins as preventive agents. For example, Kuang et al. (2016) describes chemoprevention with resolvins to alleviate the progression of hepatitis toward liver cancer in a long-term concanavalin A-induced murine model. Notably, Kuang observed that administration of either RvD1 or RvE1 in this model system markedly downregulated levels of CD4+ and CD8+ cells in the liver, which is a marker of poor prognosis and response to treatment in cancer. Ostroumov et al. *Cell Mol Life Sci* (2018). US 20200330551 describes methods for preventing or treating cancer comprising overexpressing of the GPCR receptor of RvE1 known as ChemR23, which may be combined with administering RvE1 where the RvE1 was administered by IP injection prior to or at the time of tumor cell implantation, which does not mimic the clinical setting in which patients present with established tumors or metastatic disease.

There is a need for new compositions and methods to exploit the anti-cancer potential of resolvins. The present invention addresses these needs.

BRIEF SUMMARY

The present invention relates to compositions comprising a resolvin, or a salt thereof, for use in the treatment of cancer. Resolvins are quickly cleared following intravenous or subcutaneous administration, exhibiting a serum half-life of less than one hour. In order to increase bioavailability, prior studies utilized a continuous dosing regimen such as intraperitoneal (IP) administration by a mini-osmotic pump, or daily IP injection. The compositions and methods described here are based, in part, on unexpected findings of efficacy for resolvins and salts of resolvins administered by less than daily (LTD) dosing, and in certain embodiments dosing every six days (Q6D) or seven days (Q7D). The invention further provides methods relating to combination therapy with resolvins and immune checkpoint inhibitors, based on unexpected findings of efficacy.

Accordingly, the disclosure provides methods for treating cancer in a subject in need of such treatment comprising administering to the subject a pharmaceutical composition comprising a resolvin, or a salt thereof. In embodiments, the resolvin or its salt is administered by a non-continuous route, such as by subcutaneous injection or oral dosing. In embodiments, the resolvin or its salt is administered in a dosing regimen of once daily or less than daily (LTD) dosing, for example once every two days (Q2D), or once every three days (Q3D), or once every six days (Q6D), or once every seven days (Q7D). In embodiments, the resolvin or its salt is administered in a dosing regimen of once every three days (Q3D), or once every six days (Q6D), or once every seven days (Q7D). In embodiments, the resolvin or its salt is administered in a dosing regimen of once every two weeks (Q14D), once every three weeks (Q21D), or once every four weeks (Q28D).

In embodiments, the compositions for use in the methods described here comprise a salt of a resolvin. In embodiments, the resolvin salt is peptide or mineral amino acid salt form of a resolvin or its aspirin-triggered counterpart described in Formulas I-IV. The resolvin salts described in Formulas I-IV contain two resolvin molecules ionically bound to at least one basic function provided by a scaffold. For example, in compounds of Formulas I and III, the scaffold is peptide-based; in compounds of Formula IV, the scaffold is a divalent metal-amino acid chelate or divalent metal-peptide chelate; and in compounds of Formula II, the scaffold is either a dipeptide or a monovalent metal or non-metal dipeptide.

In embodiments, the disclosure provides methods for treating cancer in a subject in need of such treatment, the methods comprising administering to the subject a pharmaceutical composition comprising a resolvin, or a salt thereof, in a therapeutic regimen of less than once daily, either alone as monotherapy or as adjuvant therapy, optionally in combination with at least one additional therapeutic agent as described herein.

In embodiments, the resolvin is a sodium, potassium, or magnesium salt.

In embodiments, the resolvin is a mineral amino acid salt of Formula IV, or an enantiomer, polymorph, solvate, or hydrate thereof:

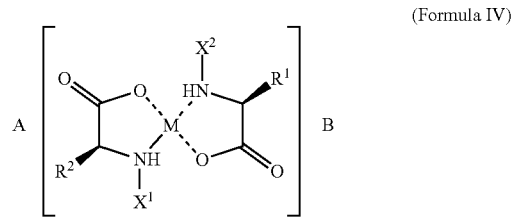

(Formula IV)

wherein
M is a divalent metal selected from magnesium ($Mg^{2+}$), calcium ($Ca^{2+}$), and zinc ($Zn^{2+}$);
A and B are each independently a resolvin molecule;
A and B may be the same or different;
either A or B, but not both, may be absent;
$R^1$ and $R^2$ are each independently a $C_1$-$C_{10}$ alkyl comprising at least one basic function; and
$X^1$ and $X^2$ are each independently H or CO—Z and Z is a peptide comprising 1 to 5 amino acids.

In embodiments, the resolvin is an E or D series resolvin, optionally wherein the E series resolvin is selected from the group consisting of resolvin E1 (RvE1), resolvin E2 (RvE2), resolvin E3 (RvE3), resolvin E4 (RvE4), aspirin-triggered RvE1 (AT-RvE1), AT-RvE2, and AT-RvE3, and further optionally wherein the D series resolvin selected from the group consisting of resolvin D1 (RvD1), resolvin D2 (RvD2), resolvin D3 (RvD3), resolvin D4 (RvD4), resolvin D5 (RvD5), resolvin D6 (RvD6), aspirin-triggered resolvin D1 (AT-RvD1), AT-RvD2, AT-RvD3, AT-RvD4, AT-RvD5, and AT-RvD6. In embodiments, the resolvin is RvE1, RvD1, or RvD2.

In embodiments, A and B are each independently an E series resolvin selected from the group consisting of resolvin E1 (RvE1), resolvin E2 (RvE2), resolvin E3 (RvE3), resolvin E4 (RvE4), aspirin-triggered RvE1 (AT-RvE1), AT-RvE2, and AT-RvE3.

In embodiments, A and B are each independently a D series resolvin selected from the group consisting of resolvin D1 (RvD1), resolvin D2 (RvD2), resolvin D3 (RvD3), resolvin D4 (RvD4), resolvin D5 (RvD5), resolvin D6

(RvD6), protectin D1, protectin DX, aspirin-triggered resolvin D1 (AT-RvD1), AT-RvD2, AT-RvD3, AT-RvD4, AT-RvD5, AT-RvD6, and AT protectin D1

In embodiments, M is selected from magnesium ($Mg^{2+}$) or calcium ($Ca^{2+}$). In embodiments, $R^1$ and $R^2$ are each independently —$(CH_2)_3$—$Y^1$, and —$(CH_2)_4$—$Y^2$, and $Y^1$ and $Y^2$ are each selected from a positively charged primary amine, a positively charged secondary amine, a positively charged tertiary amine, and a positively charged guanidine. In embodiments, $X^1$ and $X^2$ are each H.

In embodiments, $R^1$ and $R^2$ are each —$(CH_2)_4$—$Y^2$ and $Y^2$ is —$NH_3^+$ In embodiments, A and B are the same.

In embodiments, M is magnesium ($Mg^{2+}$), $R^1$ and $R^2$ are each —$(CH_2)_4$—$Y^2$ and $Y^2$ is —$NH_3^+$, $X^1$ and $X^2$ are each H, and A and B are RvE1, which compound is referred to as bis RvE1 Mg-di-lysinate (Compound 1).

In embodiments, M is magnesium ($Mg^{2+}$), $R^1$ and $R^2$ are each —$(CH_2)_4$—$Y^2$ and $Y^2$ is —$NH_3^+$, $X^1$ and $X^2$ are each H, and A and B are RvD1, which compound is referred to as bis RvD1 Mg-di-lysinate.

In embodiments, M is magnesium ($Mg^{2+}$), $R^1$ and $R^2$ are each —$(CH_2)_4$—$Y^2$ and $Y^2$ is —$NH_3^+$, $X^1$ and $X^2$ are each H, and A and B are RvD2, which compound is referred to as bis RvD2 Mg-di-lysinate.

In embodiments of any of the foregoing methods, the cancer is a brain cancer, breast cancer, bladder cancer, colorectal cancer, gastric cancer, lung cancer, ovarian cancer, pancreatic cancer, prostate cancer, esophageal cancer, head and neck cancer, liver cancer, melanoma, renal cell carcinoma, and sarcoma. In embodiments, the cancer is brain cancer, breast cancer, colorectal cancer, lung cancer, ovarian cancer, or pancreatic cancer. In embodiments, the cancer is brain cancer is a glioblastoma. In embodiments, the breast cancer is a triple negative breast cancer. In embodiments, the skin cancer is a melanoma. In embodiments, the pancreatic cancer is a pancreatic adenocarcinoma. In embodiments, the colorectal cancer is a colorectal adenocarcinoma.

The method may also include where the cancer is selected from brain cancer, colorectal cancer, gastric cancer, liver cancer, lung cancer, ovarian cancer, pancreatic cancer, or skin cancer. In embodiments, the cancer is brain cancer, colorectal cancer, lung cancer, or pancreatic cancer.

The method may also include where the cancer is a metastatic cancer.

The method may also include where the cancer is a local, regional, or metastatic cancer.

In embodiments, the method comprises administering the pharmaceutical composition less than daily (LTD), optionally every two days (Q2D), every three days (Q3D), every six days (Q6D), every seven days (Q7D), every fourteen days (Q14D), every twenty-one days (Q21D), or every twenty-eight days (Q28D). In embodiments, LTD administration may be at weekly intervals, for example every two weeks (Q14D), every three weeks (Q21D), or every four weeks (Q28D).

In embodiments, the resolvin or its salt is administered in a dosing regimen of once every three days (Q3D), or once every six days (Q6D), or once every seven days (Q7D).

In embodiments, the resolvin is administered orally or parenterally, optionally wherein the parenteral administration is subcutaneous, intraperitoneal, intramuscular, or intravenous. In embodiments, the resolvin is administered by inhalation. In embodiments, the resolvin is administered by a sublingual route.

In embodiments, the method comprises administering the resolvin, or a salt thereof, as an adjuvant or neoadjuvant to surgery, optionally wherein the surgery is curative surgery or debulking surgery.

In embodiments, the method comprises administering the resolvin, or a salt thereof, as an adjuvant or neoadjuvant to radiation therapy, optionally wherein the radiation therapy is curative or palliative.

In embodiments, the method comprises administering the resolvin, or a salt thereof, in combination with one or more additional therapeutic agents, such as chemotherapy, targeted therapy, immunotherapy, hormone therapy, CAR T cell therapy, gene therapy, or microbiome therapy. In embodiments, the one or more additional therapeutic agents is an antimetabolite, a DNA alkylator, a DNA binder or cleaver, a tubulin or microtubule inhibitor, a DNA topoisomerase inhibitor, an angiogenesis inhibitor, a proteasome inhibitor, a CDK inhibitor, a tyrosine kinase inhibitor, or an immunotherapy agent.

In embodiments, the one or more additional therapeutic agents is gemcitabine or cisplatin.

In embodiments, the one or more additional therapeutic agents is an immune checkpoint inhibitor. In embodiments, the immune checkpoint inhibitor is an anti PD-1 antibody, an anti-PD-2 antibody, an anti-CTLA4 antibody, an anti-PD-L1 antibody, an anti-PD-L2 antibody, or a LAG-3 inhibitor. In embodiments, the immune checkpoint inhibitor is pembrolizumab, nivolumab, atezolizumab, avelumab, durvalumab, cemiplimab, ipilimumab or tremelimumab.

In embodiments of the combination therapies described herein, the method comprises administering the resolvin, or a salt thereof, in combination with an immune checkpoint inhibitor, or a combination of two or more immune checkpoint inhibitors, and one or more additional therapeutic agents, such as chemotherapy, targeted therapy, hormone therapy, CAR T cell therapy, gene therapy, or microbiome therapy.

The method may also include where the cancer is pancreatic cancer and the one or more additional therapeutic agents is a combination of an anti-PD1 antibody or anti-PD-L1 antibody and an anti-CTLA4 antibody or a combination of an anti-PD1 antibody or anti-PD-L1 antibody and a LAG-3 inhibitor, or any combination thereof. In embodiments, the method comprises administering the resolvin, or a salt thereof, in combination with an anti-PD1 antibody or anti-CTLA4 antibody, or in combination with both an anti-PD1 antibody or anti-CTLA4 antibody and gemcitabine, wherein the cancer is pancreatic cancer. The method may also include where the cancer is pancreatic cancer and the one or more additional therapies includes a chemotherapy or targeted therapy regimen selected from the group consisting of FOLFIRINOX, gemcitabine with or without nab-paclitaxel, a PARP inhibitor, and capecitabine.

The method may also include where the cancer is lung cancer and one or more additional therapies is an immune checkpoint inhibitor selected from the group consisting of an anti-PD1 antibody, an anti-PD-L1 antibody, anti-CTLA4 antibody, an anti-CD47 antibody, and a LAG-3 inhibitor, or any combination thereof. In embodiments, the method comprises administering the resolvin, or a salt thereof, in combination with an anti-PD1 antibody or anti-CTLA4 antibody, or in combination with cisplatin, wherein the cancer is lung cancer. The method may also include where the cancer is lung cancer and the one or more additional therapies includes a chemotherapy or targeted therapy regimen including one or more of carboplatin, etoposide, cisplatin, lurbinectedin and irinotecan.

The method may also include where the cancer is colon cancer and the one or more additional therapies is selected from the group consisting of an anti-PD1 antibody, an anti-PD-L1 antibody, anti-CTLA4 antibody, an anti-CD47 antibody, and a LAG-3 inhibitor, or any combination thereof. In embodiments, the method comprises administering the resolvin, or a salt thereof, in combination with an anti-PD1 antibody, an anti-CTLA4, or an anti-CD47 antibody, wherein the cancer is colon cancer. The method may also include where the cancer is colon cancer and the one or more additional therapies includes a chemotherapy or targeted therapy regimen including one or more of bevacizumab, FOLFIRI, and trifluridine plus tipiracil.

The method may also include where the cancer is melanoma and the one or more additional therapies is an immune checkpoint inhibitor selected from the group consisting of an anti-PD1 antibody, an anti-PD-L1 antibody, anti-CTLA4 antibody, an anti-CD47 antibody, and a LAG-3 inhibitor, or any combination thereof. In embodiments, the method comprises administering the resolvin, or a salt thereof, in combination with an anti-PD1 antibody, an anti-CTLA4, or a LAG-3 inhibitor, wherein the cancer is melanoma. The method may also include where the cancer is melanoma and the one or more additional therapies is a chemotherapy or targeted therapy regimen including one or more of binimetinib plus encorafenib, vemurafenib plus cobimetinib, and dabrafenib plus trametinib. Other technical features may be readily apparent to one skilled in the art from the following figures, descriptions, and claims.

The disclosure also provides for the use of a pharmaceutical composition comprising a resolvin, or a salt thereof, in a method for treating cancer in a subject, wherein the composition is adapted for administration less than once daily, optionally in combination with an immune checkpoint inhibitor.

In one aspect, use of a pharmaceutical composition includes a resolvin, or a salt thereof, in a method for treating cancer in a subject, where the composition is adapted for administration less than once daily (LTD), optionally where the method includes administering the resolvin, or a salt thereof, in combination with one or more additional therapeutic agents, or one or more additional therapies, such as surgery, chemotherapy, radiation therapy, targeted therapy, immunotherapy, hormone therapy, CAR T cell therapy, gene therapy, or microbiome therapy. In embodiments, the one or more additional therapeutic agents is an immune checkpoint inhibitor (ICI) or a combination of two or more ICI's. The use may also include where the immune checkpoint inhibitor is an anti PD-1 antibody, an anti-PD-2 antibody, an anti-CTLA4 antibody, an anti-PD-L1 antibody, an anti-PD-L2 antibody, an anti-CD47 antibody, or a LAG-3 inhibitor, or any combination thereof; optionally where the immune checkpoint inhibitor is pembrolizumab, nivolumab, atezolizumab, avelumab, durvalumab, cemiplimab, ipilimumab, tremelimumab, magrolimab, or relatlimab.

In embodiments of any of the foregoing methods, the subject is a human subject.

Other technical features may be readily apparent to one skilled in the art from the following figures, descriptions, and claims.

DETAILED DESCRIPTION

Figure 1A:
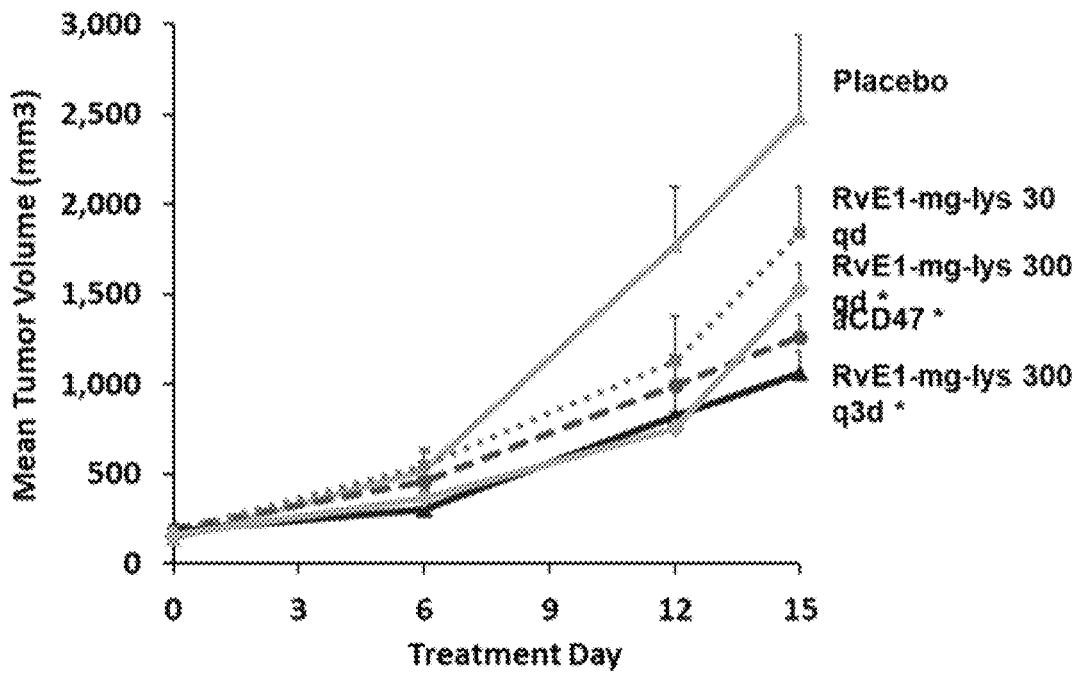
FIG. 1A is a line graph showing tumor volume over time (Day 15 vs Day 0) for bis RvE1 Mg-di-lysinate in the MC38 model of colorectal cancer.

The present invention relates to compositions comprising a resolvin, or a salt thereof, for use in the treatment of cancer. Despite their potential anti-tumor effects, translation of resolvins into the clinic has been hampered, in part, by expectations that their rapid clearance would restrict their bioavailability. Resolvins are quickly cleared following intravenous or subcutaneous administration, exhibiting a serum half-life of less than one hour due to their rapid metabolic inactivation, which was first elucidated by Arita et al., *J. Biol. Chem.* 281, 32 (2006): 22847-54. In order to increase bioavailability, prior studies showing anti-cancer efficacy utilized a continuous or daily dosing regimen such as administration by a mini-osmotic pump or a daily regimen using IP injection, which generally has a rate of absorption that is one half to one-fourth as rapid as IV administration. Al Shoyaib et al. *Pharmaceut.l Res.* 37, 112. 23 Dec. 2019. Other studies utilized the resolvin as a chemopreventive agent, for example by administering the resolvin before or at the same time as tumor cell injection in murine xenograft models. The compositions and methods described here are based, in part, on unexpected findings of efficacy for resolvins and salts of resolvins administered once every six or seven days (Q6D or Q7D). The invention further provides methods relating to combination therapy with resolvins and immune checkpoint inhibitors, based on unexpected findings of efficacy.

Continuous or daily regimens are difficult to translate into the clinic for cancer patients. Daily dosing, whether by the oral, subcutaneous or other routes of administration, places a significant burden on patients, and has been shown to have lower adherence compared to less frequent administration, such as weekly dosing. Weeda et al., *Int J Clin Pract.* 2021 September; 75(9):e14060; Hohneker et al., *J Oncol Pract.* 2011; 7:65-67. Despite the extensive use of weekly (Q7D) dosing for cancer therapeutic agents, this approach has not been reported or deemed feasible with resolvins.

The present invention advantageously provides methods and compositions for the treatment or prevention of cancer using resolvins administered in therapeutic regimens at less than daily (LTD) dosing and by a non-continuous route of administration, such as subcutaneous, intravenous, oral, inhalable or sublingual administration. In embodiments, the resolvin is administered LTD, optionally every two days (Q2D), every three days (Q3D), every six days (Q6D), every seven days (Q7D) or even less frequently such as once every two weeks (Q14D) or once every four weeks (Q28D). The compositions and methods described here are based, in part, on unexpected findings of efficacy for resolvins and salts of resolvins administered by a non-continuous route, and in certain embodiments at less than daily (LTD) dosing. The invention further provides methods relating to combination therapy with resolvins, which are described in the following sections. In embodiments, the invention provides methods of treating cancer by administering a resolvin, or its salt, in combination with immune checkpoint inhibitors.

In embodiments of the compositions and methods described here, the resolvin is in the form of a simple salt, such as a sodium, potassium, or magnesium salt. In embodiments, the resolvin is in the form of a salt described by a compound of Formula I-IV. In embodiments, the disclosure provides a pharmaceutical composition comprising a compound of Formula IV which is a magnesium L-lysinate bis resolvin E1, a magnesium L-lysinate bis resolvin D1, or a magnesium L-lysinate bis resolvin D2, for use in a method of treating cancer as described herein.

In embodiments, the methods of treating cancer described here comprise administering a pharmaceutical composition comprising a compound of Formula IV to a human subject in need of treatment for cancer. In embodiments, the compound of Formula IV is a mono or bis resolvin magnesium, calcium, or zinc di-lysinate (M-lys-lys, or M-di-lysinate) compound selected from the group consisting of RvE1 M-lys-lys, RvE2 M-lys-lys, RvE3 M-lys-lys, RvE4 M-lys-lys, AT-RvE1 M-lys-lys, AT-RvE2 M-lys-lys, and AT-RvE3 M-lys-lys. In embodiments, the compound of Formula IV is a mono or bis RvE1 Mg-lys-lys or a mono or bis AT-RvE1 Mg-lys-lys.

In embodiments, the methods of treating cancer described here comprise administering a pharmaceutical composition comprising a lysyl-lysine dipeptide of Formula I where A and B are the same and are selected from an E or D series resolvin. In embodiments, the E series resolvin is selected from RvE1, RvE2, RvE3, RvE4, AT-RvE1, AT-RvE2, and AT-RvE3. In embodiments, the D series resolvin is selected from RvD1, RvD2, RvD3, RvD4, RvD5, RvD6, AT-RvD1, AT-RvD2, AT-RvD3, AT-RvD4, AT-RvD5, and AT-RvD6. In embodiments, the compound is a bis salt of the resolvin. In embodiments, the compound is selected from the group consisting of mono or bis RvE1 lysyl lysine, mono or bis AT-RvE1 lysyl lysine, mono or bis RvE2 lysyl lysine, mono or bis AT-RvE2 lysyl lysine, mono or bis RvE3 lysyl lysine, mono or bis AT-RvE3 lysyl lysine, and mono or bis RvE4 lysyl lysine.

In embodiments the methods of treating cancer described here comprise administering a pharmaceutical composition comprising a linear lysyl-lysine dipeptide of Formula III where A and B are the same and are selected from an E or D series resolvin. In embodiments, the E series resolvin is selected from RvE1, RvE2, RvE3, RvE4, AT-RvE1, AT-RvE2, and AT-RvE3. In embodiments, the D series resolvin is selected from RvD1, RvD2, RvD3, RvD4, RvD5, RvD6, AT-RvD1, AT-RvD2, AT-RvD3, AT-RvD4, AT-RvD5, and AT-RvD6. In embodiments, the compound is a bis salt of the resolvin. In embodiments, the compound is selected from the group consisting of mono or bis RvE1 linear lysyl lysine, mono or bis AT-RvE1 linear lysyl lysine, mono or bis RvE2 linear lysyl lysine, mono or bis AT-RvE2 linear lysyl lysine, mono or bis RvE3 linear lysyl lysine, and mono or bis AT-RvE3 linear lysyl lysine.

In embodiments, the methods of treating cancer described here comprise administering a pharmaceutical composition comprising a compound selected from a magnesium, calcium, or zinc di-lysinate of Formula IV where A and B are the same and are selected from an E or D series resolvin. In embodiments, the E series resolvin is selected from RvE1, RvE2, RvE3, RvE4, AT-RvE1, AT-RvE2, and AT-RvE3. In embodiments, the D series resolvin is selected from RvD1, RvD2, RvD3, RvD4, RvD5, RvD6, AT-RvD1, AT-RvD2, AT-RvD3, AT-RvD4, AT-RvD5, and AT-RvD6. In embodiments, the compound is a bis salt of the resolvin. In embodiments, the compound is selected from the group consisting of mono or bis RvE1 Mg-di-lysinate, mono or bis AT-RvE1 Mg-di-lysinate, mono or bis RvE2 Mg-di-lysinate, mono or bis AT-RvE2 Mg-di-lysinate, mono or bis RvE3 Mg-di-lysinate, mono or bis AT-RvE3 Mg-di-lysinate, and mono or bis RvE4 Mg-di-lysinate.

In the context of any of the methods of the present invention, the subject may be a human or a non-human mammal. The non-human mammal may be, for example, a non-human primate, a dog, cat, a rodent (e.g., a mouse, a rat, a rabbit), a horse, a cow, a sheep, a goat, or any other non-human mammal. Preferably, the subject is a human. The term "patient" refers to a human subject.

In embodiments, the subject is a human subject. In one embodiment, the human is an adult human, a pediatric human, or a geriatric human, as those terms are understood by the medical practitioner, for example as defined by the U.S. Food and Drug Administration.

As used herein, the term "pharmaceutically acceptable salt," refers to a pharmaceutically acceptable base addition salt which are those salts which retain the biological effectiveness and properties of the free acid counterions and which are not biologically or otherwise undesirable compared to the free acid. These salts are prepared from addition of an inorganic base or an organic base to the free acid. Illustrative salts include, but are not limited to, salts derived from inorganic bases include, but are not limited to, the sodium, potassium, lithium, ammonium, calcium, magnesium, iron, zinc, copper, manganese, and aluminum salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, trimethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, and polyamine resins.

The term "polymorph" in the present disclosure refers to a solid crystalline form of a compound described here. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

The term "hydrate" in the present disclosure refers to a compound described here further including a stoichiometric or non-stoichiometric amount of water bound by non-covalent intermolecular forces.

The term "solvate" or "pharmaceutically acceptable solvate," in the present disclosure refers to a solvate formed from the association of one or more solvent molecules to one of the compounds disclosed herein. The term solvate includes hydrates (e.g., hemi-hydrate, mono-hydrate, dihydrate, trihydrate, tetrahydrate, and the like). In certain embodiments, the solvate is a form of salt bound by a non-covalent bond to another molecule (such as a polar solvent). Such solvates are typically crystalline solids having a substantially fixed molar ratio of solute and solvent. When the solvent is water, the solvate formed is a hydrate. Example hydrates include hemihydrates, mono hydrates, dihydrates, etc.

In embodiments, the invention provides a crystalline form of a compound described herein. In one embodiment, the invention provides a polymorph of an ionic salt described herein.

Certain compounds of the present disclosure possess asymmetric carbon atoms (optical centers) or double bonds; the racemates, diastereomer, geometric isomers, regioisomers and individual isomers (e.g., separate enantiomers) are all intended to be encompassed within the scope of the present disclosure. In embodiments, the compounds of the present disclosure are a particular enantiomer, anomer, or diastereomer substantially free of other forms.

Methods of Treating Cancer

The present disclosure provides methods for treating cancer in a subject in need of such treatment. In embodiments, the methods comprising administering to the subject a pharmaceutical composition comprising a resolvin, or a salt thereof, in a dosing regimen of once daily or less than daily, for example one or more times per week, such as once every two days (Q2D), once every three days (Q3D), once every six days (Q6D) or once every seven days (Q7D). In embodiments, the dosing regimen may be at weekly intervals, for example once every two weeks (Q14D), once every three weeks (Q21D) or once every four weeks (Q28D). In accordance with the methods described here, the resolvin, or its salt, is administered either alone as monotherapy, or in combination therapy with one or more additional therapeutic agents. In embodiments, the combination therapy is an adjunctive therapy, for example as an adjunct to chemotherapy, targeted therapy, immunotherapy, hormone therapy, CAR T cell therapy, gene therapy, or microbiome therapy. In embodiments, the combination therapy is an immune checkpoint inhibitor therapy, as discussed in more detail below. In embodiments, the combination therapy is an adjuvant or neoadjuvant therapy to surgery or radiation therapy. In embodiments, the composition may be administered as first line, second line, third line or palliative therapy, alone or in combination with other therapies, for example, surgery, radiation therapy, chemotherapy, targeted therapy, immunotherapy, hormone therapy, CAR T cell therapy, gene therapy, or microbiome therapy. The terms "therapy" and "therapies" refer to any method, protocol and/or agent that can be used in the treatment or management of the cancer. Combination therapies are described in more detail in the following sections.

In the context of the methods described here, the term "treating" may refer to the amelioration or stabilization of one or more clinical symptoms associated with the cancer being treated. In embodiments, treating leads to the elimination of a clinical symptom of the cancer being treated, however, elimination is not required. In embodiments, severity of the symptom is decreased. In the context of cancer, such symptoms may include clinical markers of severity or progression including size of a solid tumor, amount of growth factors or other biomarkers secreted by a solid tumor, tumor vascularization, tumor metastasis, or number of metastases. Accordingly, treating cancer according to the methods described here can result in a reduction in size or volume of a tumor, also referred to as tumor regression; a decrease in the number of tumors; or a decrease in the number of metastatic lesions in other tissues or organs distant from the primary tumor site. Such symptoms may also include cancer cachexia or pain. Accordingly, treating cancer according to the methods described here can result in a reduction in cancer cachexia or pain, wherein the reduction in cachexia or pain is due to the administration of a resolvin, or its salt, as described herein. In embodiments, "treating" cancer according to the methods described here results in increased overall survival and/or increased progression free survival in the subject being treated. In the context of the present disclosure, the term "treating" is not meant to encompass the amelioration or stabilization of clinical symptoms that are not associated with the cancer being treated, and instead, for example, are associated with a treatment modality, such as a side effect or adverse event related to another therapy such as radiation therapy or chemotherapy, unless explicitly stated. In addition, the term "treating" is not intended to encompass prevention, or the administration of a resolvin, or its salt, prior to diagnosis of a cancer in the subject being treated.

In embodiments, the present invention provides methods for the amelioration of an adverse event or side effect of chemotherapy, targeted therapy, immunotherapy, or radiation therapy, for example, gastrointestinal toxicities such as oral or gastrointestinal mucositis, colitis, enteritis, gastritis, nausea, vomiting, and diarrhea, cardiovascular toxicities such as cardiomyopathy, myocardial ischemia, pericarditis, myocarditis, valvular heart disease, arrhythmia, congestive heart failure, hypertension, coronary, cerebral, and peripheral vascular events, or congestive heart failure, dermatological toxicities such as pruritis or severe rash, hepatotoxicities, pulmonary toxicities such as pulmonary hypertension and pneumonitis, endocrinopathies such as hypothyroidism, hyperthyroidism, and hypophysitis, neurotoxicities such as such as Guillain-Barre syndrome, myasthenia gravis, posterior reversible encephalopathy syndrome, aseptic meningitis, enteric neuropathy, transverse myelitis, pancerebellitis, autoimmune encephalitis, and cranial and peripheral neuropathies, or other side effects such as pancreatitis, acute kidney injury, and cytokine release syndrome, the methods comprising administering a resolvin, or its salt, to a subject that is undergoing or will be undergoing chemotherapy, targeted therapy, immunotherapy, or radiation therapy, wherein the resolvin is effective to mitigate or prevent an adverse event or side effect of the chemotherapy, targeted therapy, immunotherapy, or radiation therapy.

In accordance with the methods described here, a therapeutically effective amount of the resolvin, or a salt thereof, is administered to the subject in need of therapy. The therapeutically effective amount is an amount or dose of the resolvin, or its salt, sufficient to treat the cancer, or sufficient to achieve a desired therapeutic outcome, for example, the amelioration or stabilization of one or more biomarkers of disease progression or one or more clinical symptoms.

In embodiments, the therapeutically effective amount comprises from about 0.1 mg to 100 mg resolvin per dose, preferably between about 0.5 mg and 20 mg, or between about 1 mg and 10 mg resolvin per dose. When administered using continuous dosing, the therapeutically effective amount comprises from about 0.1 mg to 100 mg resolvin per day or per week or per month, preferably between about 0.5 mg and 20 mg per day or per week or per month, or between about 1 mg and 10 mg resolvin per day or per week or per month.

A dose of the resolvin, or its salt, is administered in accordance with a therapeutic regimen as described herein, for example once daily or less than daily (LTD). In embodiments, the regimen may comprise dosing one or more times per week, such as every two days (Q2D), every three days (Q3D), every six days (Q6D) or every seven days (Q7D). In embodiments, the regimen may comprise dosing once or twice a month, such as every two to four weeks. In embodiments, the regimen comprises dosing every 1, 2, 4, 6, or 8 weeks. It is understood that a regimen may include successive periods of different dosing frequency, for example QD for a period of time followed by an LTD dosing regimen, such as Q2D, Q3D, Q6D, Q7D or less frequently than Q7D, or alternatively. Q2D, Q3D, Q6D or Q7D for a period of time followed by dosing less frequently, such as every 2, 4, 6, or 8 weeks, for a second period of time, or alternatively, any LTD dosing regimen for a period of time followed by a dosing regimen of lesser or greater frequency.

In embodiments of the methods described here, the subject in need of treatment is one presenting with a solid tumor cancer requiring one or more of surgical resection or debulking, radiation therapy, or pharmacological therapy in the form of chemotherapy, targeted therapy, immunotherapy, hormone therapy, CAR T cell therapy, gene therapy, or microbiome therapy, or any combination of the foregoing. In embodiments, the pharmaceutical composition comprising a resolvin, or a salt thereof, is administered concurrent with, prior to, or following surgical resection or debulking. In embodiments, the pharmaceutical composition is administered concurrent with, prior to, or following radiation therapy, chemotherapy, targeted therapy or immunotherapy.

In embodiments, the pharmaceutical composition comprising a resolvin, or a salt thereof, is administered in accordance with a therapeutic regimen comprising once per day or less than daily (LTD) dosing of the resolvin. In embodiments, the therapeutic regimen comprises administering one or more doses of a resolvin, or a salt thereof, given daily or less than daily, for example one or more times per week, such as every two days (Q2D), every three days (Q3D), every six days (Q6D) or every seven days (Q7D), prior to surgery or radiation therapy, on the same day as surgery or radiation therapy, and/or following surgery or radiation therapy but before the initiation of chemotherapy, targeted therapy or immunotherapy.

In embodiments, the pharmaceutical composition is administered as part of a maintenance therapy every two days (Q2D), every three days (Q3D), every six days (Q6D) or every seven days (Q7D) using intravenous, subcutaneous, intraperitoneal, or other routes of administration during clinic visits; or taken outside of the clinic using routes of administration that can be self-administered by the patient (e.g., subcutaneous, oral, sublingual, inhalable, and topical).

In embodiments, the pharmaceutical composition comprising a resolvin, or a salt thereof, may be administered by any suitable route of administration, including subcutaneous, intravenous, intramuscular, oral, transdermal, sublingual, topical, or by inhalation. In embodiments, administration is by a subcutaneous or intramuscular route. In embodiments, the oral dosage form may be in the form of a tablet, capsule, powder, solution, suspension, or emulsion. In embodiments of subcutaneous dosing, the dosage form may be a liquid, including an aqueous liquid, and the volume of a dose may be between 0.2 mL and 5 mL, preferably between 0.5 mL and 2 mL and preferably no greater than 1 mL. In embodiments of intravenous dosing, a dose may be delivered in the form of a bolus or by infusion, for example pump infusion or drip infusion.

In embodiments, the methods described here may encompass treating a primary cancer or a metastatic cancer. Examples of cancers that may treated include, but are not limited to, cancer of the bladder, blood, bone, bone marrow, brain, breast, colon, esophagus, gastrointestinal, gum, head, kidney, liver, lung, nasopharynx, neck, ovary, pancreas, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lympho epithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromo-phobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; non encapsulating sclerosing carcinoma; adrenal cortical carcinoma; endometroid carcinoma; skin appendage carcinoma; apocrine adenocarcinoma; sebaceous adenocarcinoma; ceruminous; adenocarcinoma; muco epidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; Paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; and roblastoma, malignant; Sertoli cell carcinoma; Leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malign melanoma in giant pigmented nevus; epithelioid cell melanoma; blue nevus, malignant; sarcoma; fibrosarcoma; fibrous histiocytoma, malignant; myosarcoma; liposarcoma; leiomyosarcoma; rhabdomyosarcoma; embryonal rhabdomyosarcoma; alveolar rhabdomyosarcoma; stromal sarcoma; mixed tumor, malignant; Mullerian mixed tumor; nephroblastoma; hepatoblastoma; carcinosarcoma; mesenchymoma, malignant; Brenner tumor, malignant; phyllodestumor, malignant; synovial sarcoma; mesothelioma, malignant; dysgerminoma; embryonal carcinoma; teratoma, malignant; strumaovarii, malignant; choriocarcinoma; mesonephroma, malignant; hemangio sarcoma; hemangioendothelioma, malignant; Kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; Ewing's sarcoma; odontogenic tumor, malignant; ameloblasticodontosarcoma; ameloblastoma, malignant; ameloblasticfibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythron leukemia; lymphosarcoma cell leukemia; myeloid leukemia; basophilic leukemia; eosinophilic leukemia; monocyticleukemia; mast cell leukemia; megakaryoblasticleukemia; myeloid sarcoma; and hairy cell leukemia.

Combination Therapies

In the context of the methods described above, the methods may further comprise administering a pharmaceutical composition comprising a resolvin, or its salt, in combination therapy, for example in combination with one or more additional therapeutic agents, which may be referred to as active pharmaceutical ingredients (API), or one or more additional therapies, such as surgery, chemotherapy, radiation therapy, targeted therapy, immunotherapy, hormone therapy, CAR T cell therapy, gene therapy, or microbiome therapy. In embodiments, administration of the resolvin, or its salt, may be simultaneous, separate, or sequential with respect to the one or more additional APIs or therapies.

As discussed in the examples below, the invention discloses the unexpected finding that resolvins promote anti-tumor immunity mediated through T-cells. This is in contrast to prior studies showing that resolvins inhibit CD8+ infiltration into the tumor microenvironment and CD4+ T-cell activation, chemoattraction, and differentiation into Th1 and TH17 cells, and that resolvins enhance the de novo generation and function of immunosuppressive T regulatory cells ("Tregs"), which are associated with cancer progression and resistance to immune checkpoint inhibitors. Chiurchiu et al. *Sci Transl Med* (2017). In another study in a human papilloma virus (HPV) tumorigenesis as a model, RvD1 modulated the activity of tumor-associated neutrophils (PMN) to reduce tumor progression but did not modify tumor infiltration levels of CD4+ and CD8+ T cells, which play a major role in the antitumour immune response of immune checkpoint inhibitors. Mattoscio et al. *J Exp. Clin. Can. Res.* (2021) 40:129.

Unexpectedly, the results discussed in the examples below show that combination therapy with resolvins and immune checkpoint inhibitors had potent anti-tumor effects. Accordingly, the present invention also provides methods of treating cancer in a subject in need of such treatment where the methods comprising administering to the subject a pharmaceutical composition comprising a resolvin, or a salt thereof, in combination with one or more immune checkpoint inhibitors. In embodiments, the resolvin, or a salt thereof, is administered in combination with PD1 and PDL1 inhibitor, including but not limited to pembrolizumab, nivolumab, atezolizumab, avelumab, durvalumab and cemiplimab; or a CLTA-4 inhibitor, including but not limited to ipilimumab and tremelimumab; or a CD-47 inhibitor including but not limited to magrolimab; or a LAG-3 inhibitor including but not limited to relatlimab and eftilagimod alpha. In the context of combination therapy with immune checkpoint inhibitors, the resolvin may be administered in any suitable dosing regimen. In embodiments, the resolvin is administered once or twice daily, or more frequently or by continuous administration, for example by continuous subcutaneous infusion or by use of depot intramuscular injection administered once every month or two months or three months. In embodiments, the resolvin is administered less than daily (LTD), for example one or more times per week, such as every two days (Q2D), every three days (Q3D), every six days (Q6D) or every seven days (Q7D).

In addition, the present invention discloses that combination therapy with resolvins and immune checkpoint inhibitors (ICIs) provides reduced variability in the therapeutic response. This was unexpected because the efficacy of ICI therapy is highly variable and unpredictable among different cancers and among patients with the same cancer. For example, treatment with a PD-1 inhibitor has an objective response rate (ORR) that varies from almost nonexistent in pancreatic cancer and microsatellite-stable colonic adenocarcinoma to an average of 15%-30% in most other types of cancers. The only cancers where anti-PD-$(L)_1$ treatment has demonstrated ORR greater than 50% include melanoma, Hodgkin lymphoma, squamous-cell carcinoma of the skin, and Merkel cell carcinoma. Accordingly, in embodiments, the invention provides methods of treating cancer by administering a combination therapy regimen comprising a resolvin, or its salt, and an immune checkpoint inhibitor (ICI) or a combination of at least two ICI's (including bi-functional monoclonal antibodies), wherein the method provides an ORR that is at least 20%, 30%, 40%, or 50% greater than the ICI alone or combination of ICE's alone (including bi-functional monoclonal antibodies), or than the ICI in combination with a standard of care therapeutic agent, in the cancer being treated. In embodiments, the cancer being treated is pancreatic cancer, colon cancer, ovarian cancer, lung cancer, hepatocellular carcinoma, gastric cancer, prostate cancer, breast cancer, skin cancer, or brain cancer.

The present invention also discloses that methods comprising combination therapy with resolvins and immune checkpoint inhibitors (ICIs) can enhance therapeutic efficacy compared to standard of care for the ICI alone, or for the ICI in combination with another ICI or a chemotherapy agent or regimen. Use of immunotherapies can be limited by immune-related adverse events (IRAEs), which include immune activation and inflammatory responses against healthy tissues. IRAEs are challenging to predict, diagnose, and treat and can lead to a temporary or permanent cessation of therapy and increased morbidity and mortality. For example, in the setting of metastatic melanoma, the addition of a CTLA-4 antibody to PD-1 blockade is associated with a two-fold increase in the rate of serious IRAEs. The present disclosure provides methods of treating cancer by administering a combination therapy regimen comprising a resolvin, or its salt, and an immune checkpoint inhibitor alone or in combination with other ICIs and/or non-ICI therapies, wherein the method induces fewer IRAEs than the ICI administered alone or in combination with other ICIs and/or non-ICI therapies at their standard doses or enables a reduction in the doses of ICIs to reduce IRAEs while maintaining adequate efficacy.

In embodiments, the invention provides methods of treating cancer which comprise administering a pharmaceutical composition comprising a resolvin, or its salt, in combination with chemotherapy. With respect to chemotherapy, the therapy may be selected from the following groups or any combination of two or more agents within a group or among groups: (i) antimetabolites that include but are not limited to azacitidine, capecitabine, cladribine, clofarabine, CPX-351, cytarabine, decitabine, fludarabine, gemcitabine, methotrexate, nelarabine, pemetrexed, pralatrexate, raltitrexed, trifluridine, Lonsurf; (ii) DNA alkylators that include but are not limited to altretamine, bendamustine, busulfan, carboplatin, carmustine, chlorambucil, cisplatin, cyclophosphamide, dacarbazine, estramustine, fotemustine, ifosfamide, lobaplatin, lomustine, mechlorethamine, melphalan, miriplatin, mitomycin c, nedaplatin, nimustine, oxaliplatin, procarbazine, ranimustine, semustine, streptozotocin, temozolomide, thiotepa, trabectedin, nedaplatin, trofosfamide; (iii) DNA binders or cleavers that include but are not limited to actinomycin d, mithramycin, bleomycin, peplomycin; (iv) tubulin and microtubule inhibitors DNA topoisomerase inhibitors that include but are not limited to cabazitaxel, docetaxel, eribulin, ixabepilone, nab-paclitaxel, paclitaxel, vinblastine, vincristine, vindesine, vinflunine, vinorelbine; and (v) DNA topoisomerase inhibitors that include but are not limited to aclarubicin, amrubicin, belotecan, daunorubicin, doxil, doxorubicin, epirubicin, etoposide, idarubicin, irinotecan, mitoxantrone, nal-iri, pirarubicin, pixantrone, teniposide, topotecan, valrubicin, ingenol. In other embodiments, the chemotherapy may include specific combinations that include but are not limited to FOLFIRINOX, FOLFOX, FOLFIRI, gemcitabine plus nab-paclitaxel, and trifluridine plus tipiracil, with or without targeted therapies and immunotherapies.

In embodiments, the invention provides methods of treating cancer which comprise administering a pharmaceutical composition comprising a resolvin, or its salt, in combination with a targeted therapy. With respect to targeted therapy, the therapy may be selected from the following groups or any combination of two or more agents within a group or among groups: (i) angiogenesis inhibitors including but not limited to angiostatin, apatinib, axitinib, bevacizumab, cabozantinib, carboxyamidotriazole, endostatin, everolimus, itraconazole, lenvatinib, nintedanib, pazopanib, ranibizumab, regorafinib, sorafenib, sunitinib, thrombospondin, matrix metalloproteinase inhibitors, and vandetanib; and (ii) monoclonal antibodies including but not limited to alemtuzumab, trastuzumab, cetuximab and panitumumab; (iii) proteasome inhibitors including but not limited to bortezomib, carfilzomib and ixazomib; (iv) CDK inhibitors including but not limited to palbociclib, ribociclib, abemaciclib, and trilaciclib; and (v) tyrosine kinase inhibitors including but not limited to afatinib, alectinib, brigatinib, bosutinib, crizotinib, dacomitinib, dasatinib, encorafenib, erlotinib, gefitinib, imatinib, lapatinib, lorlatinib, osimertinib, pazopanib, ruxolitinib, sunitinib, and vemurafenib.

In embodiments, the invention provides methods of treating cancer which comprise administering a pharmaceutical composition comprising a resolvin, or its salt, in combination with immunotherapy. With respect to immunotherapy, the therapy may be selected from the following groups or any combination of two or more agents within a group or among groups: (i) PD1 and PDL1 inhibitors including but not limited to pembrolizumab, nivolumab, atezolizumab, avelumab, durvalumab and cemiplimab; (II) CLTA-4 inhibitors including but not limited to ipilimumab and tremelimumab; (iii) costimulatory or agonist antibodies including CD137 agonists (e.g., utomilumab, urelumab), CD278 agonists, CD357 agonists, CD70 agonists (e.g., cusatuzumab), CD27 agonists (varlilumab), OX40 (CD134) agonists, and CD40 agonists; (iv) co-inhibitory or antagonist antibodies including but not limited to B7-H5 inhibitors, CCR4

(CD194) inhibitors (e.g., mogamulizumab), B7-H3 (CD276) inhibitors, TIM-3 inhibitors (e.g., oleclumab), LAG-3 (CD223) inhibitors (e.g., relatlimab, eftilagimod alpha), KIR (2DL1-3) inhibitors (e.g., lirilumab), IDO-1,2 inhibitors (e.g., indoximod, epacadostat), TIGIT inhibitors (e.g., tislelizumab), A2aR inhibitors (e.g., ciforadenant), transforming growth factor R inhibitors (e.g., galunisertib), CD47 inhibitors (e.g., magrolimab), CD28 inhibitors, CD73 inhibitors (e.g., oleclumab), and (v) other pathways including but not limited to toll-like receptors (e.g., to polyinosinic-polycytidylic acid-poly-L-lysine carboxymethylcellulose, lefitolimod and rintatolimod), Interleukin 2 receptors, arginase inhibitors, oncolytic peptides, and interleukin 10 (e.g., pegilodecakin).

In embodiments, the invention provides methods of treating cancer which comprise administering a pharmaceutical composition comprising a resolvin, or its salt, in combination with hormone therapy. With respect to hormone therapy, the therapy may be selected from the following groups or any combination of two or more agents within a group or among groups: (i) aromatase inhibitors including but not limited to anastrozole, letrozole, and exemestane; (ii) selective estrogen receptor modulators including but not limited to tamoxifen, raloxifene, and toremifene; (iii) selective estrogen receptor degrader including but not limited to fulvestrant; (iv) androgen deprivation therapy including but not limited to LHRH agonists such as leuprolide, goserelin, triptorelin and histrelin; and (v) androgen blockers including but not limited to enzalutamide, apalutamide, and darolutamide.

With respect to the foregoing therapeutic regimens, the combination therapy may also include surgery or radiation combined with any pharmacologic therapy, or any combination of pharmacologic therapies including chemotherapy, targeted therapy, immunotherapy, hormone therapy, CAR T cell therapy, gene therapy, or microbiome therapy.

In embodiments, the combination therapy may also comprise one or more additional steroidal or nonsteroidal anti-inflammatory drugs (NSAIDs) such as aspirin, naproxyn, or celecoxib; or selective cytokine or eicosanoid blockade via use of monoclonal antibodies or small molecule immunomodulators such as Janus kinase inhibitors.

In embodiments for the treatment of pancreatic cancer, the pharmaceutical composition comprising a resolvin, or its salt, may be administered in combination with FOLFIRINOX (a combination therapy consisting of 5-fluorouracil, leucovorin, irinotecan and oxaliplatin), gemcitabine plus albumin-bound paclitaxel (nab-paclitaxel), gemcitabine plus cisplatin, gemcitabine alone, or any combination thereof; or any other therapeutic regimen that is used in the treatment of pancreatic cancer (see Table 1).

In embodiments for the treatment of colon cancer, the pharmaceutical composition comprising a resolvin, or its salt, may be administered in combination with FOLFOX (a combination therapy consisting of 5-fluorouracil, leucovorin, and oxaliplatin) with or without an anti-angiogenic drug such as bevacizumab or an EGFR inhibitor such as cetuximab, FOLFIRI (a combination therapy consisting of leucovorin, 5-fluorouracil, irinotecan) with or without an anti-angiogenic drug such as bevacizumab or an EGFR inhibitor such as cetuximab, trifluridine plus tipiracil, regorafenib, or any combination thereof; or any other therapeutic regimen that is used in the treatment of colon cancer (see Table 2).

In embodiments for the treatment of ovarian cancer, the pharmaceutical composition comprising a resolvin, or its salt, may be administered in combination with carboplatin plus docetaxel, carboplatin plus paclitaxel, the combination of intraperitoneal cisplatin, intraperitoneal paclitaxel, and intravenous paclitaxel, liposomal doxorubicin plus carboplatin, a PARP inhibitor such as niraparib, olaparib or rubaparib, or any combination thereof; or any other therapeutic regimen that is used in the treatment of ovarian cancer (see Table 3).

In embodiments for the treatment of lung cancer, the pharmaceutical composition comprising a resolvin, or its salt, may be administered in combination with atezolizumab, bevacizumab, carboplatin, cisplatin, crizotinib, dabrafenib, docetaxel, durvalumab, erlotinib, etoposide, gemcitabine, irinotecan, osimertinib, nab-paclitaxel, paclitaxel, pembrolizumab, pemetrexed, topotecan, trametinib, vinorelbine, or any combination thereof; or any other therapeutic regimen that is used in the treatment of lung cancer (see Table 4).

In embodiments for the treatment of hepatocellular carcinoma, the pharmaceutical composition comprising a resolvin, or its salt, may be administered in combination with atezolizumab plus bevacizumab, tyrosine kinase inhibitors (e.g., sorafenib, regorafenib), cabozantinib, or any combination thereof; or any other therapeutic regimen that is used in the treatment of hepatocellular carcinoma (see Table 5).

In embodiments for the treatment of gastric cancer, the pharmaceutical composition comprising a resolvin, or its salt, may be administered in combination with 5-fluorouracil, folinic acid, capecitabine, carboplatin, cisplatin, docetaxel, epirubicin, irinotecan, oxaliplatin, paclitaxel, trifluridine plus tipiracil, nivolumab, pembrolizumab, trastuzumab, Fam-trastuzumab deruxtecan, ramucirumab, larotrectinib, doxorubicin hydrochloride, entrectinib, or any combination thereof; or any other therapeutic regimen that is used in the treatment of gastric cancer (see Table 6).

In embodiments for the treatment of melanoma, the pharmaceutical composition comprising a resolvin, or its salt, may be administered in combination with nivolumab, pembrolizumab, ipilimumab with nivolumab or pembrolizumab, nivolumab combined with relatlimab; or any other therapeutic regimen that is used in the treatment of melanoma (see Table 7).

In embodiments for the treatment of brain cancer, the pharmaceutical composition comprising a resolvin, or its salt, may be administered in combination with bevacizumab plus temozolomide, temozolomide plus radiation therapy, or any combination thereof; or any other therapeutic regimen that is used in the treatment of brain cancer (see Table 8).

In embodiments for the treatment of breast cancer, the pharmaceutical composition comprising a resolvin, or its salt, may be administered in combination with abemaciclib, ado-trastuzumab emtansine, alpelisib, anastrozole, capecitabine, eribulin, fam-trastuzumab deruxtecan-nxki, fulvestrant, lapatinib, letrozole, margetuximab, nab-paclitaxel, olaparib, paclitaxel, pertuzumab, palbociclib, pembrolizumab, ribociclib, sacituzumab govitecan, talazoparib, tamoxifen, thp, tucatinib, trastuzumab, or any combination thereof; or any other therapeutic regimen that is used in the treatment of breast cancer (see Table 9).

With respect to the foregoing therapeutic regimens for those drugs administered parenterally in a hospital or outpatient setting, typically on a weekly basis one to four times every 28 days, the pharmaceutical composition may be administered on a weekly basis on the same day that the other drugs are administered or off-cycle when other therapies are not given, or QD, Q2D, Q3D, Q6D, Q7D or less frequently at home in between cycles of the other therapy or as maintenance once the other therapies are terminated. In addition, the pharmaceutical composition when used as neo-adjuvant therapy may be administered one to seven days before surgery or radiation therapy that is given as curative, debulking or palliative therapy and continued QD, Q2D, Q3D, Q6D, Q7D or less frequently at home as monotherapy or in combination with other therapies that are used following surgery or radiation therapy.

With respect to the foregoing therapeutic regimens, the pharmaceutical composition comprising a resolvin, or its salt, is administered QD, Q2D, Q3D, Q6D or Q7D at home or as co-therapy in the clinic if the resolvin regimen overlaps with the regimen of the primary therapy administered in the clinic to optimize patient adherence.

TABLE 1

Exemplary Therapeutic Regimens for Combination Therapy: Pancreatic Cancer

| Primary Therapy | Typical Regimen | Resolvin regimen in combination therapy |
|---|---|---|
| FOLFIRINOX | IV, every 14 days, 12 cycles, up to 24 weeks | Q7D in clinic when given as co-therapy or QD, Q2D, Q3D, Q6D or Q7D at home |
| Gemcitabine + nab-paclitaxel | IV, days 1, 8, 15 every 28-days, 6 cycles, up to 24 weeks | Q7D in clinic when given as co-therapy or QD, Q2D, Q3D, Q6D or Q7D at home |
| Cisplatin + gemcitabine | IV, days 1 and 15 every 28-days, no cycle limit | Q7D in clinic when given as co-therapy or QD, Q2D, Q3D, Q6D or Q7D at home |
| Gemcitabine | IV, days 1, 8, 15 every 28-days, 6 cycles, up to 24 weeks | Q7D in clinic when given as co-therapy or QD, Q2D, Q3D, Q6D or Q7D at home |
| Pembrolizumab | IV, once every 3 or 6 weeks, no limit on duration of therapy | Q7D in clinic when given as co-therapy or QD, Q2D, Q3D, Q6D or Q7D at home |
| Capecitabine (PO) | PO, QD or BID, maintenance | QD, Q2D, Q3D, Q6D or Q7D at home or in clinic |
| PARP inhibitor | PO, QD or BID, maintenance | QD, Q2D, Q3D, Q6D or Q7D at home or in clinic |

TABLE 2

Exemplary Therapeutic Regimens for Combination Therapy: Colon Cancer

| Primary Therapy | Typical Regimen | Resolvin regimen in combination therapy |
|---|---|---|
| FOLFOX + Bevacizumab | IV, Q14D, no cycle limit | Q7D in clinic when given as co-therapy or QD, Q2D, Q3D, Q6D or Q7D at home |
| FOLFIRI + Bevacizumab | IV, Q14D, no cycle limit | Q7D in clinic when given as co-therapy or QD, Q2D, Q3D, Q6D or Q7D at home |
| Pembrolizumab | IV, once every 3 or 6 weeks, no limit on duration of therapy | Q7D in clinic when given as co-therapy or QD, Q2D, Q3D, Q6D or Q7D at home |
| Nivolumab | IV, once every 2 or 4 weeks until it no longer works | Q7D in clinic when given as co-therapy or QD, Q2D, Q3D, Q6D or Q7D at home |
| Trifluridine plus Tipiracil | PO, days 1 through 5 and days 8 through 12, 28-day cycle, no cycle limit | QD, Q2D, Q3D, Q6D or Q7D at home or in clinic |
| Regorafenib | PO, QD for 21 days, 7 days rest, 28-day cycle, no cycle limit | QD, Q2D, Q3D, Q6D or Q7D at home or in clinic |

TABLE 3

Exemplary Therapeutic Regimens for Combination Therapy: Ovarian Cancer

| Primary Therapy | Typical Regimen | Resolvin regimen in combination therapy |
|---|---|---|
| Carboplatin + Docetaxel + Bevacizumab + PARP inhibitor | Carboplatin + Docetaxel: (IV), Q3W or Q7D for 3 weeks every 28 days, up to 6 cycles Bevacizumab (IV): Q3W, no cycle limit; PAPR inhibitor: PO, QD or BID, maintenance | Q7D in clinic when given as co-therapy or QD, Q2D, Q3D, Q6D or Q7D at home |
| Carboplatin + Paclitaxel Bevacizumab + PARP inhibitor | Carboplatin (IV): Q3W every 21 days Paclitaxel (IV): Q3W or Q7D for 3 weeks no cycle limit; Bevacizumab (IV): Q3W, no cycle limit PAPR inhibitor: PO, QD or BID, maintenance | Q7D in clinic when given as co-therapy or QD, Q2D, Q3D, Q6D or Q7D at home |
| IP cisplatin + IP Paclitaxel + IV Paclitaxel | IV Paclitaxel on day 1 over 2 days, IP cisplatin on day 2, IP Paclitaxel on day 8, 21-day cycles for up to 6 cycles | Q7D in clinic when given as co-therapy or QD, Q2D, Q3D, Q6D or Q7D at home |
| Liposomal Doxorubicin + Carboplatin PARP inhibitor | IV, Q4W, 28-day cycle No cycle limit PO, QD or BID, maintenance | Q7D in clinic when given as co-therapy or QD, Q2D, Q3D, Q6D or Q7D at home QD, Q2D, Q3D, Q6D or Q7D at home or in clinic |

TABLE 4

Exemplary Therapeutic Regimens for Combination Therapy: SC Lung Cancer

| Primary Therapy | Typical Regimen | Resolvin regimen in combination therapy |
|---|---|---|
| Carboplatin + etoposide + Atezolizumab | Carboplatin + etoposide (IV), Q3W or Q4W, 28-day cycle, No cycle limit; Atezolizumab (IV), Q3W, 21-day cycle, No cycle limit | Q7D in clinic when given as co-therapy or QD, Q2D, Q3D, Q6D or Q7D at home |
| Cisplatin + etoposide + Atezolizumab | Carboplatin + etoposide (IV), Q3W, 21-day cycle, up to 6 cycles; Atezolizumab (IV), Q3W, 21-day cycle, No cycle limit | Q7D in clinic when given as co-therapy or QD, Q2D, Q3D, Q6D or Q7D at home |
| Lurbinectedin | IV, Q3W, no cycle limit | Q7D in clinic when given as co-therapy or QD, Q2D, Q3D, Q6D or Q7D at home |
| Irinotecan | IV, 5 consecutive days every 21 days, no cycle limit | QD, Q2D, Q3D, Q6D or Q7D at home or in clinic |

TABLE 5

Exemplary Therapeutic Regimens for Combination Therapy: Liver Cancer

| Primary Therapy | Typical Regimen | Resolvin regimen in combination therapy |
|---|---|---|
| Atezolizumab + Bevacizumab | IV, Q3W, 21-day cycle No cycle limit | Q7D in clinic when given as co-therapy or QD, Q2D, Q3D, Q6D or Q7D at home |
| Pembrolizumab | IV, once every 3 or 6 weeks, no limit on duration of therapy | Q7D in clinic when given as co-therapy or QD, Q2D, Q3D, Q6D or Q7D at home |

TABLE 5-continued

Exemplary Therapeutic Regimens for Combination Therapy: Liver Cancer

| Primary Therapy | Typical Regimen | Resolvin regimen in combination therapy |
|---|---|---|
| Pembrolizumab + Lenvatinib | Pembrolizumab (IV), once every 3 or 6 weeks; Lenvatinib (PO), QD; no limit on duration of therapy | Q7D in clinic when given as co-therapy or QD, Q2D, Q3D, Q6D or Q7D at home |
| Sorafenib or regorafenib | PO, QD for 21 days and 7 day rest per 28-day cycle, no cycle limit | QD, Q2D, Q3D, Q6D or Q7D at home or in clinic |
| Cabozantinib | PO, QD, no cycle limit | QD, Q2D, Q3D, Q6D or Q7D at home or in clinic |

TABLE 6

Exemplary Therapeutic Regimens for Combination Therapy: Gastric Cancer

| Primary Therapy | Typical Regimen | Resolvin regimen in combination therapy |
|---|---|---|
| FLOT (Fluorouracil + Leucovorin + Oxaliplatin + Docetaxel) | IV, Q2W, 14-day cycle Typically up to 12 cycles | Q7D in clinic when given as co-therapy or QD, Q2D, Q3D, Q6D or Q7D at home |
| Ramucirumab | IV, Q2W, 14-day cycle no cycle limit | Q7D in clinic when given as co-therapy or QD, Q2D, Q3D, Q6D or Q7D at home |
| Capecitabine + Irinotecan | Irinotecan (IV) given on day one, every 21 days; Capecitabine (PO) twice daily from day 2-15, every 21 days. No cycle limit | Q7D in clinic when given as co-therapy or QD, Q2D, Q3D, Q6D or Q7D at home |
| Pembrolizumab | IV, once every 3 or 6 weeks, no limit on duration of therapy | Q7D in clinic when given as co-therapy or QD, Q2D, Q3D, Q6D or Q7D at home |
| Nivolumab | IV, once every 2 or 4 weeks until it no longer works | Q7D in clinic when given as co-therapy or QD, Q2D, Q3D, Q6D or Q7D at home |

TABLE 7

Exemplary Therapeutic Regimens for Combination Therapy: Melanoma

| Primary Therapy | Typical Regimen | Resolvin regimen in combination therapy |
|---|---|---|
| Pembrolizumab | IV, once every 3 or 6 weeks, no limit on duration of therapy | Q7D in clinic when given as co-therapy or QD, Q2D, Q3D, Q6D or Q7D at home |
| Nivolumab | IV, once every 2 or 4 weeks until it no longer works | Q7D in clinic when given as co-therapy or QD, Q2D, Q3D, Q6D or Q7D at home |
| Nivolumab + ipilimumab | IV, once every 3, up to 4 cycles; thereafter, nivolumab alone every 2 or 4 weeks until it no longer works | Q7D in clinic when given as co-therapy or QD, Q2D, Q3D, Q6D or Q7D at home |
| Binimetinib + Encorafenib | PO, Binimetinib (BID), Encorafenib (QD), no limit on duration of therapy | QD, Q2D, Q3D, Q6D or Q7D at home or in clinic |
| Vemurafenib + Cobimetinib | PO, Vemurafenib (BID), Cobimetinib (QD), no limit on duration of therapy | QD, Q2D, Q3D, Q6D or Q7D at home or in clinic |
| Dabrafenib + Trametinib | PO, Dabrafenib (BID), Trametinib (QD), no limit on duration of therapy | QD, Q2D, Q3D, Q6D or Q7D at home or in clinic |

TABLE 8

Exemplary Therapeutic Regimens for Combination Therapy: Brain Cancer

| Primary Therapy | Typical Regimen | Resolvin regimen in combination therapy |
|---|---|---|
| Bevacizumab + temozolomide | Bevacizumab (IV): Q3W, 21-day cycle Temozolomide (PO): QD, 21 day cycle No cycle limit | QD, Q2D, Q3D, Q6D or Q7D at home or in clinic |
| Temozolomide (PO) + radiation | QD with radiation for 6 weeks Days 1-5 in 28 day cycles after radiation No cycle limit | QD, Q2D, Q3D, Q6D or Q7D at home or in clinic |

TABLE 9

Exemplary Therapeutic Regimens for Combination Therapy: Breast Cancer

| Primary Therapy | Typical Regimen | Resolvin regimen in combination therapy |
|---|---|---|
| Neoadjuvant phase 1: Carboplatin (IV) + Paclitaxel (IV) + Pembrolizumab (IV), Neoadjuvant phase 2; Cyclophosphamide (IV) + Doxorubicin (IV) + Pembrolizumab (IV) Adjuvant phase: Pembrolizumab (IV) | Neoadjuvant phase 1, Q3W up to 4 cycles; Neoadjuvant phase 2, Q3W up to 4 cycles; Adjuvant phase: Q3W up to 9 cycles | Q7D in clinic when given as co-therapy or QD, Q2D, Q3D, Q6D or Q7D at home |
| Doxorubicin (IV) + Cyclophosphamide (IV) | Q2W up to four cycles. | Q7D in clinic when given as co-therapy or QD, Q2D, Q3D, Q6D or Q7D at home |
| Docetaxel (IV) + Cyclophosphamide (IV) | Q3W up to four cycles | Q7D in clinic when given as co-therapy or QD, Q2D, Q3D, Q6D or Q7D at home |
| Capecitabine (PO) | QD; until it no longer works | QD, Q2D, Q3D, Q6D or Q7D at home or in clinic |
| Gemcitabine (IV) | Days 1, 8, 15 every 28-days, 6 cycles, up to 24 weeks | Q7D in clinic when given as co-therapy or QD, Q2D, Q3D, Q6D or Q7D at home |
| Paclitaxel (IV) | Q2W or Q3W up to 4 cycles (dose dense) or Q7D for 12 weeks | Q7D in clinic when given as co-therapy or QD, Q2D, Q3D, Q6D or Q7D at home |

As used herein, "combination therapy" or "co-therapy" includes the administration of a therapeutically effective amount of one or more of the compounds or compositions described here as part of a specific treatment regimen intended to provide a beneficial effect from the co-action of the compounds described here and one or more additional active agents (i.e., additional API) or therapies. The beneficial effect of the combination in the context of the present methods may include, for example, pharmacokinetic or pharmacodynamic co-action resulting from the combination. The beneficial effect of the combination may also relate to the mitigation of a toxicity, side effect, or adverse event associated with another agent in the combination. "Combination therapy" is not intended to encompass the administration of two or more compounds as part of separate monotherapy regimens that incidentally and arbitrarily result in a beneficial effect that was not intended or predicted. In some embodiments, the compounds and compositions described here are useful as adjunctive therapy to a primary therapy.

The one or more additional APIs can be formulated for co-administration with a resolvin or its salt form as described herein, either in a single dosage form, or in separate dosage forms. When the additional API is administered separately from the resolvin, or its salt, it can be administered by the same or a different route of administration from the resolvin. Accordingly, the methods described here encompass administering the resolvin, or its salt, together with the at least one additional API, or separately from the additional API. Where delivery is together, the resolvin, or its salt, may be delivered in as a single dosage form that includes the additional API, or in a separate dosage form.

In some aspects, the administration of a composition comprising an resolvin or its salt in combination with one or more additional therapeutic agents as described herein provides a synergistic response in the subject being treated. In this context, the term "synergistic" refers to the efficacy of the combination being more effective than the additive effects of either single therapy alone or less variable than either single therapy alone. The synergistic effect of a combination therapy according to the disclosure can permit the use of lower dosages and/or less frequent administration of at least one agent in the combination compared to its dose and/or frequency outside of the combination. Additional beneficial effects of the combination can be manifested in the longer therapeutic use of at least one agent in the combination compared to its duration of use without the combination or avoidance or reduction of adverse or unwanted side effects associated with the use of either therapy in the combination alone (also referred to as monotherapy).

Salt Compounds

In certain embodiments, the compounds for use in the compositions and methods described here are salts of resolvins in which at least one or two resolvin molecules are ionically bound to at least one basic function that is provided by a scaffold as described in Formulas I-IV below. In general, the carboxylic acid moiety of the resolvin molecule or molecules forming the SPM component of the compounds described here is deprotonated to form an ionic bond with a basic function (or functions) of the scaffold portion of the compound.

The compounds described herein can exist in unsolvated forms as well as solvated forms, including hydrated forms. In general, the solvated forms are equivalent to unsolvated forms and are intended to be encompassed within the scope of the present invention. In general, all physical forms are equivalent for the uses contemplated by the present invention and are intended to be within the scope of the present invention.

The abbreviations used herein have their conventional meaning within the chemical and biological arts. The chemical structures and formulae set forth herein are constructed according to the standard rules of chemical valency known in the chemical arts. For example, in instances where a substituents such as —$NH_3$ are shown without a charge, it is understood to possess a formal charge, i.e. $NH_3^+$.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals, having the number of carbon atoms designated (i.e., $C_1$-$C_{10}$ means one to ten carbons).

The term "basic function" refers to a positively charged or protonated primary amine, a positively charged secondary amine, a positively charged tertiary amine, or a positively charged guanidine. In embodiments, basic function refers to —$NH_3^+$, —$NHC(NH_2^+)NH_2$, —$NHR^6R^7$, —$NR^6R^7R^8$, wherein $R^6$, $R^7$, and $R^8$ are each independently hydrogen, —CN, —COOH, —$CONH_2$, unsubstituted alkyl, unsubstituted heteroalkyl, unsubstituted cycloalkyl, unsubstituted heterocycloalkyl, unsubstituted aryl, or unsubstituted heteroaryl; $R^6$ and $R^7$ substituents bonded to the same nitrogen atom may optionally be joined to form a unsubstituted heterocycloalkyl or unsubstituted heteroaryl. In embodiments, the basic function is a hydrogen bond acceptor. In embodiments, the basic function is a positively charged amine.

It is understood that due to resonance a charge may be distributed across the molecule. The chemical structures and formulae set forth herein are constructed according to the standard rules of chemical valency known in the chemical arts, and as such one of skill in the art would recognize the equivalency of the moieties possessing resonance structures.

In embodiments, the "side chain of an amino acid" or "side chain" or "side-chain" as used herein is used in accordance with its ordinary meaning and refers to the functional substituent contained on naturally occurring amino acids. Naturally occurring amino acids are those encoded by the genetic code (e.g. alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine), as well as those amino acids that are later modified, e.g., hydroxyproline, γ-carboxyglutamate, and O-phosphoserine. In embodiments, the side chain of an amino acid is ionized (e.g., it has a formal charge).

In embodiments, the side chain is selected from the group consisting of H,

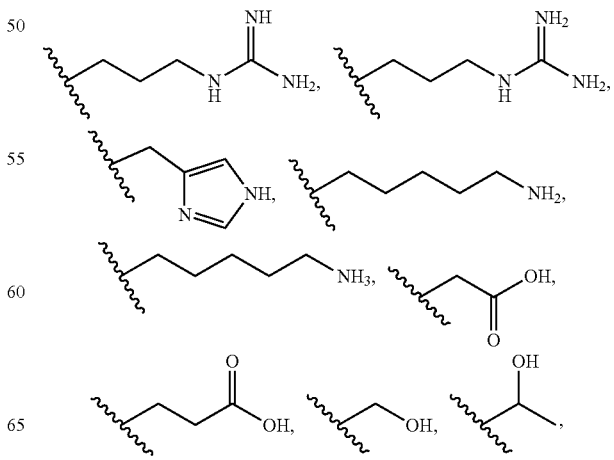

-continued

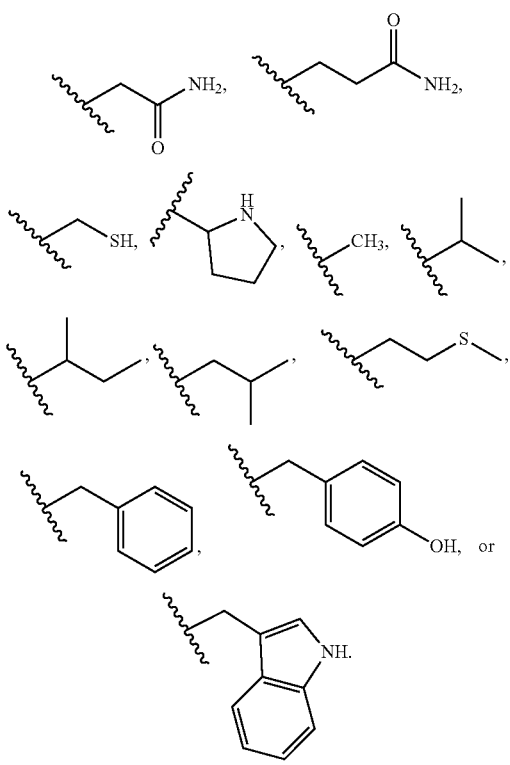

In embodiments, the side chain is H. In embodiments, the side chain is

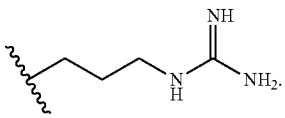 [SMILES: *CCCNC(=N)N]

In embodiments, the side chain is

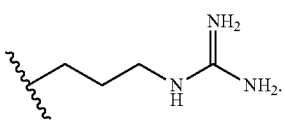 [SMILES: *CCCNC(=N)N]

In embodiments, the side chain is

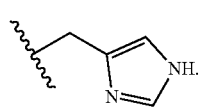

In embodiments, the side chain is

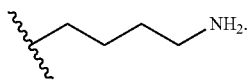 [SMILES: *CCCCN]

In embodiments, the side chain is

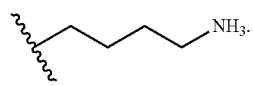

In embodiments, the side chain is

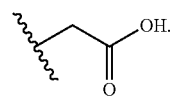

In embodiments, the side chain is

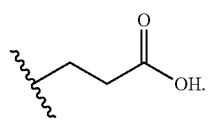 [SMILES: *CCC(=O)O]

In embodiments, the side chain is

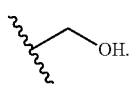 [SMILES: *CO]

In embodiments, the side chain is

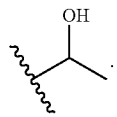

In embodiments, the side chain is

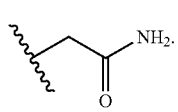

In embodiments, the side chain is

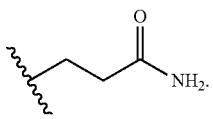

In embodiments, the side chain is

In embodiments, the side chain is

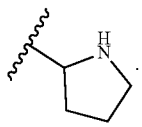

In embodiments, the side chain may optionally be joined to an adjacent nitrogen to form a unsubstituted heterocycloalkyl (e.g., pyyrolidinyl).

In embodiments, the side chain is

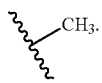

In embodiments, the side chain is

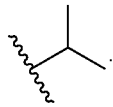 [SMILES: *C(C)C]

In embodiments, the side chain is

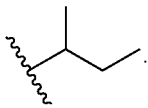

In embodiments, the side chain is

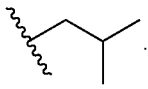 [SMILES: *CC(C)C]

In embodiments, the side chain is

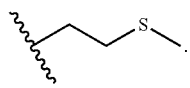 [SMILES: *CCSC]

In embodiments, the side chain is

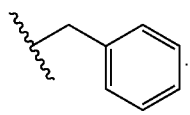

In embodiments, the side chain is

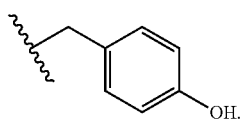 [SMILES: *Cc1ccc(O)cc1]

In embodiments, the side chain is

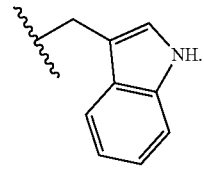 [SMILES: *Cc1c[nH]c2ccccc12]

The side chain of glycine is H. The side chain of arginine is

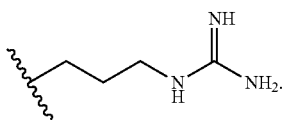 [SMILES: *CCCNC(=N)N]

The side chain of histidine is

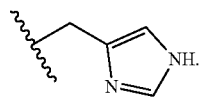 [SMILES: *Cc1c[nH]cn1]

The side chain of lysine is

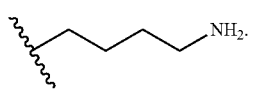 [SMILES: *CCCCN]

The side chain of aspartic acid is

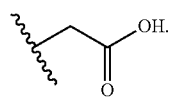 [SMILES: *CC(=O)O]

The side chain of glutamic acid is

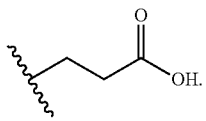 [SMILES: *CCC(=O)O]

The side chain of serine is

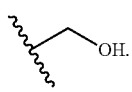 [SMILES: *CO]

The side chain of threonine is

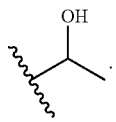 [SMILES: *C(C)O]

The side chain of asparagine is

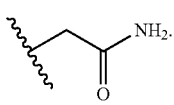

The side chain of glutamine is

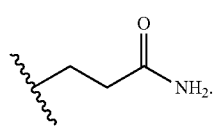 [SMILES: *CCC(N)=O]

The side chain of cysteine is

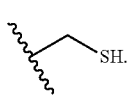

The side chain of proline is

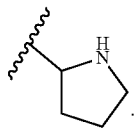 [SMILES: *C1CCCN1]

The side chain of alanine is

The side chain of valine is

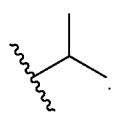

The side chain of isoleucine is

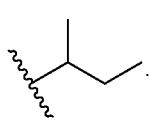 [SMILES: *C(C)CC]

The side chain of leucine is

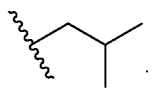 [SMILES: *CC(C)C]

The side chain of methionine is

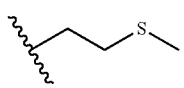

The side chain of phenylalanine is

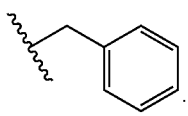 [SMILES: *Cc1ccccc1]

The side chain of tyrosine is

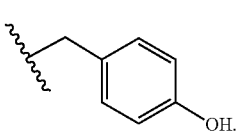 [SMILES: *Cc1ccc(O)cc1]

The side chain of tryptophan is

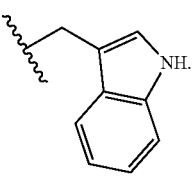 [SMILES: *Cc1c[nH]c2ccccc12]

The term "non-natural amino acid side-chain" refers to the functional substituent of compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium, allylalanine, 2-aminoisobutryric acid. Non-natural amino acids are non-proteinogenic amino acids that either occur naturally or are chemically synthesized. Such analogs have modified R groups (e.g., norleucine) or modified peptide backbones, but retain the same basic chemical structure as a naturally occurring amino acid. Non-limiting examples include exo-cis-3-Aminobicyclo[2.2.1]hept-5-ene-2-carboxylic acid hydrochloride, cis-2-Aminocycloheptanecarboxylic acid hydrochloride, cis-6-Amino-3-cyclohexene-1-carboxylic acid hydrochloride, cis-2-Amino-2-methylcyclohexanecarboxylic acid hydrochloride, cis-2-Amino-2-methylcyclopentanecarboxylic acid hydrochloride, 2-(Boc-aminomethyl)benzoic acid, 2-(Boc-amino)octanedioic acid, Boc-4,5-dehydro-Leu-OH (dicyclohexylammonium), Boc-4-(Fmoc-amino)-L-phenylalanine, Boc-β-Homopyr-OH, Boc-(2-indanyl)-Gly-OH, 4-Boc-3-morpholineacetic acid, 4-Boc-3-morpholineacetic acid, Boc-pentafluoro-D-phenylalanine, Boc-pentafluoro-L- phenylalanine, Boc-Phe(2-Br)—OH, Boc-Phe(4-Br)—OH, Boc-D-Phe(4-Br)—OH, Boc-D-Phe(3-Cl)—OH, Boc-Phe (4-NH2)-OH, Boc-Phe(3-NO2)-OH, Boc-Phe(3,5-F2)-OH, 2-(4-Boc-piperazino)-2-(3,4-dimethoxyphenyl)acetic acid purum, 2-(4-Boc-piperazino)-2-(2-fluorophenyl)acetic acid purum, 2-(4-Boc-piperazino)-2-(3-fluorophenyl)acetic acid purum, 2-(4-Boc-piperazino)-2-(4-fluorophenyl)acetic acid purum, 2-(4-Boc-piperazino)-2-(4-methoxyphenyl)acetic acid purum, 2-(4-Boc-piperazino)-2-phenylacetic acid purum, 2-(4-Boc-piperazino)-2-(3-pyridyl)acetic acid purum, 2-(4-Boc-piperazino)-2-[4-(trifluoromethyl)phenyl] acetic acid purum, Boc-β-(2-quinolyl)-Ala-OH, N-Boc-1,2, 3,6-tetrahydro-2-pyridinecarboxylic acid, Boc-β-(4-thiazolyl)-Ala-OH, Boc-β-(2-thienyl)-D-Ala-OH, Fmoc-N-(4-Boc-aminobutyl)-Gly-OH, Fmoc-N-(2-Boc-aminoethyl)-Gly-OH, Fmoc-N-(2,4-dimethoxybenzyl)-Gly-OH, Fmoc-(2-indanyl)-Gly-OH, Fmoc-pentafluoro-L-phenylalanine, Fmoc-Pen(Trt)-OH, Fmoc-Phe(2-Br)—OH, Fmoc-Phe(4-Br)—OH, Fmoc-Phe(3,5-F2)-OH, Fmoc-β-(4-thiazolyl)-Ala-OH, Fmoc-β-(2-thienyl)-Ala-OH, 4-(Hydroxymethyl)-D-phenylalanine.

Formula I Compounds

In embodiments, the disclosure provides compounds of Formula I, including enantiomers, polymorphs, solvates, and hydrates thereof:

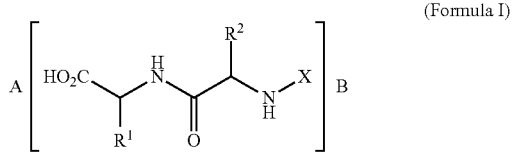

(Formula I)

wherein
A and B are each independently resolvin anion;
A and B may be the same or different;
either A or B, but not both, may be absent,
$R^1$ and $R^2$ are each independently a $C_1$-$C_{10}$ alkyl comprising at least one basic function and is optionally branched;
X is H or CO—Z and Z is a single amino acid residue or a peptide comprising 2 to 18 amino acid residues;
when either A or B is absent:
one of $R^1$, $R^2$ and CO—Z is protonated; or
H is positively charged; and
the one of $R^1$, $R^2$ and the CO—Z that is protonated or the positively charged H forms an ionic bond with either A or B; and
when A and B are both present:
two of $R^1$, $R^2$ and CO—Z are protonated; or
one of $R^1$, $R^2$ and CO—Z is protonated, and H is positively charged; and
the two of $R^1$, $R^2$ and the CO—Z that are protonated or the one of $R^1$, $R^2$ and the CO—Z that is protonated and the positively charged H each respectively form an ionic bond with A and B.

Compounds of Formula I comprise a peptide component consisting of at least 2 amino acid moieties and one or two resolvin molecules (A, B) as the SPM component. The SPM component is described in more detail below. In embodiments, the SPM component comprises or consists of an SPM selected from an E or D series resolvin. In embodiments, the SPM component comprises or consists of an aspirin-triggered (AT) resolvin. In embodiments, the AT resolvin is selected from the group consisting of AT-RvE1, AT-RvE2, and AT-RvE3. In embodiments, the AT resolvin is selected from the group consisting of AT-RvE1, AT-RvD1, and AT-RvD2. In embodiments, the SPM component consists of an E series resolvin; in embodiments, the E series resolvin is selected from RvE1, RvE2, RvE3, RvE4, AT-RvE1, AT-RvE2, and AT-RvE3.

The peptide component may be from 2 to 10 or 2 to 20 amino acids in length, preferably 2, 3, 4, or 5 amino acids in length. The peptide component consists of 2 amino acid residues when X is H, or is a peptide of from 3 to 5, 3 to 10, or 3 to 20 amino acid residues where X is CO—Z.

Each amino acid moiety of the peptide component may, independently, comprise or consist of a single natural or non-naturally occurring amino acid residue. In embodiments, the amino acid residues are independently selected from a residue of glycine, alanine, valine, leucine, isoleucine, serine, cysteine, threonine, methionine, proline, phenylalanine, tyrosine, tryptophan, histidine, lysine, arginine, aspartic acid, glutamic acid, asparagine, and glutamine.

$R^1$ and $R^2$ are each independently unsubstituted $C_1$-$C_{10}$ alkyl including at least one basic function. In embodiments, the basic function is the side chain of an amino acid moiety. In embodiments, the amino acid moiety is selected from lysine, arginine, and glutamine. In embodiments, the basic function is selected from the group consisting of a positively charged primary amine, a positively charged secondary amine, a positively charged tertiary amine, and a positively charged guanidine.

In embodiments, basic function refers to —$NH_3$, —$NHC(NH_2^+)NH_2$, —$NHR^6R^7$, or —$NR^6R^7R^8$, wherein $R^6$, $R^7$, $R^8$ are each independently hydrogen, —CN, —COOH, —$CONH_2$, unsubstituted alkyl, unsubstituted heteroalkyl, unsubstituted cycloalkyl, unsubstituted heterocycloalkyl, unsubstituted aryl, or unsubstituted heteroaryl; $R^6$ and $R^7$ substituents bonded to the same nitrogen atom may optionally be joined to form a unsubstituted heterocycloalkyl or unsubstituted heteroaryl. In embodiments, the basic function is a positively charged amine. In embodiments, the basic function is a primary amine. In embodiments, the basic function is —$NH_3^+$.

In embodiments, X is H and the peptide component consists of a dipeptide of amino acids independently selected from lysine, arginine, and glutamine, or a derivative of one or more of the foregoing. In embodiments, X is H and the peptide component consists of a dipeptide of lysine. In embodiments, X is H and $R^1$ and $R^2$ are each independently selected from —$(CH_2)_3$—$NHC(NH_2^+)$—$NH_2$, —$(CH_2)_4$—$NH_3^+$, and —$(CH_2)_2$—$C(O)NH_3^+$. In embodiments, $R^1$ and $R^2$ are the same. In embodiments, $R^1$ and $R^2$ are different.

In embodiments, X is CO—Z, and Z is either a single amino acid residue or a peptide of from 2 to 10 or 2 to 5 amino acid residues, and the peptide component comprises at least one or two amino acids independently selected from lysine, arginine, and glutamine.

In embodiments, X is H and $R^1$ and $R^2$ are each independently selected from —$(CH_2)_3$—$NHC(NH_2^+)NH_2$, —$(CH_2)_4$—$NH_3^+$, and —$(CH_2)_2$—$C(O)NH_3^+$. In embodiments, $R^1$ and $R^2$ are the same. In embodiments, $R^1$ and $R^2$ are different.

In embodiments, X is CO—Z, and Z is either a single amino acid residue or a peptide of from 2 to 10 or 2 to 5 amino acid residues, and $R^1$ and $R^2$ are each independently selected from —$(CH_2)_3$—$NHC(NH_2^+)NH_2$, —$(CH_2)_4$—$NH_3^+$, and —$(CH_2)_2$—$C(O)NH_3^+$. In embodiments, $R^1$ and $R^2$ are the same. In embodiments, $R^1$ and $R^2$ are different.

In embodiments, —NHC(NH$_2^+$)NH$_2$ is

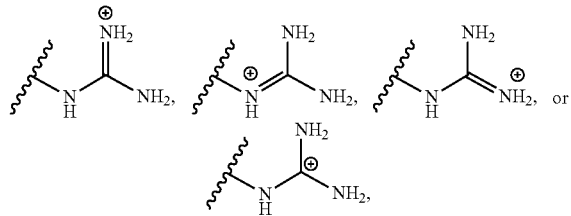

In embodiments, either A or B is absent. Where either A or B is absent, the compound may be referred to as "mono" salt. In embodiments, A and B are both present. Where A and B are both present, the compound may be referred to as a "bis" salt. In one embodiment, A and B are each an SPM, and A and B are the same or different.

In embodiments, A and B are the same or different and each is independently selected from an E series resolvin. In embodiments, the E series resolvin is selected from RvE1, RvE2, RvE3, RvE4, AT-RvE1, AT-RvE2, and AT-RvE3. In embodiments, A and B are the same and selected from the group consisting of resolvin E1, resolvin D2, and aspirin triggered resolvin D1.

In embodiments, A and B are the same and selected from the group consisting of RvE1, RvE2, RvE3, RvE4, AT-RvE1, AT-RvE2, and AT-RvE3; $R^1$ and $R^2$ are both —(CH$_2$)$_4$—Y$^2$, Y$^2$ is NH$_3^+$, and X is H. This selection of $R^1$, $R^2$, and $Y^2$ may be referred to herein as a "lysyl lysine" (which may be abbreviated herein as "lys-lys") dipeptide. In this embodiment, the peptide component is a lysine dipeptide.

In embodiments, A and B are the same and selected from an E or D series resolvin; $R^1$ and $R^2$ are both —(CH$_2$)$_4$—Y$^2$, Y$^2$ is NH$_3^+$, and X is H. As noted above, this selection of $R^1$, $R^2$, and $Y^2$ may be referred to herein as a "lysyl lysine" dipeptide or a "lys-lys" dipeptide. In this embodiment, the peptide component is a lysine dipeptide.

In embodiments, the compound of Formula I is a mono or bis SPM lysyl-lysine (lys-lys) compound selected from the group consisting of RvE1 lys-lys, RvE2 lys-lys, RvE3 lys-lys, RvE4 lys-lys, AT-RvE1 lys-lys, AT-RvE2 lys-lys, and AT-RvE3 lys-lys. In embodiments, the compound of Formula I is a mono or bis SPM lysyl-lysine (lys-lys) compound selected from the group consisting of RvD1 lys-lys, RvD2 lys-lys, RvD3 lys-lys, RvD4 lys-lys, RvD5 lys-lys, RvD6 lys-lys, and the aspirin-triggered counterparts of the foregoing.

Exemplary compounds of the lysyl-lysine embodiment of Formula I are provided in Table 5. In embodiments, the compound of Formula I is selected from the group consisting of Compounds 4, 9, 44, 49, 54, and 59 (E series) of Table 5. In embodiments, a compound of Formula I is selected from the group consisting of Compounds 4, 9, 14, 19, 24, 29, 34, and 39 of Table 5. In embodiments, a compound of Formula I is selected from the group consisting of Compounds 4, 9, 24, 29, 34, and 39 of Table 5. In embodiments, a compound of Formula I is selected from the group consisting of Compounds 4 and 9 (RvE1 and AT-RvE1 embodiments).

Formula II Compounds

In embodiments, the disclosure provides compounds of Formula II or an enantiomer, polymorph, solvate, or hydrate thereof:

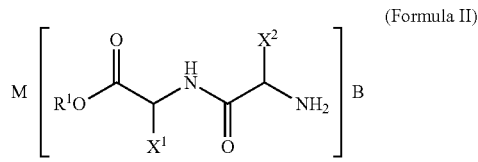

wherein $R^1$ is H, or absent, $X^1$ and $X^2$ are each independently the side chain of an amino acid residue, M is a positively charged optional molecule, and B is a resolvin anion.

In embodiments, $R^1$ is H and $X^1$ and $X^2$ are the side chain of glycine.

In embodiments, $R^1$ is H and $X^1$ is the side chain of lysine, and $X^2$ is selected from the side chain of valine, the side chain of serine, the side chain of leucine, the side chain of histidine A compound of Formula II consists of at least (i) a dipeptide component and (ii) an SPM component (B), with a positively charged optional molecule (M). The dipeptide component contains $X^1$ and $X^2$ which may be the same or different, and are each the side chain of an amino acid residue. In embodiments, at least one of $X^1$ and $X^2$ is the side chain of an amino acid residue selected from serine, threonine, glycine, alanine, valine, leucine, isoleucine, methionine, and phenylalanine. In embodiments, where one of $X^1$ and $X^2$ is the side chain of an amino acid residue selected from serine, threonine, glycine, alanine, valine, leucine, isoleucine, methionine, and phenylalanine, the remainder of $X^1$ or $X^2$ is the side chain of an amino acid independently selected from lysine, arginine, histidine, aspartate, glutamate, serine, threonine, asparagine, glutamine, cysteine, glycine, proline, alanine, valine, isoleucine, leucine, methionine, phenylalanine, tyrosine, and tryptophan. In embodiments, the remainder is the side chain of lysine. In embodiments, at least one of $X^1$ and $X^2$ is the side chain of glycine, valine, serine, leucine, or histidine, and the remainder is the side chain of lysine.

In embodiments, the SPM component (B) comprises or consists of an E or D series resolvin. In embodiments of the compound of Formula II, B is selected from the group consisting of RvE1, RvE2, RvE3, RvE4, AT-RvE1, AT-RvE2, and AT-RvE3. In embodiments, the SPM component (B) comprises or consists of a D series resolvin selected from the group consisting of RvD1, RvD2, RvD3, RvD4, RvD5, RvD6, and their aspirin-triggered counterparts. In embodiments, the SPM component comprises or consists of an aspirin-triggered (AT) resolvin.

In embodiments, the compound of Formula II is a glycine dipeptide where $R^1$ is H, $X^1$ and $X^2$ are each H, M is absent and B is selected from the group consisting of RvE1, RvE2, RvE3, RvE4, AT-RvE1, AT-RvE2, and AT-RvE3.

In embodiments, the compound of Formula II is a glycine dipeptide where $R^1$ is H, $X^1$ and $X^2$ are each H, M is absent and B is selected from the group consisting of RvD1, RvD2, RvD3, RvD4, RvD5, RvD6, and their aspirin-triggered counterparts.

The positively charged optional molecule (M) has at least one basic function which forms an ionic bond with the terminal carboxyl of the amino acid component. In embodiments, M is a monovalent metal cation, e.g., Na$^+$, K$^+$, or a molecule having at least one basic function, such as a monovalent amine-based cation, e.g., tri-ethanolamine, or tri-ethylamine, or a basic pharmaceutical compound such as metformin or gabapentin.

Compounds of Formula II encompass simple salts of dipeptides and an SPM component (Formula IIa), simple metal salts of the dipeptides and an SPM component with a monovalent metal (Formula IIb), and simple non-metal salts of the dipeptides and an SPM component with a non-metal molecule having at least one basic function (Formula IIc).

Formula III Compounds

In embodiments, the disclosure provides compounds of Formula III or an enantiomer, polymorph, solvate, or hydrate thereof:

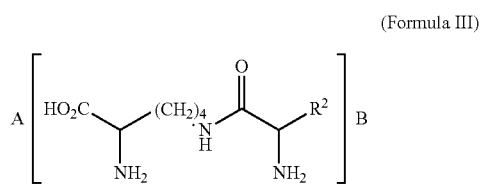

(Formula III)

wherein
$R^2$ is a $C_1$-$C_{10}$ alkyl comprising at least one basic function;
A and B are each independently a resolvin anion;
A and B may be the same or different; and
either A or B, but not both, may be absent.

In embodiments, $R^2$ is the side chain of an amino acid residue selected from lysine, arginine, and glutamine. In embodiments, $R^2$ is the side chain of lysine. In embodiments, $R^2$ is selected from the group consisting of —(CH$_2$)$_3$—NHC(NH$_2^+$)NH$_2$, —(CH$_2$)$_4$—NH$_3^+$, and —(CH$_2$)$_2$—C(O)NH$_3^+$. In embodiments, $R^2$ is —(CH$_2$)$_4$—NH$_3^+$.

In embodiments, the basic function of $R^2$ is selected from the group consisting of a positively charged primary amine, a positively charged secondary amine, a positively charged tertiary amine, and a positively charged guanidine.

In embodiments, the basic function of $R^2$ refers to —NH$_3$, —NHC(NH$_2^+$)NH$_2$, —NHR$^6$R$^7$, or —NR$^6$R$^7$R$^8$, wherein $R^6$, $R^7$, $R^8$ are each independently hydrogen, —CN, —COOH, —CONH$_2$, unsubstituted alkyl, unsubstituted heteroalkyl, unsubstituted cycloalkyl, unsubstituted heterocycloalkyl, unsubstituted aryl, or unsubstituted heteroaryl; $R^6$ and $R^7$ substituents bonded to the same nitrogen atom may optionally be joined to form a unsubstituted heterocycloalkyl or unsubstituted heteroaryl. In embodiments, the basic function is a positively charged amine. In embodiments, the basic function is a primary amine. In embodiments, the basic function is —NH$_3^+$.

In embodiments, $R^2$ is the side chain of lysine, A and B are the same molecule and are selected from an E series resolvin; in embodiments, the E series resolvin is selected from the group consisting of RvE1, RvE2, RvE3, RvE4, AT-RvE1, AT-RvE2, and AT-RvE3. In embodiments, $R^2$ is the side chain of lysine, A and B are the same molecule and are selected from the group consisting of RvD1, RvD2, RvD3, RvD4, RvD5, RvD6, and their aspirin-triggered counterparts.

In embodiments, the SPM component (A, B) comprises or consists of an E series resolvin; in embodiments, the E series resolvin is selected from the group consisting of RvE1, RvE2, RvE3, RvE4, AT-RvE1, AT-RvE2, and AT-RvE3. In embodiments, the SPM component (A, B) comprises or consists of a D series resolvin selected from RvD1, RvD2, RvD3, RvD4, RvD5, RvD6, and their aspirin-triggered counterparts.

In an embodiment of the compound of Formula III, A and B are the same or different and each is independently selected from an E series resolvin and $R^2$ is —(CH$_2$)$_4$—NH$_3^+$. In embodiments, the E series resolvin is selected from RvE1, RvE2, RvE3, RvE4, AT-RvE1, AT-RvE2, and AT-RvE3. This selection of $R^2$ may be referred to herein as a "linear lysyl lysine" (linear lys-lys) dipeptide. In this embodiment, the peptide component is a lysine dipeptide. In embodiments, A and B are the same.

In an embodiment of the compound of Formula III, A and B are the same and selected from a D series resolvin selected from RvD1, RvD2, RvD3, RvD4, RvD5, RvD6, and their aspirin-triggered counterparts, and $R^2$ is —(CH$_2$)$_4$—NH$_3^+$. This selection of $R^2$ may be referred to herein as a "linear lysyl lysine" (linear "lys-lys") dipeptide. In this embodiment, the peptide component is a lysine dipeptide.

Exemplary compounds of Formula III are provided in Table 5. In embodiments, the compound of Formula III is selected from the group consisting of Compounds 5, 10, 45, 50, 55, and 60 (E series) of Table 5. In embodiments, a compound of Formula III is selected from the group consisting of Compounds 5, 10, 15, 20, 25, 30, 35, and 40 of Table 5. In embodiments, a compound of Formula III is selected from the group consisting of Compounds 5 and 10 (RvE1 and AT-RvE1 embodiments) of Table 5.

Formula IV Compounds

In embodiments, the disclosure provides compounds of Formula IV or an enantiomer, polymorph, solvate, or hydrate thereof:

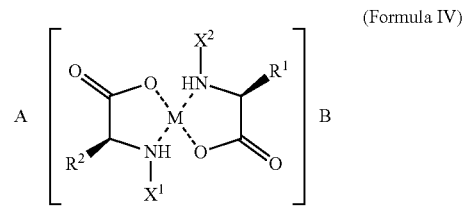

(Formula IV)

wherein
M is a divalent metal;
A and B are each independently a resolvin anion;
A and B may be the same or different;
either A or B, but not both, may be absent;
$R^1$ and $R^2$ are each independently a $C_1$-$C_{10}$ alkyl comprising at least one basic function;
$X^1$ and $X^2$ are each independently H or CO—Z and Z is a peptide comprising 1 to 5 amino acids or a pharmaceutically acceptable salt thereof;
when either A or B is absent:
one of $R^1$, $R^2$ and the two CO—Z's is protonated; or
one of the two H's is positively charged; and
the one of $R^1$, $R^2$ and the two CO—Z's that is protonated or the one of the positively charged H's forms an ionic bond with either A or B; and
when A and B are both present:
two of $R^1$, $R^2$ and the two CO—Z's are protonated; or
one of $R^1$, $R^2$ and the two CO—Z's is protonated, and one of the two H's is positively charged; and
the two of $R^1$, $R^2$ and the two CO—Z's that are protonated or the one of $R^1$, $R^2$ and the two CO—Z's that is protonated and the positively charged H each respectively form an ionic bond with A and B.

Compounds of Formula IV have two amino acid moieties coordinated around a divalent metal cation as the amino acid component and one or two resolvin molecules as the SPM component. In embodiments, the divalent metal cation is $Mg^{2+}$, $Ca^{2+}$, $Mn^{2+}$, $Fe^{2+}$, $Cu^{2+}$, $CO^{2+}$, $Ni^{2+}$, $Mo^{2+}$ or $Zn^{2+}$. In embodiments, the divalent metal cation is $Mg^{2+}$. In embodiments, the divalent metal cation is $Ca^{2+}$. In embodiments, the divalent metal cation is $Zn^{2+}$.

In embodiments, the amino acid component includes or consists of lysine or arginine. In embodiments, the amino acid component includes lysine or arginine. In embodiments, the basic function of $R^1$ and $R^2$ is selected from a primary amine, a secondary amine, a tertiary amine, and a guanidine. In embodiments, basic function refers to $-NH_3$, $-NHC(NH_2^+)NH_2$, $-NHR^6R^7$, or $-NR^6R^7R^8$, wherein $R^6$, $R^7$, $R^8$ are each independently hydrogen, $-CN$, $-COOH$, $-CONH_2$, unsubstituted alkyl, unsubstituted heteroalkyl, unsubstituted cycloalkyl, unsubstituted heterocycloalkyl, unsubstituted aryl, or unsubstituted heteroaryl; $R^6$ and $R^7$ substituents bonded to the same nitrogen atom may optionally be joined to form a unsubstituted heterocycloalkyl or unsubstituted heteroaryl. In embodiments, the basic function is a hydrogen bond acceptor. In embodiments, the basic function is a hydrogen bond donor. In embodiments, the basic function is a positively charged amine.

In embodiments, $R^1$ and $R^2$ are each the side chain of an amino acid residue having a basic function. In embodiments, $R^1$ and $R^2$ are the same and the amino acid residue is lysine or arginine.

In embodiments, $R^1$ and $R^2$ are independently selected from $-(CH_2)_3-Y^1$, and $-(CH_2)_4-Y^2$, where $Y^1$ and $Y^2$ are each a basic function which may be the same or different. In embodiments, $R^1$ is $-CH_2CH_2NH_3$. In embodiments, $R^2$ is $-CH_2CH_2NH_3$. In embodiments, $R^1$ is $-CH_2CH_2CH_2CH_2NH_3$. In embodiments, $R^2$ is $-CH_2CH_2CH_2CH_2NH_3$.

In embodiments, $R^1$ and $R^2$ are both $-(CH_2)_4-Y^2$, and $Y^2$ is $-NH_3^+$.

In embodiments, $R^1$ and $R^2$ are both $-(CH_2)_3-Y^1$, and $Y^1$ is $-NHC(NH_2^+)NH_2$.

In embodiments, $R^1$ is $-(CH_2)_3-Y^1$, $Y^1$ is $-NHC(NH_2^+)NH_2$, $Y^2$ is $-(CH_2)_4-Y^2$, and $Y^2$ is $-NH_3^+$. In embodiments, $R^1$ is $-(CH_2)_4-Y^2$, $Y^2$ is $-NH_3^+$, $R^2$ is $-(CH_2)_3-Y^1$, and $Y^1$ is $NHC(NH_2^+)NH_2$.

In embodiments, $X^1$ and $X^2$ are the same and are hydrogen (H). In embodiments, $X^1$ is hydrogen. In embodiments, $X^2$ is hydrogen.

In an embodiment of the compound of Formula IV, A and B are the same or different and each is independently selected from an E series resolvin. In embodiments, the E series resolvin is selected from RvE1, RvE2, RvE3, RvE4, AT-RvE1, AT-RvE2, and AT-RvE3, M is $Mg^{2+}$, $Ca^{2+}$, or $Zn^{2+}$, $R^1$ and $R^2$ are both $-(CH_2)_4-Y^2$ and $Y^2$ is $NH_3^+$; and $X^1$ and $X^2$ are H. This selection of $R^1$, $R^2$, and $Y^2$ may be referred to herein as the metal "di-lysinate", e.g., "magnesium di-lysinate" or "Mg-di-lysinate". In Table 5, the metal di-lysinate name is abbreviated "SPM-Mlys" where "M" is the metal, e.g., Mg, Ca, or Zn. In this embodiment, the peptide component consists of a lysine dipeptide. In embodiments, A and B are the same.

In an embodiment of the compound of Formula IV, A and B are the same and selected and E or D series resolvin; M is $Mg^{2+}$, $Ca^{2+}$, or $Zn^{2+}$, $R^1$ and $R^2$ are both $-(CH_2)_4-Y^2$ and $Y^2$ is $NH_3^+$; and $X^1$ and $X^2$ are H. This selection of $R^1$, $R^2$, and $Y^2$ may be referred to herein as the metal "di-lysinate", e.g., "magnesium di-lysinate" or "Mg-di-lysinate". In this embodiment, the peptide component consists of a lysine dipeptide.

In embodiments, the SPM component (A,B) comprises or consists of an E series resolvin. In embodiments, the E series resolvin is selected from RvE1, RvE2, RvE3, RvE4, AT-RvE1, AT-RvE2, and AT-RvE3.

In embodiments, the SPM component (A,B) comprises or consists of a D series resolvin. In embodiments, the D series resolvin is selected from RvD1, RvD2, RvD3, RvD4, RvD5, RvD6, and their aspirin-triggered counterparts.

In embodiments, the compound of Formula IV is a mono or bis resolvin magnesium, calcium, or zinc di-lysinate (M-lys-lys, or M-di-lysinate) compound selected from the group consisting of RvE1 M-lys-lys, RvE2 M-lys-lys, RvE3 M-lys-lys, RvE4 M-lys-lys, AT-RvE1 M-lys-lys, AT-RvE2 M-lys-lys, and AT-RvE3 M-lys-lys.

In embodiments, the compound of Formula IV is a mono or bis resolvin magnesium, calcium, or zinc di-lysinate (M-lys-lys, or M-di-lysinate) compound selected from the group consisting of RvD1 M-lys-lys, RvD2 M-lys-lys, RvD3 M-lys-lys, RvD4 M-lys-lys, RvD5 M-lys-lys, RvD6 M-lys-lys, and their aspirin-triggered counterparts.

In embodiments, the compound of Formula IV is a mono or bis resolvin Mg-di-lysinate compound selected from the group consisting of RvE1 Mg-lys-lys, RvE2 Mg-lys-lys, RvE3 Mg-lys-lys, RvE4 Mg-lys-lys, AT-RvE1 Mg-lys-lys, AT-RvE2 Mg-lys-lys, and AT-RvE3 Mg-lys-lys.

In embodiments, the compound of Formula IV is a mono or bis resolvin Ca-di-lysinate compound selected from the group consisting of RvE1 Ca-lys-lys, RvE2 Ca-lys-lys, RvE3 Ca-lys-lys, RvE4 Ca-lys-lys, AT-RvE1 Ca-lys-lys, AT-RvE2 Ca-lys-lys, and AT-RvE3 Ca-lys-lys.

In embodiments, the compound of Formula IV is a mono or bis resolvin Zn-di-lysinate compound selected from the group consisting of RvE1 Zn-lys-lys, RvE2 Zn-lys-lys, RvE3 Zn-lys-lys, RvE4 Zn-lys-lys, AT-RvE1 Zn-lys-lys, AT-RvE2 Zn-lys-lys, and AT-RvE3 Zn-lys-lys.

Exemplary compounds of Formula IV are provided in Table 5.

The SPM Component

The compounds represented by Formulas I-IV each contain at least one or two resolvin molecules, which may be referred to herein as the "SPM component" of the compound, and a scaffold portion to which the SPM component is ionically bound. The terms "mono" and "bis" refer to one (mono) or two (bis) SPM molecules in the salt compound.

In the context of the present disclosure, the term "SPM" refers to resolvins and their aspirin-triggered counterparts (e.g., aspirin-triggered resolvins), as described in more detail infra. Examples of particular SPM molecules that may form the SPM component of the compounds described here, as well as their precursor molecules, are given in Tables 1-4 infra. It is understood that the neutral compounds described in these tables may become charged (i.e., deprotonated) if solvated at the appropriate pH.

In embodiments, the SPM component of a compound described here comprises or consists of one or two SPM molecules selected from mediators derived from eicosapentaenoic acid (EPA) (Table 1); mediators derived from docosahexaenoic acid (DHA) (Table 2); and aspirin-triggered mediators (Table 3). In embodiments, the SPM component of a compound described here comprises or consists of two SPM molecules selected from Tables 1-3. In embodiments, the two SPM molecules are the same or different. In embodiments, the two SPM molecules are the same and are selected from an E series resolvin; in embodiments, the E series resolvin is selected from RvE1, RvE2, RvE3, RvE4, AT-RvE1, AT-RvE2, and AT-RvE3. In embodiments, the two SPM molecules are the same and are selected from the group consisting of RvD1, RvD2, RvE1, AT-RvD1, AT-RvD2, and AT-RvE1. In embodiments, the SPM component of a compound described here consists of one or two SPM molecules selected from an E series resolvin; in embodiments, the E series resolvin is selected from RvE1, RvE2, RvE3, RvE4, AT-RvE1, AT-RvE2, and AT-RvE3. In embodiments, the SPM component of a compound described here consists of one or two SPM molecules selected from the group consisting of RvD1, RvD2, RvE1, AT-RvD1, AT-RvD2, and AT-RvE1. In embodiments, the SPM component is selected from an E series resolvin; in embodiments, the E series resolvin is selected from RvE1, RvE2, RvE3, RvE4, AT-RvE1, AT-RvE2, and AT-RvE3. In embodiments, the SPM component is selected from RvE1, AT-RvE1, and RvD1.

In embodiments, the SPM component of a compound or composition described here is selected from a compound set forth in Table 10, Table 11, or Table 12.

TABLE 10

EPA and Resolvins Derived from EPA

| Name | Abbrev. | Formula | Chemical Name |
|---|---|---|---|
| Eicosapentaenoic acid | EPA | $C_{20}H_{30}O_2$ | 5Z,8Z,11Z,14Z,17Z-eicosapentaenoic acid |
| Resolvin E1 | RvE1 | $C_{20}H_{30}O_5$ | 5S,12R,18R-trihydroxy-6Z,8E,10E,14Z,16E-eicosapentaenoic acid |
| Resolvin E2 | RvE2 | $C_{20}H_{30}O_4$ | 5S,18R-dihydroxy-6E,8Z,11Z,14Z,16E-eicosapentaenoic acid |
| Resolvin E3 | RvE3 | $C_{20}H_{30}O_4$ | 17R,18R-dihydroxy-5Z,8Z,11Z,13E,15E-eicosapentaenoic acid |
| Resolvin E4 | RvE4 | $C_{20}H_{30}O_4$ | 5S,15S-dihydroxy-6E,8Z,11Z,13E,17Z-eicosapentaenoic acid |

TABLE 11

DHA and Resolvins Derived from DHA

| Name | Abbrev. | Formula | Chemical Name |
|---|---|---|---|
| Docosahexaenoic acid | DHA | $C_{22}H_{32}O_2$ | 4Z,7Z,10Z,13Z,16Z,19Z-docosahexaenoic acid |
| Resolvin D1 | RvD1 | $C_{22}H_{32}O_5$ | 7S,8R,17S-trihydroxy-4Z,9E,11E,13Z,15E,19Z-docosahexaenoic acid |
| Resolvin D2 | RvD2 | $C_{22}H_{32}O_5$ | 7S,16R,17S-trihydroxy-4Z,8E,10Z,12E,14E,19Z-docosahexaenoic acid |
| Resolvin D3 | RvD3 | $C_{22}H_{32}O_5$ | 4S,11R,17S-trihydroxy-5Z,7E,9E,13Z,15E,19Z-docosahexaenoic acid |
| Resolvin D4 | RvD4 | $C_{22}H_{32}O_5$ | 4S,5,17S-trihydroxy-6E,8E,10Z,13Z,15E,19Z-docosahexaenoic acid |
| Resolvin D5 | RvD5 | $C_{22}H_{32}O_4$ | 7S,17S-dihydroxy-4Z,8E,10Z,13Z,15E 19Z-docosahexaenoic acid |
| Resolvin D6 | RvD6 | $C_{22}H_{32}O_4$ | 4S,17S-dihydroxy-5E,7Z,10Z,13Z,15E,19Z-docosahexaenoic acid |

TABLE 12

Aspirin-Triggered Resolvins

| Name | Abbrev. | Formula | Chemical Name |
|---|---|---|---|
| Aspirin-triggered Resolvin D1 | AT-RvD1 | $C_{22}H_{32}O_5$ | 7S,8R,17R-trihydroxy-4Z,9E,11E,13Z,15E,19Z-docosahexaenoic acid |
| Aspirin-triggered Resolvin D2 | AT-RvD2 | $C_{22}H_{32}O_5$ | 7S,16R,17R-trihydroxy-4Z,8E,10Z,12E,14E,19Z-docosahexaenoic acid |
| Aspirin-triggered Resolvin D3 | AT-RvD3 | $C_{22}H_{32}O_5$ | 4S,11R,17R-trihydroxy-5Z,7E,9E,13Z,15E,19Z-docosahexaenoic acid |
| Aspirin-triggered Resolvin D4 | AT-RvD4 | $C_{22}H_{32}O_4$ | 4S,5,17R-trihydroxy-6E,8E,10Z,13Z,15E,19Z-docosahexaenoic acid |
| Aspirin-triggered Resolvin D5 | AT-RvD5 | $C_{22}H_{32}O_4$ | 7S,17R-dihydroxy-4Z,8E,10Z,13Z,15E,19Z-docosahexaenoic acid |
| Aspirin-triggered Resolvin D6 | AT-RvD6 | $C_{22}H_{32}O_4$ | 4S,17R-dihydroxy-5E,7Z,10Z,13Z,15E,19Z-docosahexaenoic acid |
| Aspirin-triggered Resolvin E1 | AT-RvE1 | $C_{20}H_{30}O_5$ | 5S,12R,18S-trihydroxy-6Z,8E,10E,14Z,16E-eicosapentaenoic acid |
| Aspirin-triggered Resolvin E2 | AT-RvE2 | $C_{20}H_{30}O_4$ | 5S,18S-dihydroxy-6E,8Z,11Z,14Z,16E-eicosapentaenoic acid |
| Aspirin-triggered Resolvin E3 | AT-RvE3 | $C_{20}H_{30}O_4$ | 17R,18S-dihydroxy-5Z,8Z,11Z,13E,15E-eicosapentaenoic acid |

Pharmaceutical Compositions

The present disclosure provides pharmaceutical compositions comprising a resolvin, or its salt, and a pharmaceutically acceptable carrier. In embodiments, the salt of the resolvin may be a simple salt, such as a sodium, potassium, or magnesium salt, or a compound of Formula I-IV.

In embodiments, the pharmaceutical composition is formulated as a parenteral dosage form such as a sterile aqueous solution or dispersion suitable for parenteral administration. In embodiments, the parenteral dosage form is selected from an intravenous dosage form, an intra-arterial dosage form, or an intramuscular dosage form. In embodiments, the dosage form is suitable for administration by a subcutaneous route.

In embodiments, the pharmaceutical composition is in the form of a sterile aqueous solution or dispersion suitable for administration by either direct injection or by addition to sterile infusion fluids for intravenous infusion, and comprises a solvent or dispersion medium containing, water, ethanol, a polyol (e.g., glycerol, propylene glycol and liquid polyethylene glycol), suitable mixtures thereof.

In accordance with any of these embodiments, the dosage form may be in the form of a clear aqueous solution, which may optionally be frozen, or in the form of a lyophilized solid, preferably a sterile lyophilized solid e.g., contained in container, such as a pre-filled syringe, vial or ampule. In some embodiments, the container contains lyophilized composition and is suitable for reconstitution with a specified amount of sterile water or aqueous buffer for administration by a parenteral route, e.g., intravenous, intra-arterial, or an intramuscular, subcutaneous.

In embodiments, the pharmaceutical composition is formulated as an oral or peroral dosage form. In embodiments, the oral formulation is in the form of e.g., a tablet, capsule, powder, solution, suspension, or emulsion.

In embodiments, the pharmaceutical composition is formulated as a sublingual dosage form. In embodiments, the sublingual formulation is in the form of a tablet, film or spray.

In embodiments, the pharmaceutical composition is formulated for administration via inhalation through the nose or mouth. In embodiments, the inhalable dosage form is a liquid formulation, such as an aqueous solution formulation adapted for pulmonary delivery via a nebulizer, including jet, vibrating mesh, and static mesh or orifice nebulizers. In embodiments, the inhalable dosage form is a dry powder for inhalation (DPI). In embodiments, the inhalable dosage form is a propellant-based aerosol formulation suitable for administration using a metered dose inhaler (MDI).

In embodiments, a pharmaceutical composition comprising a resolvin, or its salt, or a compound of any one of Formulas I-IV is in the form of a unit dose of the resolvin, its salt, or the compound. In embodiments, the unit dosage form is a sterile, freeze-dried composition in a suitable container, such as an ampule or vial. The term "freeze-dried" is synonymous with the term "lyophilized" in this context. In embodiments, the unit dose contains from 1 microgram (ug) to 50 milligrams (mg) of the resolvin free acid or salt. In embodiments, the unit dose contains 1, 5, 10, 25, 50, 100, 250, or 500 micrograms of the resolvin free acid or salt. In embodiments, the unit dose contains 1, 5, 10, or 20 milligrams of the resolvin free acid or salt.

The compositions described here may be formulated using one or more suitable excipients or carriers. A suitable excipient or carrier is one suitable for human or animal use. The term "excipient" refers to an additive that serves some purpose in the composition other than a carrier, for example as a stabilizer, solubilizing agent, or suspending agent. Often, a carrier will serve a dual purpose as a simple carrier or diluent and an excipient. Examples of pharmaceutically acceptable excipients may thus include carriers. Non-limiting examples of excipients for use in the compositions of the invention include sterile liquids, water, buffered saline, ethanol, polyols (for example, glycerol, propylene glycol, liquid polyethylene glycol and the like), oils, detergents, suspending agents, carbohydrates (e.g., glucose, lactose, sucrose or dextran), antioxidants (e.g., ascorbic acid or glutathione), chelating agents, low molecular weight proteins, and suitable mixtures thereof.

A suitable excipient or carrier is typically a pharmaceutically acceptable carrier or excipient for use in animals or humans (or both). The term "pharmaceutically acceptable" indicates approval by a regulatory agency of the Federal or a state government or listed in the U.S. Pharmacopeia or other generally recognized pharmacopeia such as the European Pharmacopeia, for use in animals, and more particularly in humans. In the context of the pharmaceutical compositions of the invention, a "carrier" refers to, for example, a solvent, a diluent, or vehicle with which the ionic salt of the invention is formulated for delivery. Examples of pharmaceutically acceptable carriers for use in the compositions of the invention include, without limitation, sterile aqueous and non-aqueous liquids, water, buffered saline, ethanol, polyols (for example, glycerol, propylene glycol, liquid polyethylene glycol and the like), and oils, for liquid dosage forms; or carbohydrates (e.g., glucose, lactose, sucrose or dextran) for solid dosage forms.

The disclosure also provides packaging and kits comprising pharmaceutical compositions for use in the methods of the present invention. The kit can comprise one or more containers selected from the group consisting of a bottle, a vial, an ampoule, a blister pack, and a syringe. The kit can further include one or more of instructions for use, one or more syringes, one or more applicators, or a sterile solution suitable for reconstituting a pharmaceutical composition of the present invention.

A representative compound of Formula IV, RvE1 magnesium dilysinate, was tested for efficacy in several mouse models of cancer, including the Panc2-H7 model of pancreatic cancer, the Lewis lung carcinoma (LLC) model, the MC38 model of colorectal cancer, and the B16F10 model of melanoma. These models are well established, highly tumorigenic syngeneic models in which murine cancer cell lines are injected subcutaneously (SC) into the dorsum of C57BL/6J mice. If left untreated, these tumors grow rapidly and lead to death or euthanasia, per protocol. As detailed below in Examples 1-9 and the accompanying figures, bis RvE1 Mg-di-lysinate (Compound 1) was unexpectedly effective as an anti-cancer agent in each of these model systems when administered in a less than daily (LTD) dosing regimen. This was unexpected based on the pharmacokinetics of this compound, which indicated that administration of resolvins in a less than daily (LTD) dosing regimen was unlikely to be effective therapeutically, or at least that it is unlikely to be as effective as daily or more frequent dosing or continuous infusion (see Example 10). Without being bound by any theory, the surprising efficacy of LTD dosing of resolvins in the cancer model systems described here may be the result of durable effects on the tumor microenvironment including changes in immune cell phenotype, vascularization, stromal phenotype, and antigen presentation, as well as durable effects on the T-cell compartment such as T-cell priming and increased tumor-infiltrating lymphocytes. In support of this mechanism, RNAseq analysis of pancreatic tumors in mice following treatment with bis RvE1 Mg-di-lysinate shows modulation of T-cells and other immune cells indicative of activation of an adaptive immune response (see Example 11).

Figure 1B:
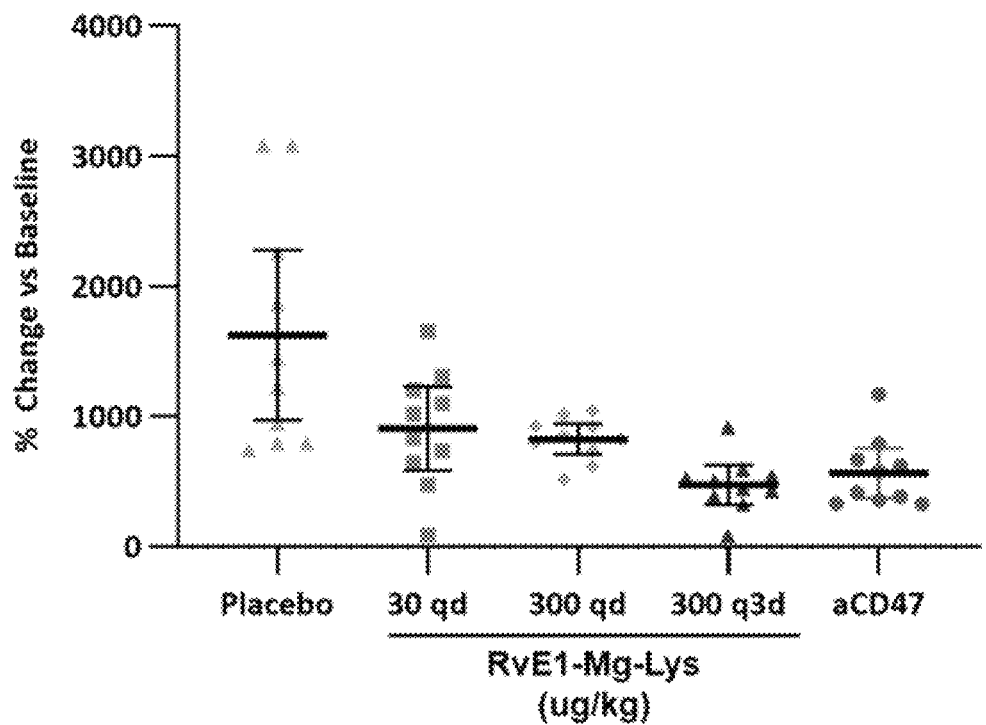
FIG. 1B is a scatter plot showing percent change in tumor volume (Day 15 vs Day 0) for bis RvE1 Mg-di-lysinate in the MC38 model of colorectal cancer.

Example 1—Study of Bis RvE1 Mg-Di-Lysinate Regimen with QD and Q3D Subcutaneous Injection in the MC38 Colorectal Cancer Model The MC38 model of colorectal cancer was used to investigate whether subcutaneous dosing of bis RvE1 Mg-di-lysinate would be useful in treating cancer and to explore the efficacy of less than daily (LTD) dosing compared to daily dosing. Forty (40) C57BL/6J male mice were injected subcutaneously with 1×10e6 living MC-38 cells. Treatment was initiated when tumors were 150-200 mm^3 with bis RvE1 Mg-di-lysinate (30 or 300 ug/g, SC, QD or 300 ug/kg, SC, Q3D), or anti-CD47 (16 mg/kg, IP, Q3D). Mice were sacrificed when the average tumor size of the placebo group reached approximately 2,000 mm^3. As shown in FIG. 1A to FIG. 1B, bis RvE1 Mg-di-lysinate was effective as a single agent with both QD and Q3D dosing at 300 ug/kg dose (* $P<0.05$ vs placebo) with comparable effects to anti-CD47, which independently has been shown to be efficacious in this model and is currently being clinically tested for colorectal cancer. Thus, the study confirmed that subcutaneous dosing with bis RvE1 Mg-di-lysinate is efficacious in an established tumor model on par with a clinical candidate when administered in an LTD dosing regimen. This was unexpected and surprising given the short in vivo half-life of resolvin E1.

Figure 2A:
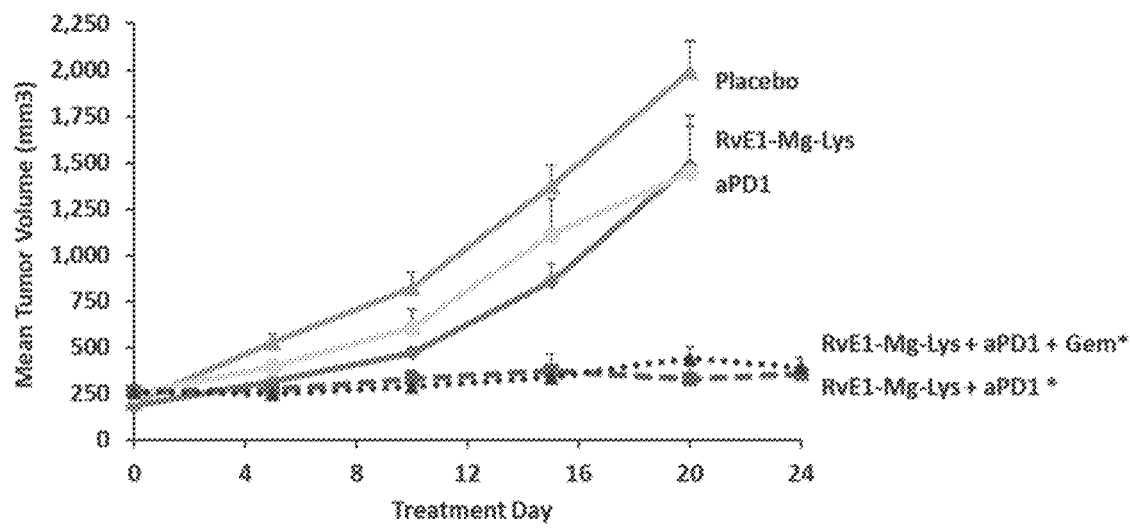
FIG. 2A is a line graph showing tumor volume over time (Day 15 vs Day 0) for bis RvE1 Mg-di-lysinate in the Panc2-H7 model of pancreatic cancer, with and without anti-PD1.
Figure 2B:
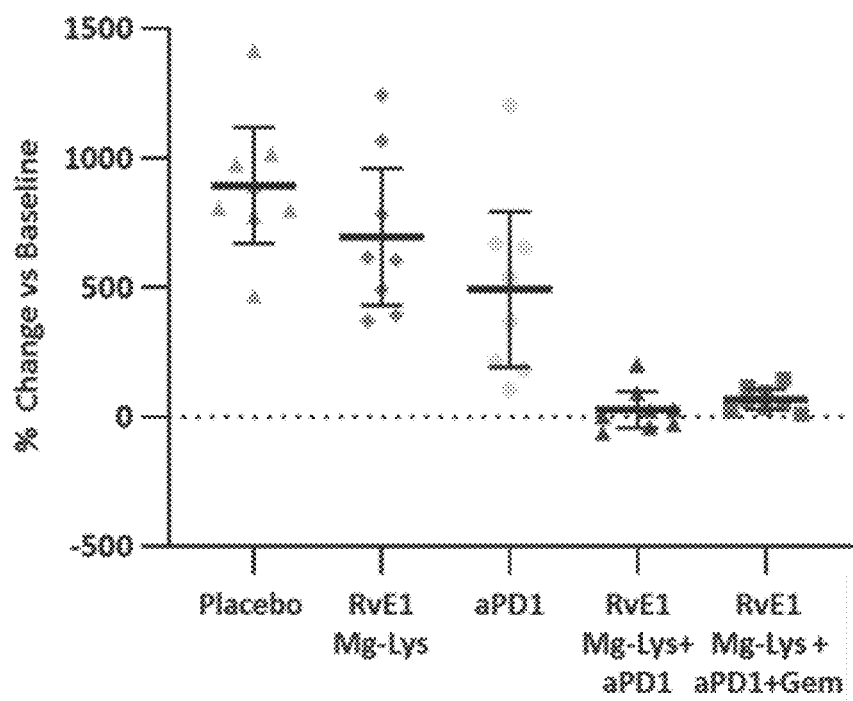
FIG. 2B is a scatter plot showing percent change in tumor volume (Day 15 vs Day 0) for bis RvE1 Mg-di-lysinate in the Panc2-H7 model of pancreatic cancer, with and without anti-PD1.

Example 2—Study of Bis RvE1 Mg-Di-Lysinate with Subcutaneous Administration in Combination with Anti-PD1 Therapy in the Panc2-H7 Model Over the last two decades, research on checkpoint inhibitors, including anti-PD(L)$_1$ and anti-CTLA4, has focused on T-cells as a major therapeutic target. Waldman et al., *Nat Rev Immunol.* 2020; 20(11):651-668. In general, the response to treatment with immune checkpoint inhibitors requires the presence of CD4+ and CD8+ T cells in the tumor microenvironment. Li et al., *Biochim Biophys Acta Rev Cancer.* 2020; 1874(2):188439. However, multiple studies demonstrate that resolvins prevent CD4+ T-cell activation, chemoattraction, and differentiation into Th1 and TH17 cells. Chiurchiu et al., *Sci. Transl. Med.* 2016; 8:353ra111; Mizraji et al., *Front Immunol.* 2018; 9:785; Oner et al., *Front Immunol.* 2021; 12:637983. In addition, resolvins can enhance the de novo generation and function of immunosuppressive T regulatory cells, which are associated with cancer progression and resistance to immune checkpoint inhibitors. Alvarez et al., *Front Immunol.* 2021; 12:664756; Togashi et al., *Nat Rev Clin Oncol* 2019; 16, 356-371. Contrary to the wide body of evidence suggesting that resolvins are likely to inhibit, or at least not enhance, the anti-tumor efficacy of immune checkpoint inhibitors, we found a strong effect with combination therapy of RvE1 and a murine anti-PD1 antibody (Bio X Cell CD279). Using the Panc2-H7 pancreatic cancer model system described above, a total of forty (40) C57BL/6J male mice were injected subcutaneously with 1×10e6 living Panc2-H7 cells. Once tumors reached 160-320 mm^3 in size, the mice were randomized (n=8 per group) to treatment with (i) vehicle, subcutaneous injection with (ii) bis RvE1 Mg-di-lysinate at 30 ug/kg or the murine anti-PD1 antibody (8 mg/kg, IP, Q3D), (iii) the double combination of bis RvE1 Mg-di-lysinate plus anti-PD1, or (iv) the triple combination of bis RvE1 Mg-di-lysinate, anti-PD1 and gemcitabine. As shown in FIG. 2A to FIG. 2B, monotherapy with either bis RvE1 Mg-di-lysinate or anti-PD1 did not have a significant anticancer effect in this model system. However, the combination arms significantly inhibited tumor growth relative to control (p<0.001 for bis RvE1 Mg-di-lysinate and anti-PD1 combination versus placebo and monotherapy groups). This was unexpected in view of the results of earlier independent studies with resolvins. Contrary to what was expected based on those studies, we found that combination therapy of resolvins and ICIs is a promising approach to treatment of pancreatic cancer.

Figure 3A:
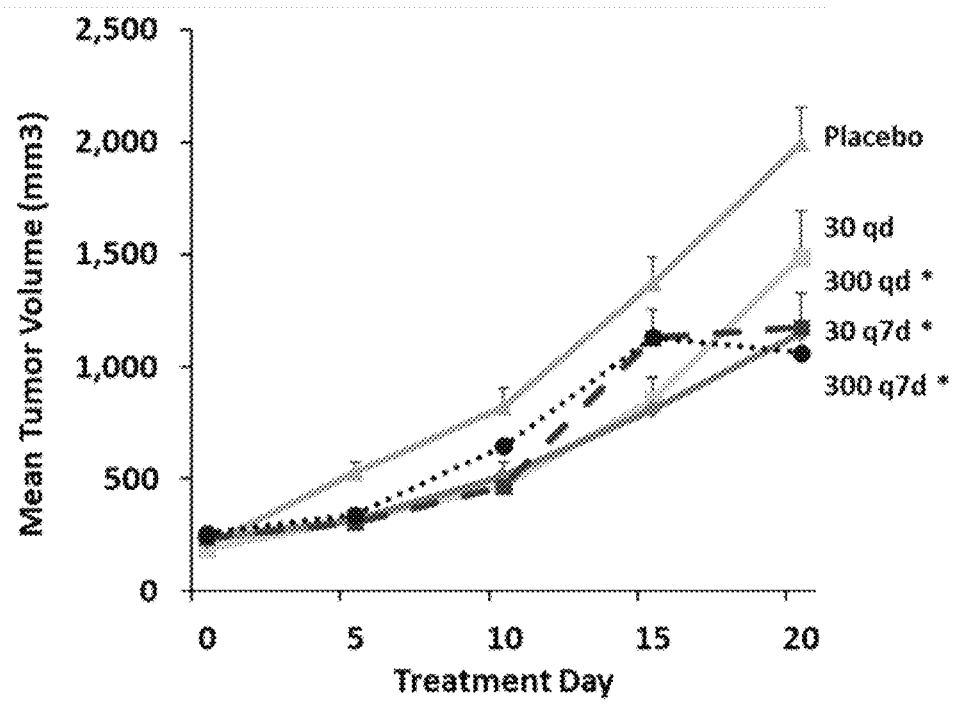
FIG. 3A is a line graph showing tumor volume over time (Day 20 vs Day 0) for bis RvE1 Mg-di-lysinate in the Panc2-H7 model with daily (QD) and weekly (Q7D) dosing.
Figure 3B:
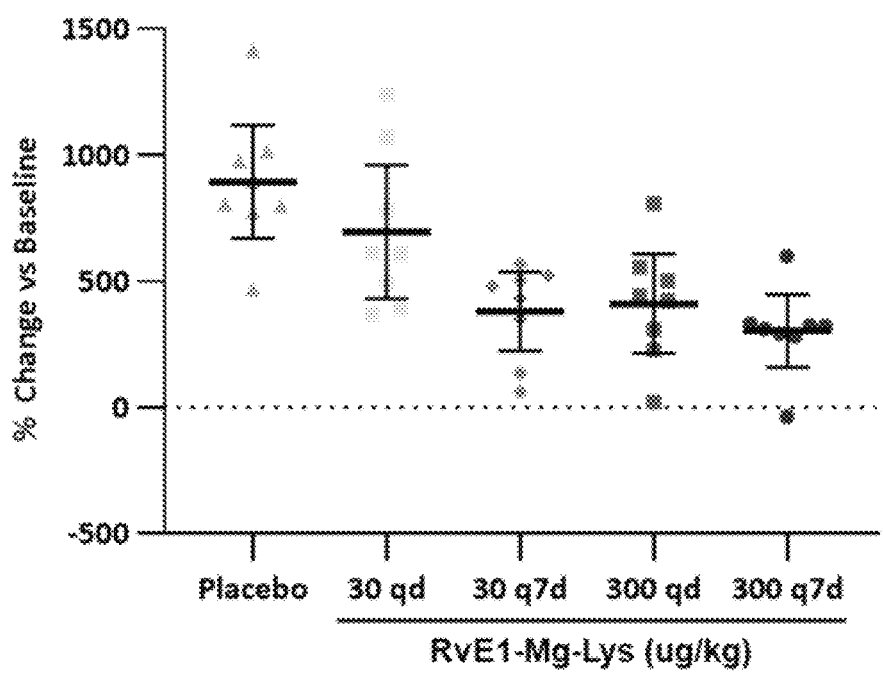
FIG. 3B is a scatter plot showing percent change in tumor volume (Day 20 vs Day 0) for bis RvE1 Mg-di-lysinate in the Panc2-H7 model with daily (QD) and weekly (Q7D) dosing.

Example 3—Comparison of Daily and Weekly Subcutaneous Administration of Bis RvE1 Mg-Di-Lysinate at Two Doses in the Panc2-H Model Based on the previous findings in the MC38 colorectal cancer model with less than daily (LTD) dosing, a study in the Panc2-H7 model was conducted to assess the efficacy of LTD dosing of bis RvE1 Mg-di-lysinate in a different tumor model. A total of forty (40) C57BL/6J male mice were injected subcutaneously with 1×10e6 living Panc2-H7 cells. Once tumors reached 160-320 mm^3 in size, the mice were randomized (n=8 per group) to treatment with vehicle or SC injection with bis RvE1 Mg-di-lysinate at 30 ug/kg and 300 ug/kg (QD, Q7D). As shown in FIG. 3A to FIG. 3B, bis RvE1 Mg-di-lysinate demonstrated inhibition relative to placebo control at the 30 and 300 ug/kg doses with both QD and Q7D dosing, with the greatest inhibition observed in the 300 ug/kg Q7D group (* P<0.05 vs placebo control). These results were consistent with the unexpected results observed in the MC38 model with LTD dosing, demonstrating that resolvins can be administered as infrequently as once per week and still exhibit potent anti-cancer activity. Based on these results, weekly (Q7D) dosing of bis RvE1 Mg-di-lysinate in combination with other therapies, or alone as maintenance therapy, could offer a substantial improvement in clinical therapy.

Figure 4A:
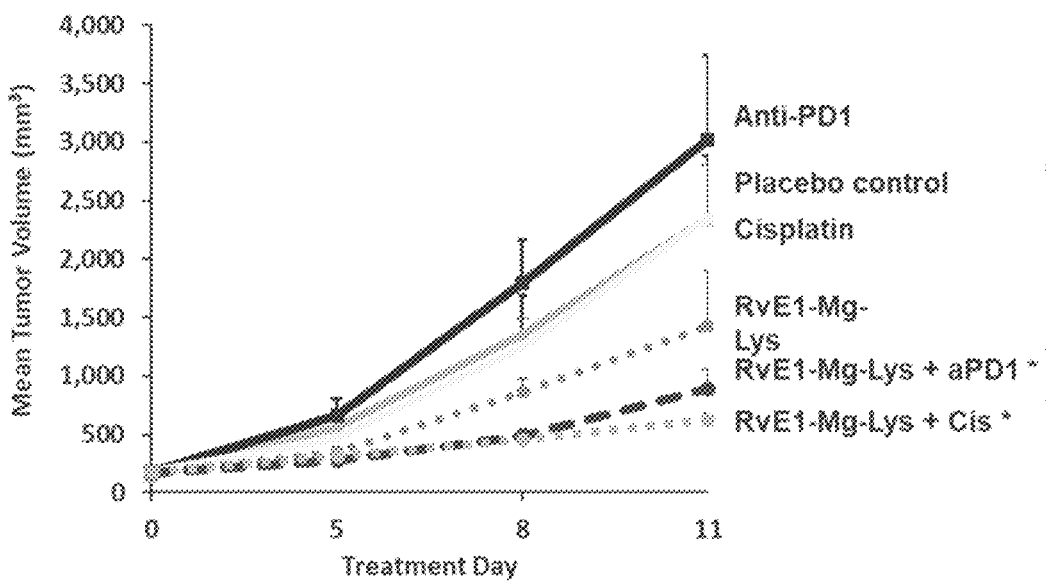
FIG. 4A is a line graph showing tumor volume over time (Day 11 vs Day 0) for bis RvE1 Mg-di-lysinate in the Lewis lung carcinoma model with and without anti-PD1 and cisplatin.
Figure 4B:
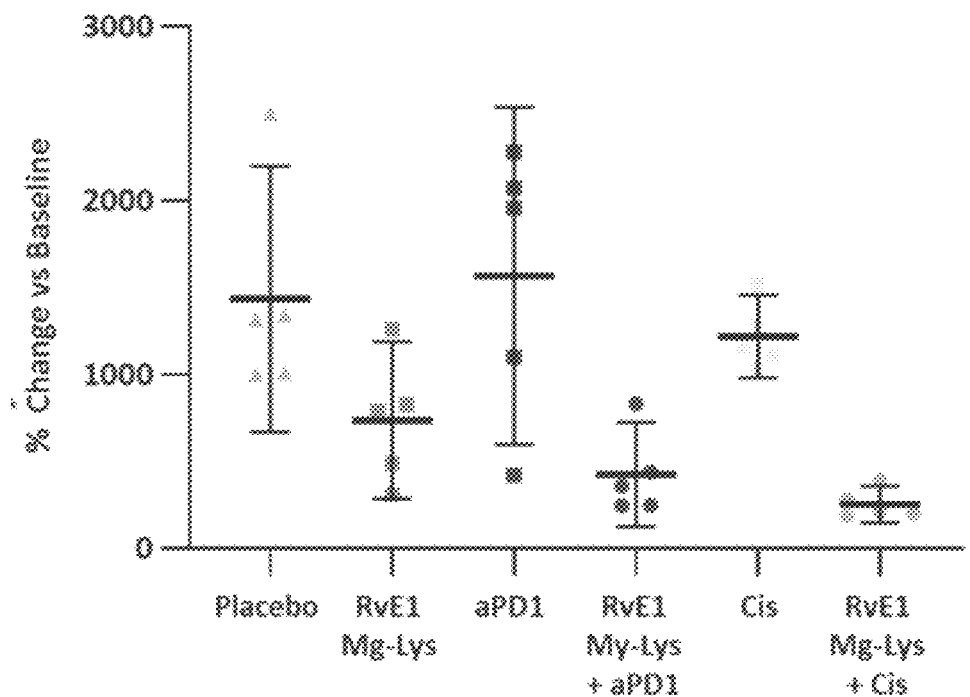
FIG. 4B is a scatter plot showing percent change in tumor volume (Day 11 vs Day 0) for bis RvE1 Mg-di-lysinate in the Lewis lung carcinoma model with and without anti-PD1 and cisplatin.

Example 4—Bis RvE1 Mg-Di-Lysinate Administered in Combination with Anti-PD1 or Cisplatin Therapy in the LLC Model To expand our understanding of bis RvE1 Mg-di-lysinate as a cancer therapy that could be used in combination with other cancer therapies including immune checkpoint inhibitors, bis RvE1 Mg-di-lysinate monotherapy and in combination either anti-PD1 or cisplatin was investigated in the LLC model of non-small cell lung cancer, which is a model known to unresponsive to anti-PD1 therapy and moderately responsive to cisplatin. Yu et al., *J Exp Clin Cancer Res.* 2010; 29(1):46; Lechner et al., *J Immunother.* 2013; 36(9): 477-489. A total of forty (40) C57BL/6J male mice were injected subcutaneously with 1×10e6 living LLC cells. Once tumors reached 150-200 mm^3 in size, the mice were randomized (n=5 per group) to treatment with vehicle, bis RvE1 Mg-di-lysinate (30 ug/kg, SC, QD), and anti-PD1 (8 mg/kg, IP, Q3D, Bio X Cell CD279) or cisplatin (5 mg/kg, i.p, Q5D). In addition, bis RvE1 Mg-di-lysinate was evaluated in combination with anti-PD1 or cisplatin. All mice were sacrificed on Day 11 when the average tumor size of the placebo group surpassed 2,000 mm^3. As shown in FIG. 4A to FIG. 4B, the bis RvE1 Mg-di-lysinate combinations with anti-PD1 and cisplatin reduced tumor volume compared to placebo and cisplatin and anti-PD1 alone (* P<0.05). Importantly, both anti-PD1 and cisplatin failed to demonstrate efficacy as monotherapy compared to placebo, suggesting that the combination with bis RvE1 Mg-di-lysinate is synergistic possibly by reprogramming the tumor microenvironment to make the tumors responsive to anti-PD-1 therapy and more responsive to cisplatin therapy.

Figure 5:
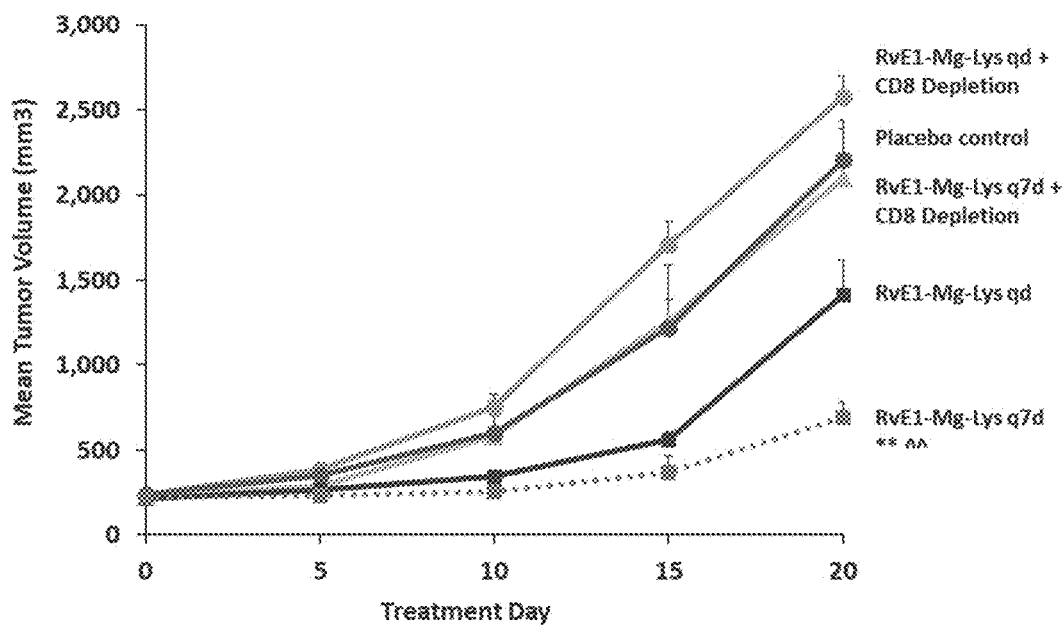
FIG. 5 is a line graph showing tumor volume over time for bis RvE1 Mg-di-lysinate in the Panc2-H7 model of pancreatic cancer with and without CD8 T-cell depletion.

Example 5—Bis RvE1 Mg-Di-Lysinate Administered with or without a CD8 Neutralizing Antibody in the Panc2-H7 Model Based on the findings with bis RvE1 Mg-di-lysinate administered in combination with anti-PD1 in two different tumor models (i.e., Panc2-H7 and LLC), daily (QD) and weekly (Q7D) dosing of bis RvE1 Mg-di-lysinate was investigated in the Panc2-H7 model, with and without an antibody that depletes CD8+ T-cells, which play a major role in the antitumor immune response of immune checkpoint inhibitors. A total of thirty (30) C57BL/6J male mice were injected subcutaneously with 1×10e6 living LLC cells. Once tumors reached 220-240 mm^3 in size based on mean tumor volume per cohort, the mice were randomized (n=6 per group) to treatment with vehicle, bis RvE1 Mg-di-lysinate (300 ug/kg, SC, QD or Q7D), with or without CD8 neutralizing antibody (200 ug IP Q3D). All mice were sacrificed on day 20 when the average tumor size of the placebo group exceeded 2,000 mm^3. As shown in FIG. 5, there were marked differences between the groups without and without the CD8 neutralizing antibody. The group treated with bis RvE1 Mg-di-lysinate at 300 ug/kg Q7D demonstrated significant inhibition compared to placebo control and compared to the same bis RvE1 Mg-di-lysinate dose regimen with the CD8 neutralizing antibody (** p<0.01 vs placebo, ^^<0.01 vs RvE1-Mg-Lys+CD8 depletion). These results provide strong evidence for the first time that the anti-cancer activity of Resolvin E1 is T-cell dependent, which is consistent with the observation of synergy when bis RvE1

Mg-di-lysinate is dosed in combination with anti-PD1 in tumor models that are resistant or non-responsive to anti-PD1 therapy, such as the LLC and Panc2 model systems. In addition, the results indicate that weekly (Q7D) subcutaneous dosing of bis RvE1 Mg-di-lysinate in mice not receiving the neutralizing antibody has comparable and possibly superior efficacy relative to daily (QD) dosing of bis RvE1 Mg-di-lysinate in mice not receiving the neutralizing antibody, which provides further evidence of the unexpected benefit of less than daily (LTD) dosing in general and weekly (Q7D) dosing in particular.

Figure 6:
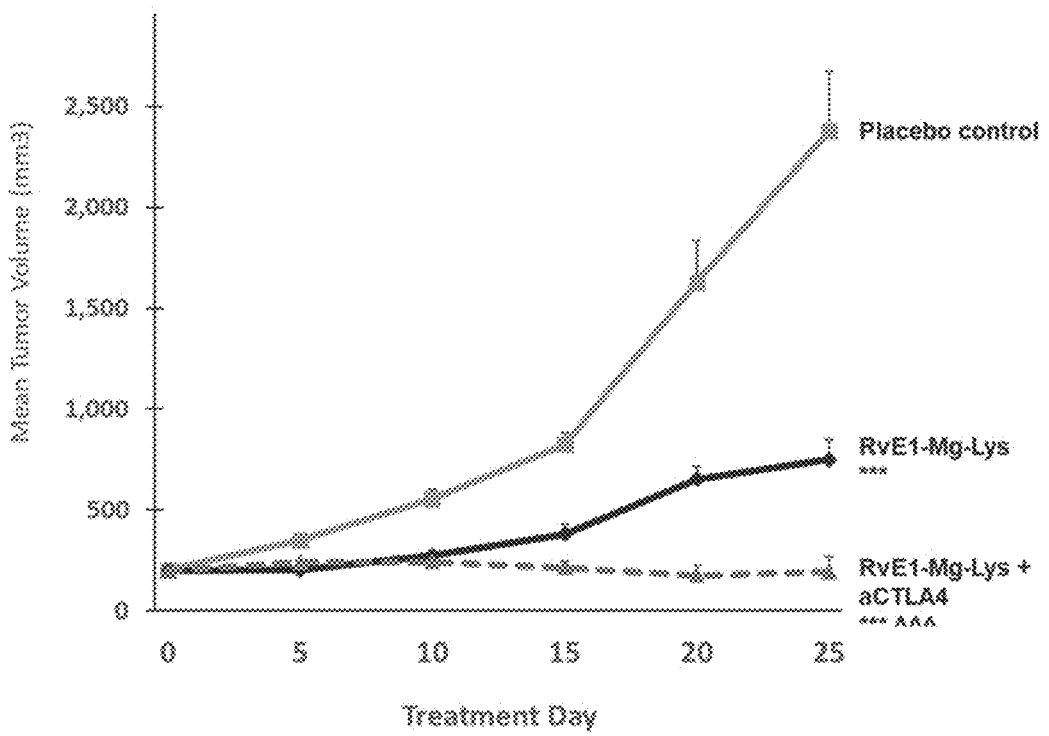
FIG. 6 is a line graph showing tumor volume over time for bis RvE1 Mg-di-lysinate in the Panc2-H7 model of pancreatic cancer with and without anti-CTLA4.

Example 6—Bis RvE1 Mg-Di-Lysinate Administered with or without Anti-CTLA4 in the Panc2-H7 Model To further corroborate the findings with weekly dosing of bis RvE1 Mg-di-lysinate and its efficacy in combination with immune checkpoint inhibitors (ICI), another study was conducted in the Panc2-H7 model with a different ICI. A total of twenty-four (24) C57BL/6J male mice were injected subcutaneously with 1×10e6 living Panc2 cells. Once tumors reached 200 mm^3 in size based on mean tumor volume per cohort, the mice were randomized (n=8 per group) to treatment with vehicle, bis RvE1 Mg-di-lysinate (300 ug/kg, SC, Q7D) and bis RvE1 Mg-di-lysinate+anti-CTLA-4 (4 mg/kg, i.p, first dose; 2 mg/kg i.p, Q3D following the first dose). As shown in FIG. 6, the combination of bis RvE1 Mg-di-lysinate and anti-CTLA-4 demonstrated significant inhibition related to both placebo and bis RvE1 Mg-di-lysinate alone (*** $p<0.001$ vs placebo, ^^^ $p<0.001$ vs bis RvE1 Mg-di-lysinate alone). In addition, bis RvE1 Mg-di-lysinate administered using weekly (Q7D) dosing demonstrated significant inhibition as monotherapy compared to placebo (*$p<0.0001$).

Figure 7A:
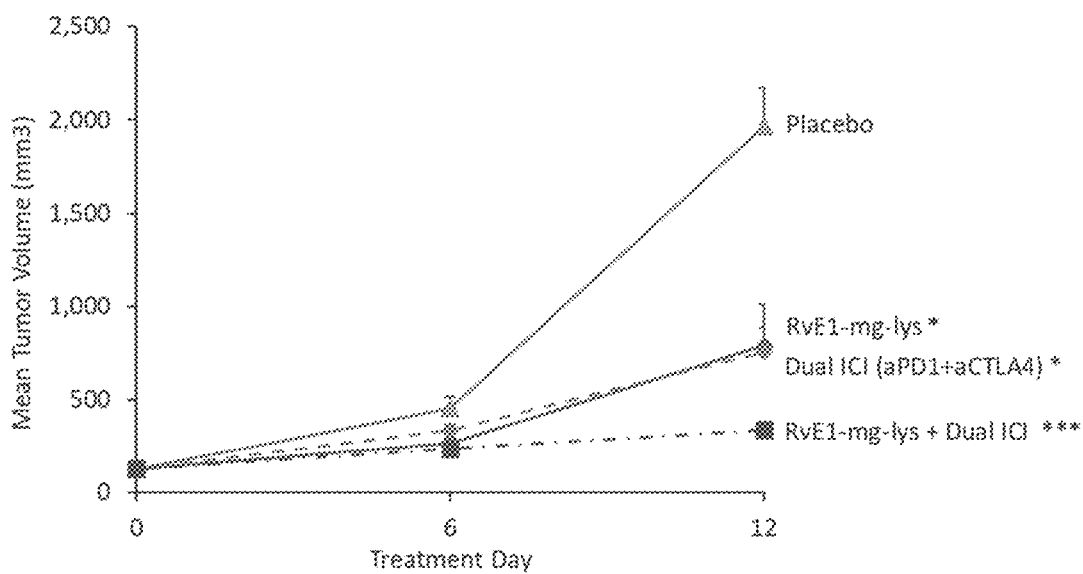
FIG. 7A is a line graph showing mean tumor volume over time for bis RvE1 Mg-di-lysinate in the B16F10 model of melanoma either alone or in combination with anti-PD1 and anti-CTLA4 immunotherapies ("dual ICI"), as compared to placebo and dual ICI alone.
Figure 7B:
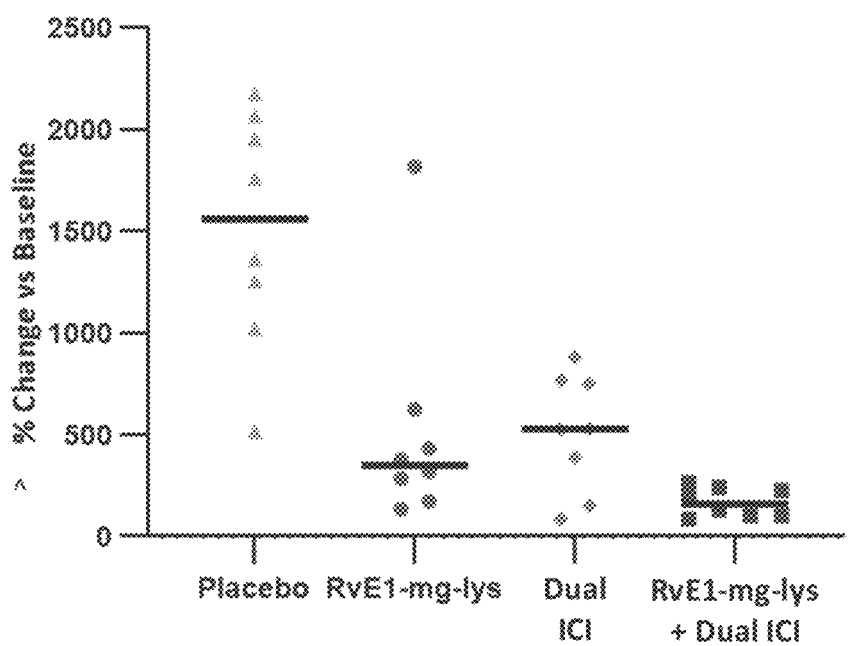
FIG. 7B is a scatter plot showing percent change in tumor volume (Day 12 vs Day 0) for the treatment arms in FIG. 7B.

Example 7—Bis RvE1 Mg-Di-Lysinate Administered in Combination with Anti-CTLA4 and Anti-PD1 in the B16F10 Model of Melanoma Based on the finding of increased efficacy with bis RvE1 Mg-di-lysinate administered in combination with anti-PD1 monotherapy and anti-CTLA4 monotherapy, a study was conducted to investigate the efficacy of less than daily (LTD) bis RvE1 Mg-di-lysinate combined with both anti-PD1 and anti-CTLA4 in the B16F10 model of melanoma. This approach could be clinically relevant because dual checkpoint inhibition with anti-PD1 and anti-CTLA4 has demonstrated enhanced efficacy over ICI monotherapy but leads to a higher rate of immune-related adverse events (IRAEs), necessitating a reduction in the dose of anti-CTLA4. See Perez-Ruiz E, et al. Nature. 2019; 569(7756):428-432. Thus, this initial study with ICI dual therapy was designed to investigate whether use of bis RvE1 Mg-di-lysinate with the ICI dual therapy could enhance efficacy, which may offer the opportunity to reduce the dose of the ICI components of the regimen without loss of efficacy. A total of sixty-four (64) C57BL/6J male mice were injected subcutaneously with 1×10e6 living B16F10 cells in the dorsum. When tumors reached a mean tumor volume of approximately 130 mme3, the mice were randomized (n=8 per group) to treatment with vehicle, bis RvE1 Mg-di-lysinate (300 ug/kg, SC, Q6D), anti-PD1 (8 mg/kg, i.p., Q3D) or anti-CTLA-4 (4 mg/kg, Q3D). The double combinations of bis RvE1 Mg-di-lysinate and anti-CTLA-4 or anti-PD1, and anti-PD1 with anti-CTLA-4, as well as the triple combination of bis RvE1 Mg-di-lysinate, anti-CTLA-4 and anti-PD1 were also investigated. All combination arms used the same dosing regimens as the individual monotherapies. The mice were sacrificed on day 12 per protocol when the mean tumor of the vehicle group reached approximately 2,000 mm$^3$. As shown in FIG. 7A and FIG. 7B, triple therapy (bis RvE1 Mg-di-lysinate+anti-CTLA-4 and anti-PD1, referred to in the figure as "RvE1 Mg-di-lysinate Dual ICI" demonstrated significant inhibition (67%) measured in terms of tumor volume at day 12 divided by tumor volume at day 0 ($p<0.05$). Triple therapy also demonstrated significant tumor growth inhibition compared to anti-CTLA-4 monotherapy (71%), and anti-PD1 monotherapy (87%) (*** $p<0.001$). Importantly, triple therapy also reduced variability compared to all other groups including ICI dual therapy (Standard error of the mean (SEM)=25% for triple therapy; SEM=102% for anti-PD1 and anti-CTLA-4 dual therapy). Importantly, the double combination of bis RvE1 Mg-di-lysinate and anti-PD1 also demonstrated significant inhibition compared to anti-PD1 monotherapy (54%) (* $p<0.05$). This is clinically relevant for melanoma patients receiving anti-PD1 monotherapy, which is used when the side effects of ICI dual therapy are not tolerated. In summary, this study provides further evidence that bis RvE1 Mg-di-lysinate enhances the efficacy of immunotherapy and that LTD dosing of bis RvE1 Mg-di-lysinate is effective as monotherapy and in combination with ICI monotherapy or ICI dual therapy.

Figure 8A:
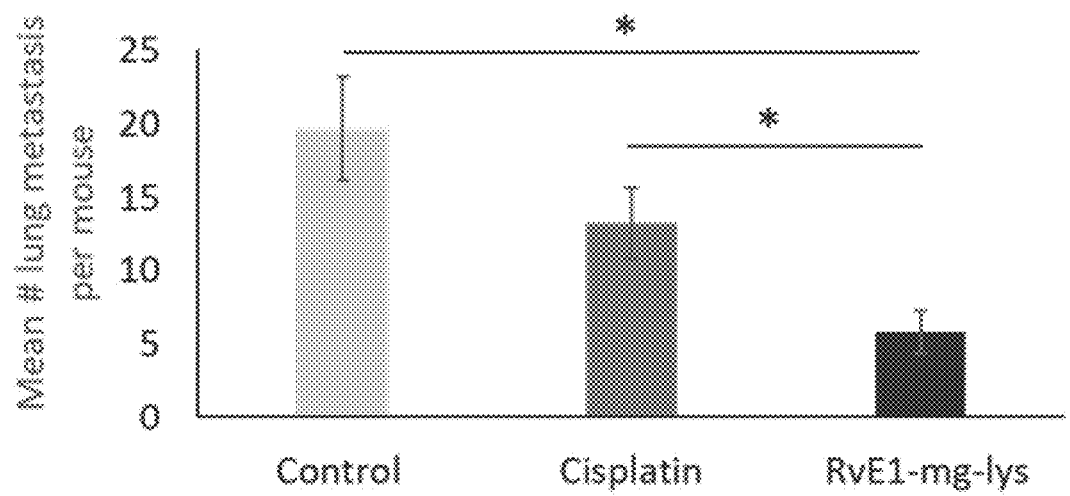
FIG. 8A is a bar graph showing mean number of lung metastases (Day 12) in the metastatic LLC resection model for bis RvE1 Mg-di-lysinate administered in the perioperative period compared to cisplatin and vehicle control.
Figure 8B:
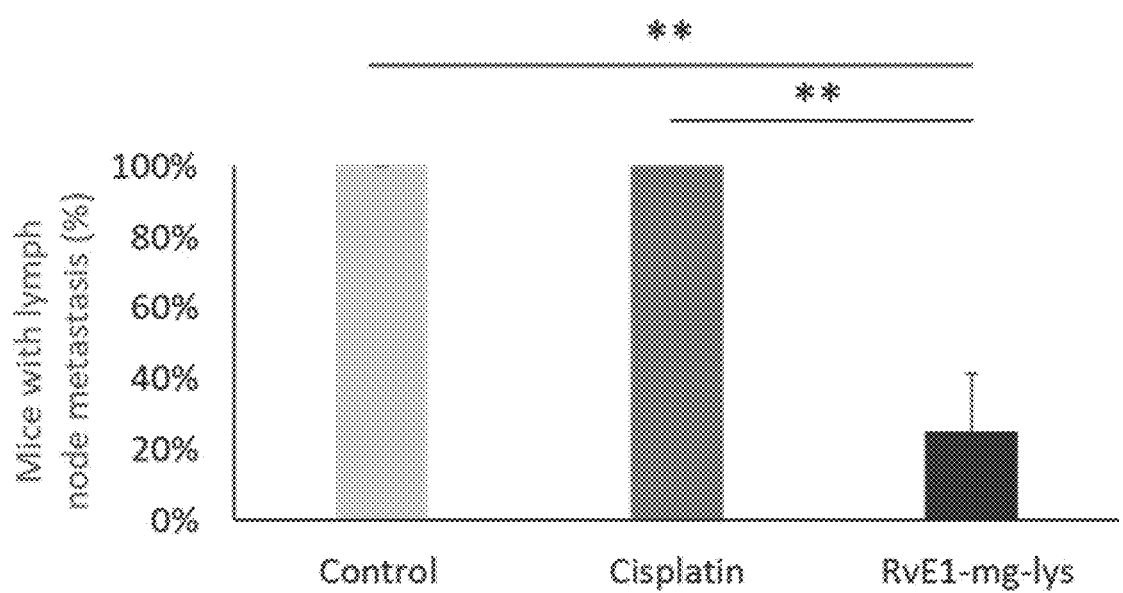
FIG. 8B is a bar graph showing percent of mice with lymph node metastases (Day 12) in the metastatic LLC resection model for bis RvE1 Mg-di-lysinate administered in the perioperative period compared to cisplatin and vehicle control.

Example 8—Investigation of Neo-Adjuvant Bis RvE1 Mg-Di-Lysinate with LTD Administration in the Lewis Lung Carcinoma (LLC) Resection Tumor Model To investigate the efficacy of LTD dosing of bis RvE1 Mg-di-lysinate as neo-adjuvant therapy, a study was conducted in the metastatic LLC resection model with treatment initiated in the perioperative window. A total of fifteen (15) C57BL/6J male mice were injected subcutaneously with 1×10e6 living LLC cells. Once tumors reached approximately 1200-1500 mme3 in size, the mice were randomized (n=4-8 per group) to treatment with vehicle (SC, Q6D), bis RvE1 Mg-di-lysinate (300 ug/kg, SC, Q6D), or cisplatin (5 mg/kg, i.p, Q6D), followed by surgical resection of the tumors. The mice in the vehicle and cisplatin groups received an initial dose twenty-four (24) hours prior to surgery, and the mice treated with bis RvE1 Mg-di-lysinate received an initial dose two (2) hours prior to surgery. All mice were sacrificed on day 19 following the death of three mice in the vehicle control group on day 18. As shown in FIG. 8A, treatment with Q6D bis RvE1 Mg-di-lysinate significantly reduced the number of lung metastases compared to vehicle control and cisplatin (*$p<0.05$). As shown in FIG. 8B, treatment with Q6D bis RvE1 Mg-di-lysinate significantly reduced the number of mice with metastasis in the axillary or inguinal lymph nodes compared to mice receiving vehicle or cisplatin (** $p<0.01$). In addition, cisplatin, which is used extensively to treat lung cancer as adjuvant therapy, failed to show a significant reduction in the number of lung metastases or the number of mice with lymph node metastasis compared to vehicle control.

Example 9—Bis RvE1 Mg-Di-Lysinate Administered in Combination with Gemcitabine Therapy in the KPC Orthotopic Model To expand our understanding of less than daily (LTD) dosing of bis RvE1 Mg-di-lysinate as a cancer therapy that could be used in combination with chemotherapy, bis RvE1

Figure 9:
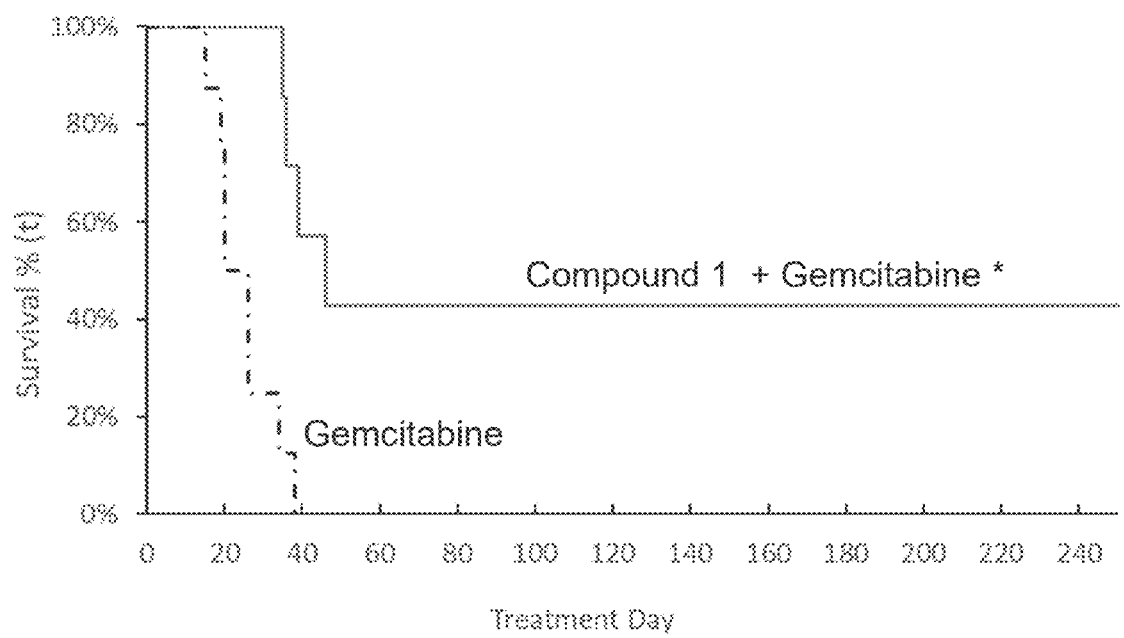
FIG. 9 is a line graph showing mouse survival for bis RvE1 Mg-di-lysinate (Compound 1) administered Q6D with and without gemcitabine in the orthotopic KPC model.

Mg-di-lysinate (Compound 1) was investigated in the orthotopic KPC model of pancreatic cancer. A total of fifteen (15) C57BL/6J male mice were implanted orthotopically with 5×10e5 living KPC cells into the pancreas. The mice were randomized (n=7-8) to treatment with bis RvE1 Mg-di-lysinate (300 ug/kg, SC, Q6D) with or without gemcitabine (50 mg/kg, IP, Q3D, up to 6 doses) one day after tumor cell implantation. As shown in FIG. 9, the bis RvE1 Mg-di-lysinate combination with gemcitabine had a mean survival of 129 days versus 25 days for gemcitabine monotherapy, which corresponds to a four-fold increase in survival (* p<0.05). In addition, three of the seven mice (43%) in the combination group were alive as of the last observation (day 250) versus zero of eight mice in the gemcitabine monotherapy group.

Example 10—RvE1 Pharmacokinetics in Mice

Figure 10A:
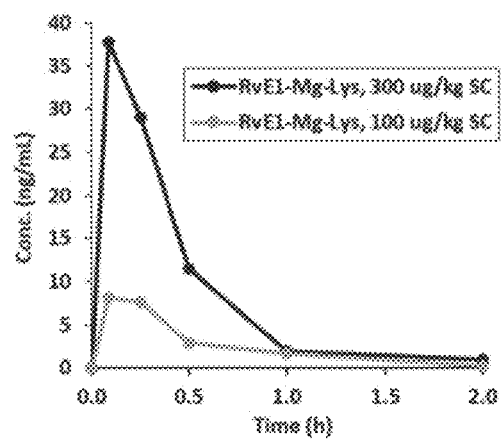
FIG. 10A is a line graph showing plasma levels of RvE1 over time in mice following subcutaneous dosing with bis RvE1 Mg-di-lysinate.
Figure 10B:
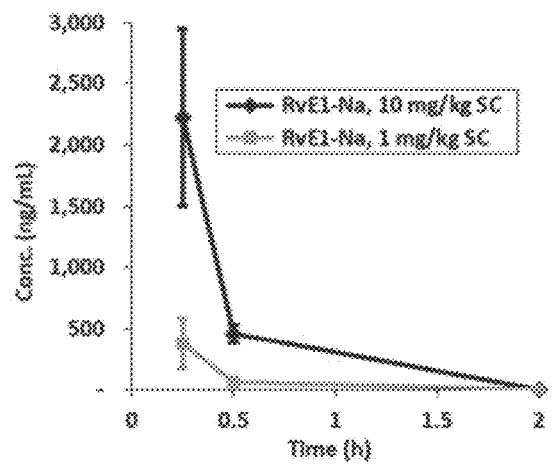
FIG. 10B is a line graph showing plasma levels of RvE1 over time in mice following subcutaneous dosing with RvE1-Na.
Figure 10C:
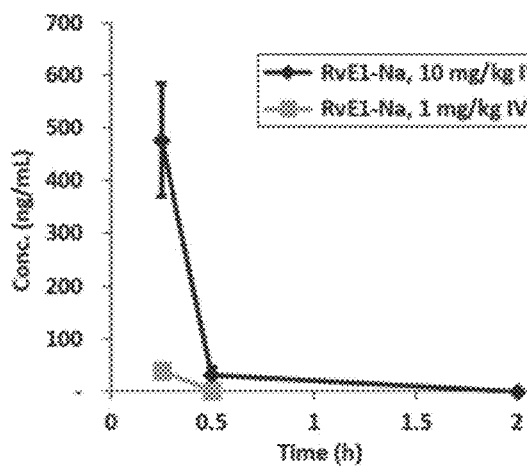
FIG. 10C is a line graph showing plasma levels of RvE1 over time in mice following intravenous dosing with RvE1-Na.
Figure 10D:
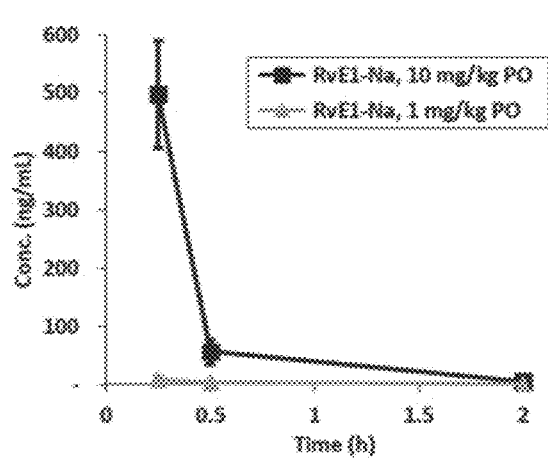
FIG. 10D is a line graph showing plasma levels of RvE1 over time in mice following oral dosing with RvE1-Na.
Figure 10F:
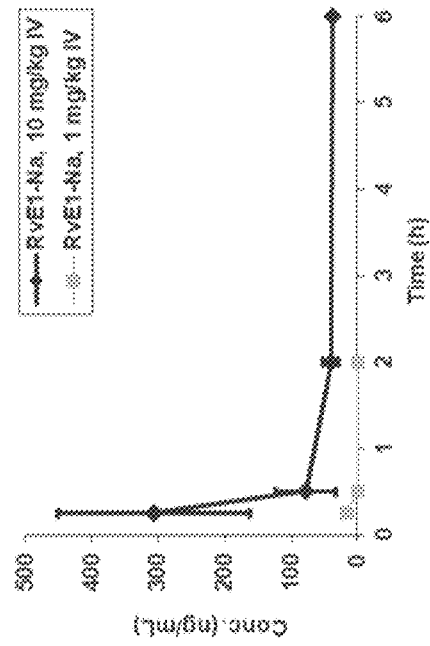
FIG. 10F is a line graph showing lung tissue levels of RvE1 over time in mice following intravenous dosing with RvE1-Na.
Figure 10E:
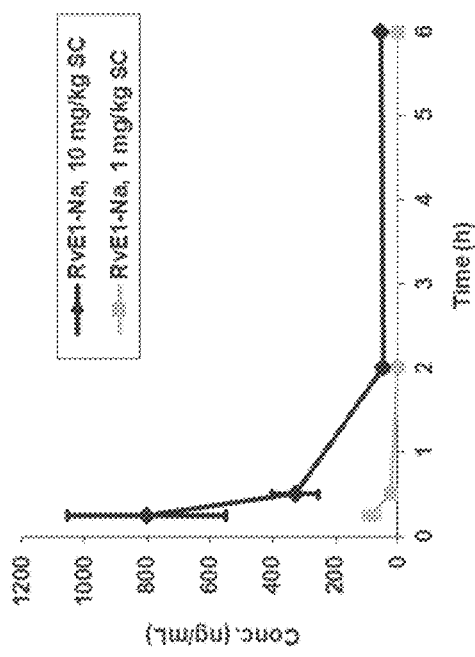
FIG. 10E is a line graph showing lung tissue levels of RvE1 over time in mice following subcutaneous dosing with RvE1-Na.
Figure 10G:
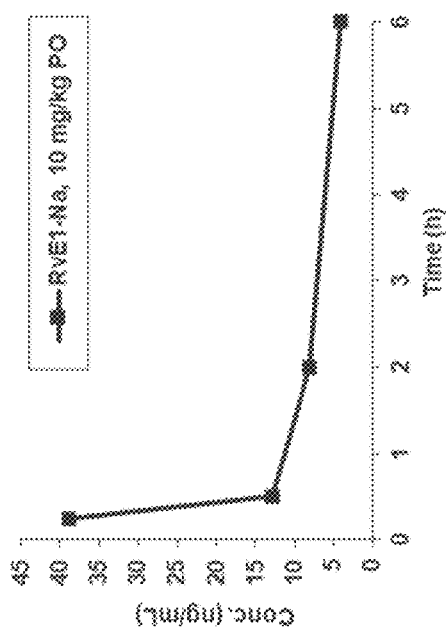
FIG. 10G is a line graph showing lung tissue levels of RvE1 over time in mice following oral dosing with RvE1-Na.

Pharmacokinetic (PK) studies with subcutaneous (FIG. 10A FIG. 10B, FIG. 10E) intravenous (FIG. 10C, FIG. 10F), and oral administration (FIG. 10D, FIG. 10G) of salt forms of RvE1 show rapid depletion of RvE1 from plasma and organ tissues. In the subcutaneous PK study, sixty-nine (69) C57BL/6J mice were administered 100 or 300 ug/kg doses of RvE1-Mg-Lys via subcutaneous injection. Mice were sacrificed and plasma was drawn at the following timepoints: baseline, 5, 15, 30 min, 1, 2, 4 and 8 hours (n=5 mice per timepoint). In the IV and oral PK studies, one-hundred eighty (180) Balb/c mice were administered RvE1-Na at 1 or 10 mg/kg via subcutaneous injection, IV injection, oral gavage (n=6 mice per timepoint). Plasma and lung tissue were assayed at the following timepoints: 0.25, 0.5, 1, 2, 6, 10 and 24 hours. Across multiple routes of administration, salts of RvE1 exhibit a short biological half-life that is consistent with prior studies reporting that resolvins, including RvE1, are rapidly metabolized and cleared from systemic circulation and tissue. Collectively, these PK data suggest that administration of resolvins in a less than daily (LTD) dosing regimen is unlikely to be effective therapeutically, or at least that it is unlikely to be as effective as daily or more frequent dosing or continuous infusion. Without being bound by any theory, the surprising efficacy of LTD dosing of resolvins in the cancer model systems described here may be the result of durable effects on the tumor microenvironment including changes in immune cell phenotype, vascularization, stromal phenotype, and antigen presentation, as well as durable effects on the T-cell compartment such as T-cell priming and increased tumor-infiltrating lymphocytes.

Figure 11:
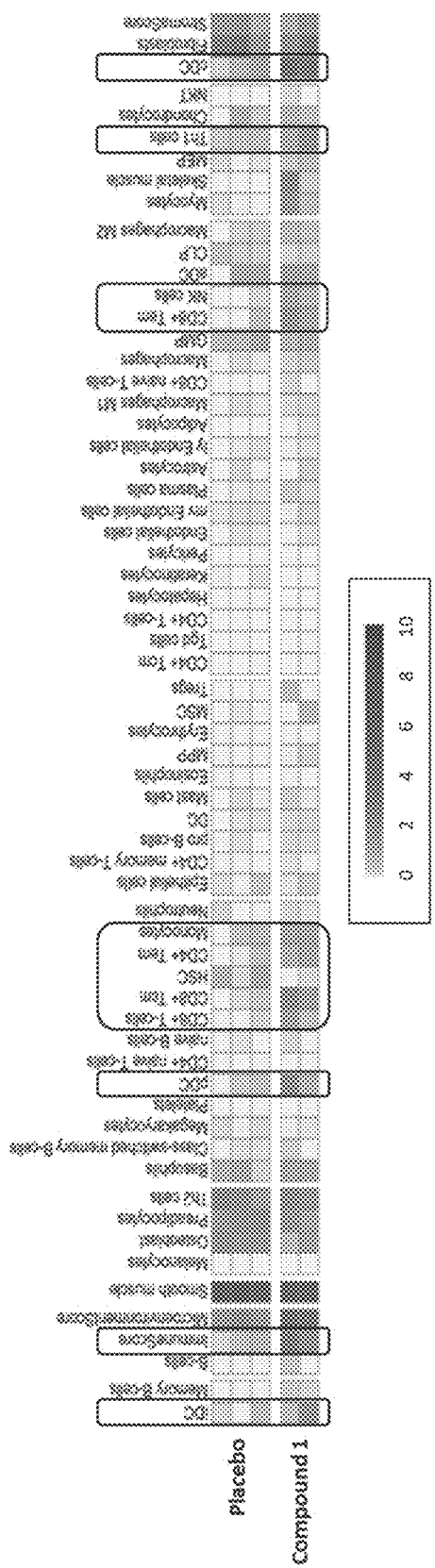
FIG. 11 is a heat map showing activation of adaptive immune response in T cells and other immune cells in pancreatic tumors following treatment with bis RvE1 Mg-di-lysinate.

Example 11—Cell Enrichment Analysis Shows Modulation of Adaptive Immune Response in Pancreatic Cancer RNAseq analysis was performed on tumor samples from mice with subcutaneous KPC tumors sacrificed on Day 26 following treatment (Q6D) with bis RvE1 Mg-di-lysinate (Compound 1) compared to placebo. FIG. 11 shows a heatmap of gene expression for placebo treated mice and mice treated with Compound 1. Darker color indicates increased gene expression, for various immune cells and other cells, as listed across the top of the heatmap. The boxed cells shown in FIG. 11 indicate an increase in markers of monocytes and DC cell subset (cDCs, pDCs, and iDCs) and markers of NK, CD8+ T cells, Th1 cells, and memory T cells (CD8+ and CD4+) with Compound 1 treatment. These data support a general mechanism for the surprising efficacy of the resolvins in the cancer model systems described above. Namely, these unexpected results may be due to durable effects on the tumor microenvironment including changes in immune cell phenotype and the T-cell compartment such as T-cell priming and increased tumor-infiltrating lymphocytes.

The structures of exemplary compounds of Formulas I and IV are shown below in Table 11. The compounds can be synthesized, for example, as described in U.S. Pat. No. 10,420,843, which is incorporated herein by reference in its entirety. Alternate methods for obtaining the SPM component of a compound described here are described, for example, in Li et al., *Beilstein J. Org. Chem.* 2013, 9, 2762-2766 and Vik et al., *Bioorganic and Med. Chem. Let* 2017. In addition, one or more SPMs for use in the SPM component of a compound described here may be available for purchase from a vendor such as Caymen Chemical Co. (Ann Arbor, MI).

TABLE 13

Structures of Representative Compounds of Formulas I and IV

| Name | Structure |
|---|---|
| RvE1-MgLys Compound 1 | (chemical structure of RvE1 with OH, OH, OH substituents and $CO_2^-$ group; accompanied by magnesium dilysinate complex structure with $(CH_2)_4NH_3^+$ and $^+H_3N(H_2C)_4$ groups coordinated to Mg via N and O atoms) |

TABLE 13-continued

Structures of Representative Compounds of Formulas I and IV

| Name | Structure |
|---|---|
| RvE1-CaLys Compound 2 | 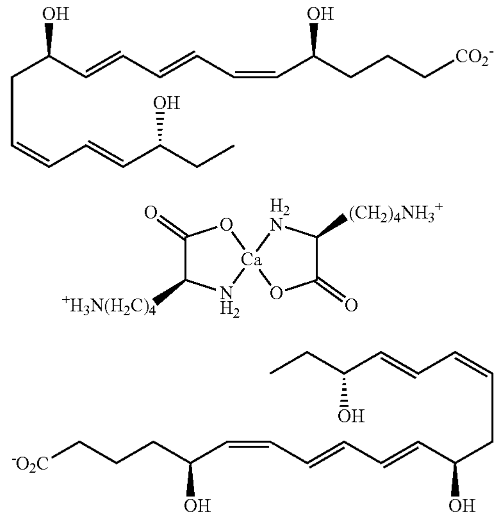 |
| RvE1-ZnLys Compound 3 | 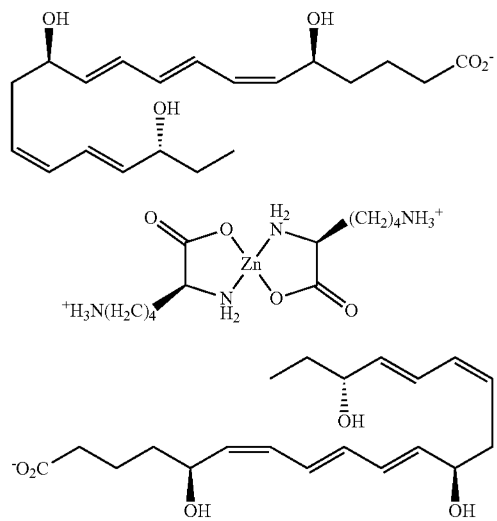 |
| RvE1-LysLys Compound 4 | 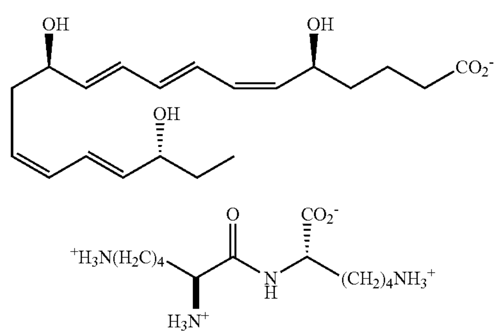 |

TABLE 13-continued

Structures of Representative Compounds of Formulas I and IV

| Name | Structure |
|---|---|
| RvE1-LysLys (linear) Compound 5 | (chemical structure) |
| AT(18S)-RvE1-MgLys Compound 6 | (chemical structure) |
| AT(18S)-RvE1-CaLys Compound 7 | (chemical structure) |

TABLE 13-continued

Structures of Representative Compounds of Formulas I and IV

| Name | Structure |
| --- | --- |
| AT(18S)-RvE1-ZnLys Compound 8 | (structures of polyhydroxy polyunsaturated fatty acid carboxylate with Zn-bis(lysinate) complex) |
| AT(18S)-RvE1-LysLys Compound 9 | (structures of polyhydroxy polyunsaturated fatty acid carboxylate with Lys-Lys dipeptide, α-linked) |
| AT(18S)-RvE1-LysLys (linear) Compound 10 | (structures of polyhydroxy polyunsaturated fatty acid carboxylate with Lys-Lys dipeptide, ε-linked linear) |

TABLE 13-continued

Structures of Representative Compounds of Formulas I and IV

| Name | Structure |
|---|---|
| | [chemical structure] |
| RvD1-MgLys Compound 11 | [chemical structure with Mg complex] |
| RvD1-CaLys Compound 12 | [chemical structure with Ca complex] |

TABLE 13-continued
Structures of Representative Compounds of Formulas I and IV
| Name | Structure |
|---|---|
| RvD1-ZnLys Compound 13 | 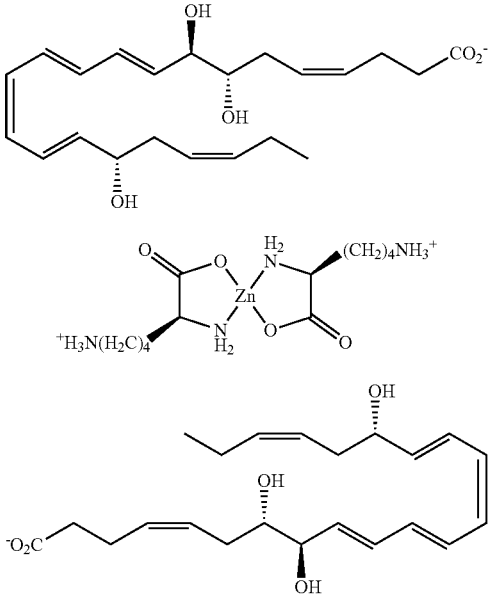 |
| RvD1-LysLys Compound 14 | 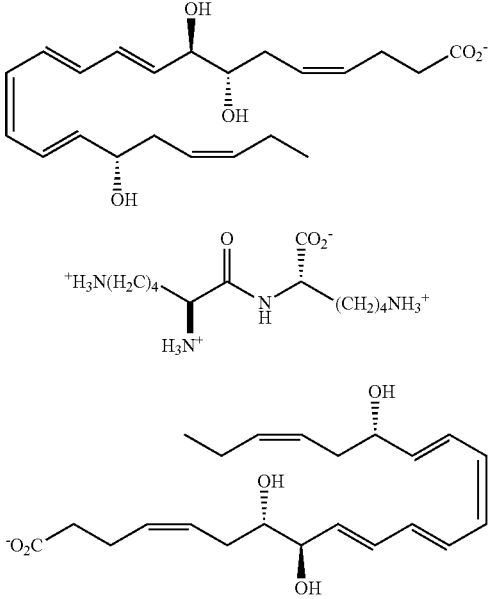 |
| RvD1-LysLys (linear) Compound 15 | 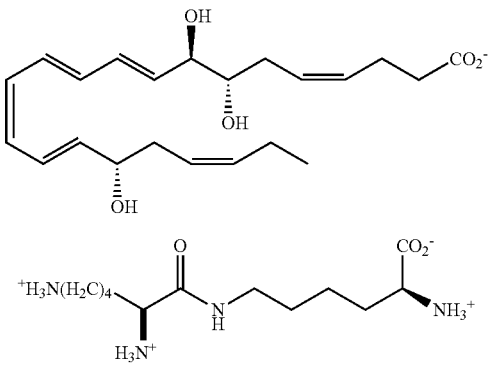 |

TABLE 13-continued

Structures of Representative Compounds of Formulas I and IV

| Name | Structure |
|---|---|
| | (chemical structure) |
| AT(17e)-RvD1-MgLys Compound 16 | (chemical structures, including Mg complex with two lysine ligands) |
| AT(17e)-RvD1-CaLys Compound 17 | (chemical structures, including Ca complex with two lysine ligands) |

TABLE 13-continued
Structures of Representative Compounds of Formulas I and IV
| Name | Structure |
| --- | --- |
| AT(17e)-RvD1-CaLys Compound 18 | 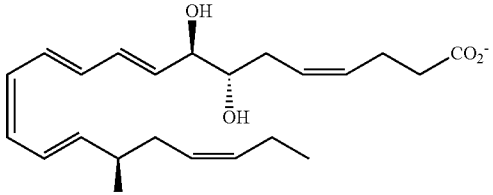 |
| AT(17e) RvD1-LysLys Compound 19 | 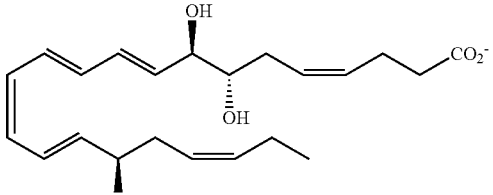 |
| AT(17e)-RvD1-LysLys (linear) Compound 20 | 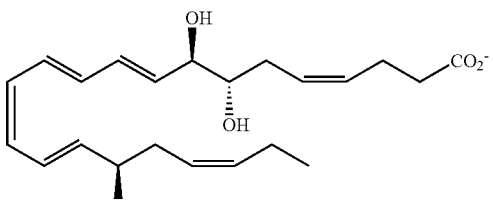 |

TABLE 13-continued

Structures of Representative Compounds of Formulas I and IV

| Name | Structure |
| --- | --- |
| | (structure) |
| RvD2-MgLys Compound 21 | (structures) |
| RvD2-CaLys Compound 22 | (structures) |

TABLE 13-continued
Structures of Representative Compounds of Formulas I and IV
| Name | Structure |
| --- | --- |
| RvD2-ZnLys Compound 23 | 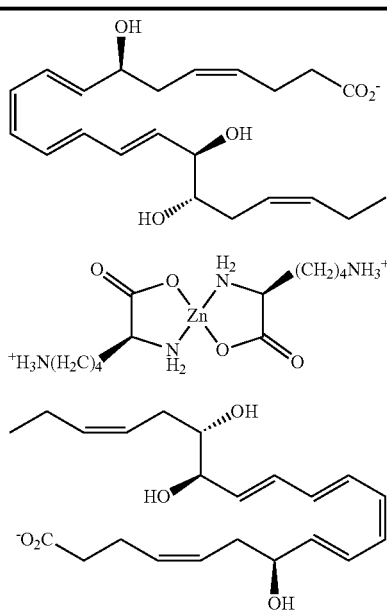 |
| RvD2-LysLys Compound 24 | 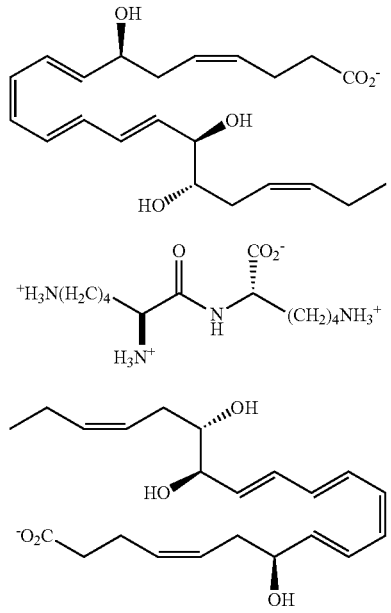 |
| RvD2-LysLys (linear) Compound 25 | 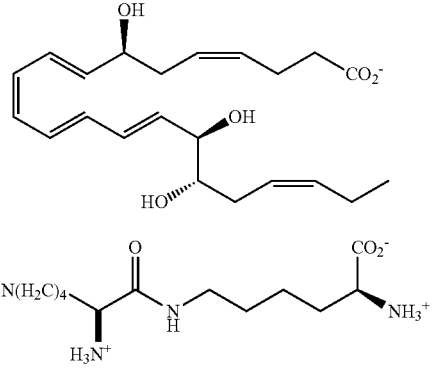 |

TABLE 13-continued

Structures of Representative Compounds of Formulas I and IV

| Name | Structure |
| --- | --- |
| | (structure) |
| RvE2-MgLys Compound 26 | (structure with Mg complex) |
| RvE2-CaLys Compound 27 | (structure with Ca complex) |
| RvE2-ZnLys Compound 28 | (structure) |

TABLE 13-continued
Structures of Representative Compounds of Formulas I and IV
| Name | Structure |
|---|---|
| | 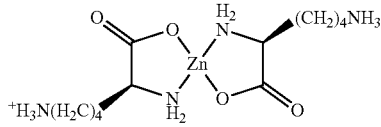 |
| RvE2-LysLys Compound 29 | 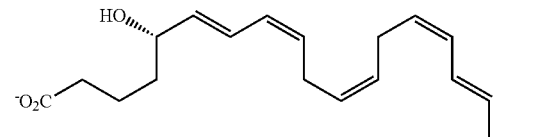 |
| RvE2-LysLys (linear) Compound 30 | 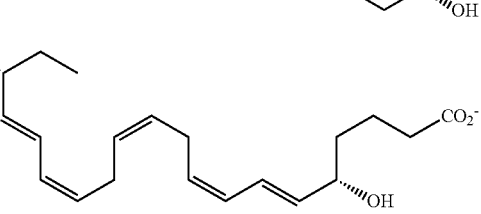 |
| AT-RvE2-MgLys Compound 31 | 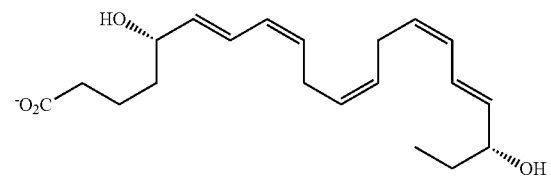 |

TABLE 13-continued
Structures of Representative Compounds of Formulas I and IV
| Name | Structure |
|---|---|
| AT-RvE2-CaLys Compound 32 | 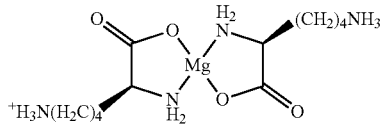 |
| AT-RvE2-ZnLys Compound 33 | 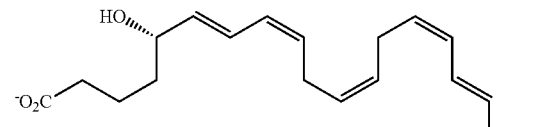 |
| AT-RvE2-LysLys Compound 34 | 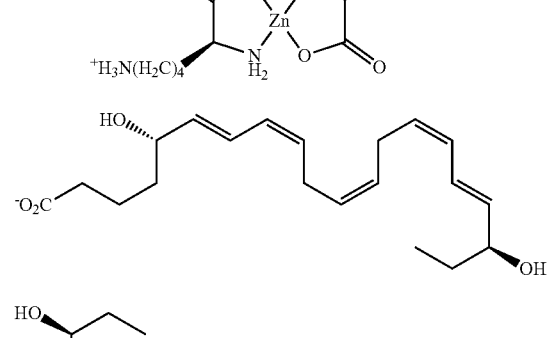 |

TABLE 13-continued

Structures of Representative Compounds of Formulas I and IV

| Name | Structure |
|---|---|
| AT-RvE2-LysLys (linear) Compound 35 | |
| RvE3-MgLys Compound 36 | |
| RvE3-CaLys Compound 37 | 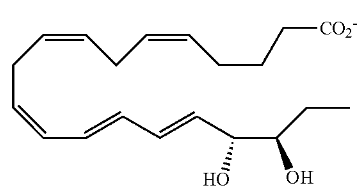 |

TABLE 13-continued
Structures of Representative Compounds of Formulas I and IV
| Name | Structure |
|---|---|
| RvE3-ZnLys Compound 38 | 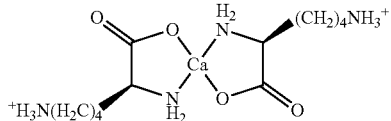 |
| RvE3-LysLys Compound 39 | 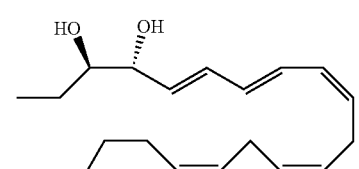 |
| RvE3-LysLys (linear) Compound 40 | 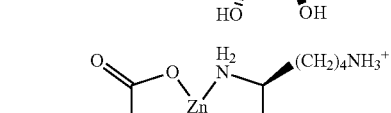 |

TABLE 13-continued

Structures of Representative Compounds of Formulas I and IV

| Name | Structure |
|---|---|

AT-RvE3-MgLys Compound 41

AT-RvE3-CaLys Compound 42

AT-RvE3-ZnLys Compound 43

TABLE 13-continued
Structures of Representative Compounds of Formulas I and IV
| Name | Structure |
|---|---|
| AT-RvE3-LysLys Compound 44 | 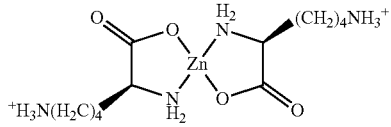 |
| AT-RvE3-LysLys (linear) Compound 45 | 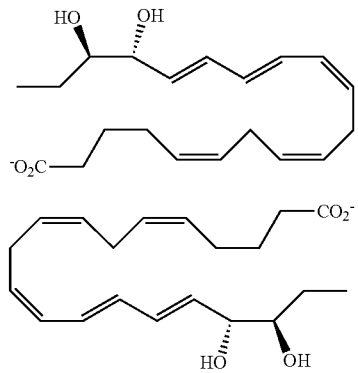 |
| RvE4-MgLys Compound 46 | 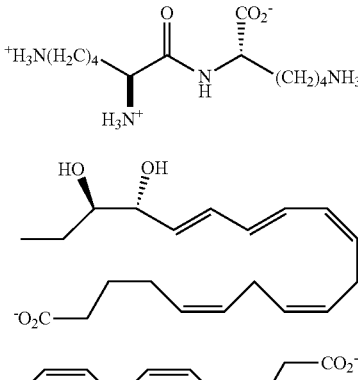 |

TABLE 13-continued

Structures of Representative Compounds of Formulas I and IV

| Name | Structure |
|---|---|
| | 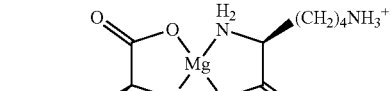 |
| RvE4-CaLys Compound 47 | 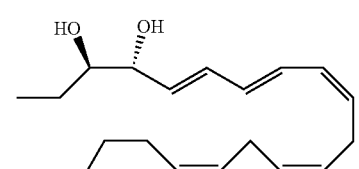 |
| RvE4-ZnLys Compound 48 | 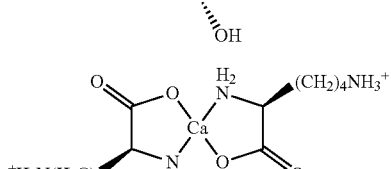 |

EQUIVALENTS

Those skilled in the art will recognize or be able to ascertain using no more than routine experimentation, many equivalents to the specific embodiments of the invention described herein. Such equivalents are intended to be encompassed by the following claims.

All references cited herein are incorporated herein by reference in their entirety and for all purposes to the same extent as if each individual publication or patent or patent application was specifically and individually indicated to be incorporated by reference in its entirety for all purposes.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

What is claimed is:

1. A method for treating cancer in a subject in need of such treatment, the method comprising administering to the subject a pharmaceutical composition comprising a mineral amino acid salt of resolvin E1 ("RvE1") in a therapeutic regimen of every six days (Q6D) or every seven days (Q7D), either alone as monotherapy or as adjuvant or neo-adjuvant therapy, optionally in combination with one or more additional therapeutic agents or therapies, wherein the method does not comprise daily administration of RvE1 and wherein the mineral amino acid salt has a structure of Formula IV, or an enantiomer, polymorph, solvate, or hydrate thereof:

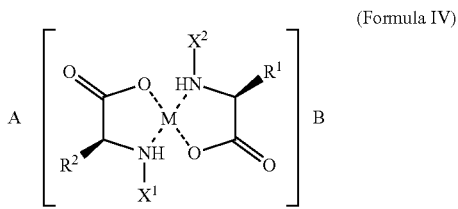

(Formula IV)

wherein

M is a divalent metal selected from magnesium ($Mg^{2+}$), calcium ($Ca^{2+}$), and zinc ($Zn^{2+}$);

A and B are each RvE1;

$R^1$ and $R^2$ are each independently a $C_1$-$C_{10}$ alkyl comprising at least one basic function; and $X^1$ and $X^2$ are each independently H or CO—Z and Z is a peptide comprising 1 to 5 amino acids.

2. The method of claim 1, wherein M is selected from magnesium ($Mg^{2+}$) or calcium ($Ca^{2+}$).

3. The method of claim 2, wherein $R^1$ and $R^2$ are each independently —$(CH_2)_3$—$Y^1$, and —$(CH_2)_4$—$Y^2$, and $Y^1$ and $Y^2$ are each selected from a positively charged primary amine, a positively charged secondary amine, a positively charged tertiary amine, and a positively charged guanidine.

4. The method of claim 3, wherein $X^1$ and $X^2$ are each H.

5. The method of claim 2, wherein $R^1$ and $R^2$ are each —$(CH_2)_4$—$Y^2$ and $Y^2$ is $NH_3^+$.

6. The method of claim 1, wherein M is magnesium ($Mg^{2+}$), $R^1$ and $R^2$ are each —$(CH_2)_4$—$Y^2$ and $Y^2$ is —$NH_3^+$, $X^1$ and $X^2$ are each H, which compound is referred to as bis RvE1 Mg-di-lysinate.

7. The method of claim 1, wherein the cancer is selected from a brain cancer, breast cancer, bladder cancer, colorectal cancer, gastric cancer, lung cancer, ovarian cancer, pancreatic cancer, prostate cancer, esophageal cancer, head and neck cancer, liver cancer, skin cancer, renal cell carcinoma, or sarcoma.

8. The method of claim 7, wherein the cancer is selected from brain cancer, colorectal cancer, gastric cancer, liver cancer, lung cancer, ovarian cancer, pancreatic cancer, or skin cancer.

9. The method of claim 7, wherein the cancer is brain cancer which is a glioblastoma.

10. The method of claim 7, wherein the breast cancer is a triple negative breast cancer.

11. The method of claim 7, wherein the skin cancer is a melanoma.

12. The method of claim 7, wherein the pancreatic cancer is a pancreatic adenocarcinoma.

13. The method of claim 7, wherein the colorectal cancer is a colorectal adenocarcinoma.

14. The method of claim 1, wherein the cancer is a metastatic cancer.

15. The method of claim 1, wherein the cancer is a local, regional, or metastatic cancer.

16. The method of claim 1, wherein the pharmaceutical composition is administered orally or parenterally.

17. The method of claim 16, wherein the parenteral administration is subcutaneous, intraperitoneal, intramuscular, or intravenous.

18. The method of claim 16, wherein the pharmaceutical composition is administered sublingually or by inhalation.

19. The method of claim 1, wherein the method comprises administering the resolvin as an adjuvant or neoadjuvant to surgery or radiation therapy.

20. The method of claim 19, wherein the surgery is curative surgery or debulking surgery.

21. The method of claim 19, wherein the radiation therapy is curative or palliative.

22. The method of claim 1, wherein the method comprises administering the resolvin in combination with one or more additional therapeutic agents, or one or more additional therapies.

23. The method of claim 22, wherein the one or more additional therapeutic agents is an antimetabolite, a DNA alkylator, a DNA binder or cleaver, a tubulin or microtubule inhibitor, a DNA topoisomerase inhibitor, an angiogenesis inhibitor, a proteasome inhibitor, a CDK inhibitor, a tyrosine kinase inhibitor, or an immunotherapy agent.

24. The method of claim 22, wherein the one or more additional therapeutic agents is gemcitabine, cisplatin, 5-fluorouracil, cetuximab or erlotinib.

25. The method of claim 22, wherein the one or more additional therapeutic agents is an immune checkpoint inhibitor (ICI) or a combination of two or more ICI's.

26. The method of claim 25, wherein the immune checkpoint inhibitor (ICI) is selected from an anti: PD-1 antibody, an anti-PD-2 antibody, an anti-CTLA4 antibody, an anti-PD-L1 antibody, an anti-PD-L2 antibody, an anti-CD47 antibody, a LAG-3 inhibitor antibody, or any combination thereof.

27. The method of claim 26, wherein the immune checkpoint inhibitor is pembrolizumab, nivolumab, atezolizumab, avelumab, durvalumab, cemiplimab, ipilimumab, tremelimumab, or magrolimab, relatlimab, or any combination thereof.

28. The method of claim 25, wherein the immune checkpoint inhibitor (ICI) is administered in combination with one or more additional therapies selected from surgery, chemotherapy, radiation therapy, targeted therapy, hormone therapy, CAR T cell therapy, gene therapy, or microbiome therapy.

29. The method of claim 22, wherein the cancer is pancreatic cancer and the one or more additional therapeutic agents is a combination of an anti-PD-1 antibody or anti-PD-L1 antibody and an anti-CTLA4 antibody or a combination of an anti-PD-1 antibody or anti-PD-L1 antibody and a LAG-3 inhibitor, or any combination thereof.

30. The method of claim 22, wherein the cancer is pancreatic cancer and the one or more additional therapies comprises a chemotherapy or targeted therapy regimen selected from the group consisting of FOLFIRINOX, gemcitabine with or without nab-paclitaxel, a PARP inhibitor, and capecitabine.

31. The method of claim 22, wherein the cancer is lung cancer and the one or more additional therapies is an immune checkpoint inhibitor selected from the group consisting of an anti-PD-1 antibody, an anti-PD-L1 antibody, anti-CTLA4 antibody, an anti-CD47 antibody, and a LAG-3 inhibitor, or any combination thereof.

32. The method of claim 22, wherein the cancer is lung cancer and the one or more additional therapies comprises a chemotherapy or targeted therapy regimen including one or more of carboplatin, etoposide, cisplatin, lurbinectedin and irinotecan.

33. The method of claim 22, wherein the cancer is colon cancer and the one or more additional therapies is selected from the group consisting of an anti-PD-1 antibody, an anti-PD-L1 antibody, anti-CTLA4 antibody, an anti-CD47 antibody, and a LAG-3 inhibitor, or any combination thereof.

34. The method of claim 22, wherein the cancer is colon cancer and the one or more additional therapies comprises a chemotherapy or targeted therapy regimen including one or more of bevacizumab, FOLFIRI, and trifluridine plus tipiracil.

35. The method of claim 22, wherein the cancer is melanoma and the one or more additional therapies is an immune checkpoint inhibitor selected from the group consisting of an anti-PD-1 antibody, an anti-PD-L1 antibody, anti-CTLA4 antibody, an anti-CD47 antibody, and a LAG-3 inhibitor, or any combination thereof.

36. The method of claim 22, wherein the cancer is melanoma and the one or more additional therapies is a chemotherapy or targeted therapy regimen including one or more of binimetinib plus encorafenib, vemurafenib plus cobimetinib, and dabrafenib plus trametinib.

37. The method of claim 22, wherein the one or more additional therapeutic agents, or the one or more additional therapies is surgery, chemotherapy, radiation therapy, targeted therapy, immunotherapy, hormone therapy, CAR T cell therapy, gene therapy, or microbiome therapy.

38. A method for treating cancer in a subject in need of such treatment, the method comprising administering to the subject a pharmaceutical composition comprising a mineral amino acid salt of resolvin E1 ("RvE1") in a therapeutic regimen of every six days (Q6D) or every seven days (Q7D), as adjuvant or neo-adjuvant therapy in combination with an immune checkpoint inhibitor (ICI) or a combination of two or more ICI's, wherein the method does not comprise daily administration of RvE1 and wherein the mineral amino acid salt has a structure of Formula IV, or an enantiomer, polymorph, solvate, or hydrate thereof:

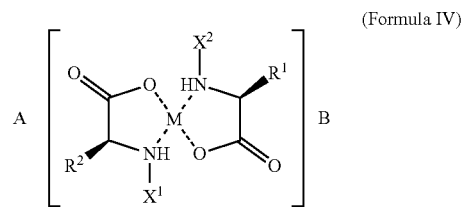

(Formula IV)

wherein

M is a divalent metal selected from magnesium ($Mg^{2+}$), calcium ($Ca^{2+}$), and zinc ($Zn^{2+}$);

A and B are each RvE1;

$R^1$ and $R^2$ are each independently a $C_1$-$C_{10}$ alkyl comprising at least one basic function; and $X^1$ and $X^2$ are each independently H or CO—Z and Z is a peptide comprising 1 to 5 amino acids.

39. The method of claim 38, wherein $R^1$ and $R^2$ are each —$(CH_2)_4$-$Y^2$, $Y^2$ is —$NH_3^+$, and $X^1$, $X^2$ are H.

40. The method of claim 39, wherein M is magnesium ($Mg^{2+}$), which compound is referred to as bis RvE1 Mg-di-lysinate.

41. The method of claim 40, wherein the immune checkpoint inhibitor (ICI) is an anti-PD-1 antibody, an anti-PD-2 antibody, an anti-CTLA4 antibody, an anti-PD-L1 antibody, an anti-PD-L2 antibody, an anti-CD47 antibody, a LAG-3 inhibitor antibody, or any combination thereof.

42. The method of claim 41, wherein the immune checkpoint inhibitor is pembrolizumab, nivolumab, atezolizumab, avelumab, durvalumab, cemiplimab, ipilimumab, tremelimumab, or magrolimab, relatlimab, or any combination thereof.

43. The method of claim 38, wherein the immune checkpoint inhibitor (ICI) is an anti-PD-1 antibody, an anti-PD-2 antibody, an anti-CTLA4 antibody, an anti-PD-L1 antibody, an anti-PD-L2 antibody, an anti-CD47 antibody, a LAG-3 inhibitor antibody, or any combination thereof.

44. The method of claim 43, wherein the immune checkpoint inhibitor is pembrolizumab, nivolumab, atezolizumab, avelumab, durvalumab, cemiplimab, ipilimumab, tremelimumab, or magrolimab, relatlimab, or any combination thereof.

* * * * *